United States Patent
Kang

(10) Patent No.: US 10,182,560 B2
(45) Date of Patent: Jan. 22, 2019

(54) TRANSGENE CONSTRUCT ENCODING DELTA 12 FATTY ACID

(71) Applicant: THE GENERAL HOSPITAL CORPORATION, Boston, MA (US)

(72) Inventor: Jing X. Kang, North Andover, MA (US)

(73) Assignee: THE GENERAL HOSPITAL CORPORATION, Boston, MA (US)

( * ) Notice: Subject to any disclaimer, the term of this patent is extended or adjusted under 35 U.S.C. 154(b) by 0 days.

(21) Appl. No.: 15/127,295

(22) PCT Filed: Mar. 20, 2015

(86) PCT No.: PCT/US2015/021689
§ 371 (c)(1),
(2) Date: Sep. 19, 2016

(87) PCT Pub. No.: WO2015/143284
PCT Pub. Date: Sep. 24, 2015

(65) Prior Publication Data
US 2017/0172118 A1 Jun. 22, 2017

Related U.S. Application Data

(60) Provisional application No. 61/968,754, filed on Mar. 21, 2014.

(51) Int. Cl.
| | | |
|---|---|---|
| *C12N 15/00* | (2006.01) | |
| *A01K 67/027* | (2006.01) | |
| *C12N 9/02* | (2006.01) | |
| *A23L 33/12* | (2016.01) | |
| *A23L 33/00* | (2016.01) | |
| *A61K 31/202* | (2006.01) | |

(52) U.S. Cl.
CPC .......... *A01K 67/0275* (2013.01); *A23L 33/12* (2016.08); *A23L 33/30* (2016.08); *A61K 31/202* (2013.01); *C12N 9/0071* (2013.01); *C12Y 114/19* (2013.01); *A01K 2217/052* (2013.01); *A01K 2217/15* (2013.01); *A01K 2227/105* (2013.01); *A01K 2267/01* (2013.01); *A01K 2267/02* (2013.01); *A01K 2267/0362* (2013.01); *A23V 2002/00* (2013.01)

(58) Field of Classification Search
USPC ....................................... 536/23.1; 435/320.1
See application file for complete search history.

(56) References Cited

U.S. PATENT DOCUMENTS 7,238,851 B2    6/2007 Kang

FOREIGN PATENT DOCUMENTS

| CN | 101886061 | * 11/2010 |
|---|---|---|
| CN | 101886061 A | 11/2010 |
| WO | 2005/077022 A2 | 8/2005 |

OTHER PUBLICATIONS

Google translation of Tang CN 101886061A, 2010.*
Das et al., "Transgenic fat-1 mouse as a model to study the pathophysiology of cardiovascular, neurological and psychiatric disorders", Lipids in Health and Disease 8:61 (2009). (13 pages).
Kang, "Fat-1 Transgenic Mice: A New Model for Omega-3 Research", Prostaglandins, Leukotrienes and Essential Fatty Acids 77(5-6):263-267 (2007).
Lai et al., "Generation of cloned transgenic pigs rich in omega-3 fatty acids", Nature Biotechnology 24(4):435-436 (2006).
Morimoto et al., "Hot Topic: Endogenous Production of n-3 and n-6 Fatty Acids in Mammalian Cells", Journal of Dairy Science 88:1142-1146 (2005).
Pai et al., "Transgenic Mice Convert Carbohydrates to Essential Fatty Acids", PLoS One 9(5):e97637 (2014). (6 pages).

* cited by examiner

*Primary Examiner* — Michael C Wilson
(74) *Attorney, Agent, or Firm* — Nixon Peabody LLP

(57) ABSTRACT

Various aspects provided herein relate to compositions and methods for altering the content of polyunsaturated fatty acids in animals, e.g., non-human animals. Transgenic animals (e.g., non-human animals) that are capable of converting carbohydrates and/or saturated fats to polyunsaturated fatty acids (e.g., n-6 and/or n-3 fatty acids) and uses thereof are also provided herein.

5 Claims, 5 Drawing Sheets
Specification includes a Sequence Listing.

TRANSGENE CONSTRUCT ENCODING DELTA 12 FATTY ACID

CROSS-REFERENCE TO RELATED APPLICATIONS

This application is a 35 U.S.C. § 371 National Phase Entry Application of International Application No. PCT/US15/21689 filed Mar. 20, 2015, which designates the U.S., and which claims benefit under 35 U.S.C. § 119(e) of the U.S. Provisional Application No. 61/968,754, filed Mar. 21, 2014, the contents of each of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Jun. 19, 2015, is named 030258-081021-PCT_SL.txt and is 20,975 bytes in size.

TECHNICAL FIELD

Various aspects described herein relate to compositions and methods for altering the content of polyunsaturated fatty acids in animals, e.g., non-human mammals. Transgenic animals (e.g., non-human mammals) that are capable of converting carbohydrates and/or saturated fats to polyunsaturated fatty acids and uses thereof are also provided herein.

BACKGROUND

The worldwide trend of increased saturated fat and carbohydrate consumption with increased omega-6 (n-6) and decreased omega-3 (n-3) fatty acid intake has coincided with the growing prevalence of chronic, life-threatening diseases, suggesting a critical link between the shift in our dietary composition and today's health epidemic (Leaf and Weber (1987) *Am. J. Clin. Nutr.* 45: 1048-1053; Cordain, L. et al. (2005) *Am. J. Clin. Nutr.* 81: 341-354). Saturated fats can be readily produced from carbohydrates in mammals, and both saturated fats and carbohydrates are highly abundant in the modern Western diet (Institute of Medicine of the National Academies. Dietary fats: total fat and fatty acids. In: *Dietary reference intakes for energy, carbohydrate, fiber, fat, fatty acids, cholesterol, protein, and amino acids (macronutrients)*. (2002) Washington, D.C.: The National Academy Press, pp. 335-432); in contrast, omega-3 fatty acids cannot be made de novo nor converted from other nutrients in mammals, and therefore must be obtained from dietary sources (e.g., fish oil). Id.

Normally, mammals readily obtain saturated fatty acids (SFA) from either the diet or endogenous synthesis from glucose or amino acids (Volpe and Vagelos (1976) *Physiol. Rev.* 56, 339-417), and monounsaturated fatty acids (MUFA) can also be obtained from the diet or converted from SFA by the stearoyl-CoA desaturase-1 (SCD-1) gene (Paton and Ntambi (2009) *Am. J. Physiol. Endocrinol. Metab.* 297: E28-37). On the other hand, n-6 and n-3 PUFA cannot be inter-converted or synthesized de novo in mammals and are mainly acquired through the diet (Leonard et al. (2004) *Prog. Lipid Res.* 43: 36-54; Gebauer et al. (2006) *Am. J. Clin. Nutr.* 83, 1526s-1535s). In this context, to increase the tissue content of essential fatty acids, they must be supplemented in the diet, such as adding vegetable oils (e.g., corn, soybean, safflower, etc.) for n-6 PUFA or fish oil for n-3 PUFA.

The high fat diet has been widely investigated for its role in the development of metabolic diseases (Kuller (1997) *J. Am. Diet. Assoc.* 97: S9-15; Joint WHO/FAO Expert Consultation. (2003) *Diet, Nutrition and the Prevention of Chronic Diseases* (WHO technical report series 916). World Health Organization, Geneva. pp. 81-94). However, the interpretation of results from these reports often does not recognize the different types of fats—including saturated fatty acids (SFA), monounsaturated fatty acids (MUFA), n-6 polyunsaturated fatty acids (PUFA), and n-3 PUFA—that can each contribute differential effects to study outcomes (Weisburger (1997) *J. Am. Diet. Assoc.* 97, S16-23; Simopoulos (2008) *Exp. Biol. Med.* 233, 674-688). In addition, comparative nutrition studies conventionally utilize diets with different fat sources, introducing other variables that can become confounding factors (Kang (2011) *World. Rev. Nutr. Diet.* 102: 22-29). For example, the presence of many other components, other than n-6 or n-3 fatty acids, in the supplemented oils makes it difficult to interpret the experimental outcome for the authentic effect of n-6 or n-3 fatty acids. By overlooking or failing to isolate the respective impact of specific fats, the existing research has often presented inconsistent or contradicting conclusions, causing confusion among scientists and the public alike. Accordingly, there is a need for a reliably defined source of essential fatty acid type and quantity, which can be used as food sources to supplement essential fatty acids or as an experimental model for study of conditions associated with fat metabolism.

SUMMARY

Embodiments of various aspects described herein are, in part, based on the discovery that delta 12 fatty acid desaturase gene (fat-2) and n-3 fatty acid desaturase gene (fat-1) from low life form (e.g., roundworms) can be optimized and introduced into higher life form or genomically complex animal cells (e.g., mammalian cells) to generate a non-human animal that can produce essential n-6 and n-3 fatty acids from saturated fats and/or carbohydrates. In accordance with one aspect of the discovery, the inventor has successfully engineered transgenic mice to carry both optimized fat-2 and fat-1 from roundworm *Caenorhabditis elegans* (*C. elegans*) such that the transgenic mice (referred to as "Omega mice" hereafter) can produce essential n-6 and n-3 fatty acids from saturated fats and/or carbohydrates. Further, the inventor has shown that Omega mice exhibited a balanced n-6/n-3 fatty acids ratio in body tissues. For example, when maintained on a high-fat diet lacking essential fatty acids or a high-carbohydrate, no-fat diet, the Omega mice exhibited high tissue levels of both n-6 and n-3 fatty acids, with a ratio of ~1:1. Furthermore, when the three genotypes—wild-type (incapable of producing essential fatty acids), fat-2 transgenic (producing only n-6 and no n-3 fatty acids), and Omega transgenic (producing both n-6 and n-3 fatty acids) mice—were fed the same diet, they presented distinct profiles of characteristics associated with many metabolic diseases (e.g., hepatic lipogenesis, gut microbiota, and low-grade inflammation). The discovery thus provides a novel transgenic non-human animal model that can endogenously synthesize essential n-6 and n-3 fatty acids, e.g., for addressing fat metabolism and disease, as well as an innovative technology for increased production of both n-6 and n-3 essential fatty acids.

Accordingly, some aspects described herein provide for compositions and methods for effectively modifying the contents of polyunsaturated fatty acids (PUFAs), e.g., n-6 and n-3 fatty acids, in animals or cells thereof (i.e., cells other than those of *C. elegans*, for example, but not limited to, mammalian cells). In some embodiments, an optimized fat-2 and/or fat-1 nucleic acid or amino acid sequence or a biologically active variant thereof can be operably linked to a regulatory sequence or a constitutively active or tissue-specific promoter. Regulatory sequences encompass not only promoters, but also enhancers or other expression control sequence, such as a polyadenylation signal, that facilitates expression of the nucleic acid. The engineered animal cells (e.g., in vitro, in vivo or ex vivo) that can produce n-6 and/or n-3 fatty acids from saturated fat and/or carbohydrates, transgenic non-human animals containing the cells, food products obtained from those transgenic non-human animals (e.g., meat or other edible parts of the animals (e.g., liver, kidney, or thymus), and methods of using the same are also described herein.

In one aspect, provided herein relates to a nonhuman transgenic animal having a genome comprising a first exogenous and/or heterologous nucleic acid molecule operably linked to a promoter, wherein the first exogenous and/or heterologous nucleic acid molecule comprises a nucleotide sequence encoding an enzyme that converts saturated fat and/or carbohydrates to omega-6 (or n-6 fatty acids), wherein upon expression of the first exogenous and/or heterologous nucleic acid molecule within the transgenic animal, the transgenic animal produces omega-6 (or n-6 fatty acids) from saturated fats and/or carbohydrates. In some embodiments, the content of n-6 fatty acids in the transgenic animal is increased upon expression of the first exogenous and/or heterologous nucleic acid molecule, as compared to the content in a wild-type animal.

In some embodiments, the nucleotide sequence encoding an enzyme that converts saturated fat and/or carbohydrates to n-6 fatty acids can be derived from any species that is capable of synthesizing n-6 fatty acids from carbohydrates and/or saturated fat de novo or in vivo within a cell or animal. For example, an enzyme that converts saturated fat and/or carbohydrates to n-6 fatty acids can be derived from invertebrate animals, insects, worms, plants, bacteria, fungus, fish, crustaceans, molluscs, nematodes, cyanobacteria, or algae.

By way of example only, in some embodiments, the enzyme that converts saturated fat and/or carbohydrates to n-6 fatty acids can comprise delta 12 fatty acid desaturase or a biologically active variant thereof. In one embodiment, the nucleotide sequence encoding a delta 12 fatty acid desaturase or a biologically active variant thereof can be derived from a worm. In one embodiment, the nucleotide sequence encoding a delta 12 fatty acid desaturase or a biologically active variant thereof can be derived from *C. elegans*.

In some embodiments, the nucleotide sequence encoding delta 12 fatty acid desaturase can correspond to a wild-type delta 12 fatty acid desaturase.

In some embodiments, the nucleotide sequence encoding delta 12 fatty acid desaturase can correspond to a modified delta 12 fatty acid desaturase, as compared to a wild-type delta 12 fatty acid desaturase. For example, to enable higher expression of a heterologous gene in a host, the codon of the nucleotide sequence can be optimized based on the host's sequence of a similar or equivalent gene. In one embodiment, to enhance the expression of the *C. elegans* fat-2 gene in mammalian cells or mammals, the codon of the fat-2 sequence can be optimized based on the mammalian desaturase sequence. In one embodiment, the optimized nucleotide sequence of fat-2 is shown in SEQ ID NO. 1.

In some embodiments, the first exogenous and/or heterologous nucleic acid molecule can comprise a nucleotide sequence encoding delta 12 fatty acid desaturase or a biologically active variant thereof. Biologically active variants of the delta 12 fatty acid desaturase are variants that retain sufficient biological activity of a wild-type or modified delta 12 fatty acid desaturase (e.g., encoded by SEQ ID NO. 1) to convert carbohydrates and/or saturated fat to n-6 fatty acids. For example, biologically active variants of the delta 12 fatty acid desaturase can include mutants or fragments of that enzyme that retain at least 25% or higher of the biological activity of wild-type or modified delta 12 fatty acid desaturase (e.g., encoded by SEQ ID NO. 1) to convert carbohydrates and/or saturated fat to n-6 fatty acids. For example, a fragment of a delta 12 fatty acid desaturase enzyme is a biologically active variant of the full-length enzyme when the fragment is capable of converting carbohydrates and/or saturated fat to n-6 fatty acids and the conversion is at least about 25% or higher as efficient as the wild-type or modified enzyme does so under the same conditions. The biologically active variants of a delta 12 fatty acid desaturase can also contain one or more amino acid substitutions (e.g., 1%, 5%, 10%, 20%, 25% or more of the amino acid residues in the enzyme sequence can be replaced with another amino acid residue). These substitutions can constitute conservative amino acid substitutions, which are known in the art. In some embodiments, the biologically active variants of a delta 12 fatty acid desaturase can be at least about 70% or higher identical to the sequence of the wild-type or modified delta 12 fatty acid desaturase (e.g., SEQ ID NO. 1).

In some embodiments, the ratio of n-6 fatty acid to n-3 fatty acid in the transgenic animal can be greater than 1:1 or higher, upon expression of the first exogenous and/or heterologous nucleic acid molecules in the transgenic animal.

In some embodiments, the genome of the nonhuman transgenic animal can further comprise a second exogenous and/or heterologous nucleic acid molecule. In some embodiments, the second exogenous and/or heterologous nucleic acid molecule can comprise a nucleotide sequence encoding an enzyme that converts at least one n-6 fatty acid to one or more n-3 fatty acids, wherein upon expression of the first and second exogenous and/or heterologous nucleic acid molecules in the transgenic animal, the transgenic animal produces n-3 and n-6 (at least some of which can be converted to n-3) from saturated fats and/or carbohydrates. In some embodiments, the content of n-3 fatty acids in the transgenic animal is increased upon expression of the second exogenous and/or heterologous nucleic acid molecule, as compared to the n-3 fatty acids content in a wild-type animal.

In some embodiments, the nucleotide sequence encoding an enzyme that converts at least one n-6 fatty acid to one or more n-3 fatty acids can be derived from any species that can synthesize n-3 fatty acids from n-6 fatty acids de novo or in vivo within a cell or an animal. For example, an enzyme that converts at least one n-6 fatty acid to one or more n-3 fatty acids can be derived from invertebrate animals, insects, worms, plants, bacteria, fungus, fish, crustaceans, molluscs, nematodes, cyanobacteria, or algae.

By way of example only, in some embodiments, the enzyme that converts at least one n-6 fatty acid to one or more n-3 fatty acids can comprise an n-3 fatty acid desaturase or a biologically active variant thereof. In one embodiment, the nucleotide sequence encoding an n-3 fatty acid desaturase or a biologically active variant thereof can be derived from a worm. In one embodiment, the nucleotide sequence encoding an n-3 fatty acid desaturase or a biologically variant thereof can be derived from *C. elegans*.

In some embodiments, the nucleotide sequence encoding n-3 fatty acid desaturase can correspond to a wild-type n-3 fatty acid desaturase.

In some embodiments, the nucleotide sequence encoding n-3 fatty acid desaturase can correspond to a modified n-3 fatty acid desaturase, as compared to a wild-type n-3 fatty acid desaturase. As discussed above, to enable higher expression of a heterologous gene in a host, the codon of the nucleotide sequence can be, for example, optimized based on the host's sequence of a similar or equivalent gene. In one embodiment, to enhance the expression of the *C. elegans* fat-1 gene in mammalian cells or mammals, the codon of the fat-1 gene can be optimized based on the mammalian desaturase sequence. In one embodiment, the optimized nucleotide sequence of fat-1 is shown in SEQ ID NO. 2.

In some embodiments, the nucleotide sequence of the second exogenous and/or heterologous nucleic acid molecule that encodes an enzyme for converting at least one n-6 fatty acid to one or more n-3 fatty acids is an n-3 fatty acid denaturase or a biologically active variant thereof. In these embodiments, expression of the n-3 fatty acid denaturase or a biologically active variant thereof enables the transgenic animal to convert at least one n-6 fatty acid to one or more n-3 fatty acids. Thus, the transgenic animal carrying both the first and second exogenous and/or heterologous nucleic acid molecules can produce n-3 fatty acids and n-6 fatty acids (at least some of which can be converted to n-3 fatty acids) from saturated fats and/or carbohydrates.

Biologically active variants of an n-3 fatty acid desaturase are variants that retain sufficient biological activity of a wild-type or modified n-3 fatty acid desaturase (e.g., SEQ ID NO. 2) to convert at least one n-6 fatty acid to one or more n-3 fatty acids. For example, biologically active variants of n-3 fatty acid desaturase can include mutants or fragments of that enzyme that retain at least 25% or higher of the biological activity of wild-type or modified n-3 fatty acid desaturase (e.g., SEQ ID NO. 2) to convert at least one n-6 fatty acid to one or more n-3 fatty acids. For example, a fragment of an n-3 fatty acid desaturase enzyme is a biologically active variant of the full-length enzyme when the fragment converts at least one n-6 fatty acid to one or more n-3 fatty acids and the conversion is at least 25% or higher as efficient as the wild-type or modified enzyme does so under the same conditions. The biologically active variants of an n-3 fatty acid desaturase can also contain one or more amino acid substitutions (e.g., 1%, 5%, 10%, 20%, 25% or more of the amino acid residues in the enzyme sequence can be replaced with another amino acid residue). These substitutions can constitute conservative amino acid substitutions, which are known in the art. In some embodiments, the biologically active variants of an n-3 fatty acid desaturase can be at least about 70% identical to the sequence of the wild-type or modified n-3 fatty acid desaturase (e.g., SEQ ID NO. 2).

In some embodiments where the nonhuman transgenic animal comprises both the first and the second exogenous and/or heterologous nucleic acid molecules, the ratio of n-6 fatty acid to n-3 fatty acid in the transgenic animal can be about 1:1 or lower, upon expression of the first and second exogenous and/or heterologous nucleic acid molecules in the transgenic animal.

The "animal" to be made transgenic refers to any animal that cannot produce n-6 and/or n-3 de novo or in vivo in its body. In some embodiments, the nonhuman transgenic animal can be a vertebrate. In some embodiments, the nonhuman transgenic animal can be a mammal. In some embodiments, the nonhuman transgenic animal can be selected from the group consisting of a cow, a mouse, a rat, a pig, a sheep, a goat, a rabbit, a buffalo, a poultry, livestock, a livestock, a fish, a deer, or a domestic animal. In some embodiments, the transgenic animal refers to a large animal (e.g., cow, pig, sheep, goat, rabbit, deer, chicken and other fowl (e.g., goose, duck, pheasant, and game hen)) and/or fish or other edible animals that are farmed or that reside in rivers, lakes, streams, or the sea. In some embodiments, the transgenic animal is a nonhuman mammal. In some embodiments, the transgenic animal is a fish.

The transgenic animals, tissues or cells derived therefrom can allow one to study a cellular mechanism or a biological condition mediated by n-6 fatty acids and/or n-3 fatty acids without feeding them with different fat sources that could in turn introduce additional variables into the system. Accordingly, in some embodiments, the genome of the nonhuman transgenic animal can further comprise a gene modification. The gene modification can comprise addition, deletion, and/or mutation of a gene of interest. For example, the gene of interest can be associated with a cellular mechanism or a biological condition associated with fat metabolism. In some embodiments, gene modification can comprise modification of a host's gene. In some embodiments, the gene modification can comprise expression of a heterologous gene. The heterologous gene can be, for example, a gene that is associated with fat metabolism pathway, a therapeutic gene (e.g., a receptor for a small molecule or chemotherapeutic agent) or a marker gene (e.g., a sequence encoding a fluorescent protein, such as green fluorescent protein (GFP) or enhanced GFP (EGFP)). The heterologous gene can be co-expressed (by way of the same or a separate expression vector) with the first and/or second exogenous and/or heterologous nucleic acid molecules described herein (e.g., encoding fat-2 and/or fat-1).

Depending on whether the construct used contains a constitutively active promoter or a tissue-specific promoter (e.g., a promoter that is active in, e.g., skeletal muscle cells, breast tissue cells, colon tissue cells, neurons, retinal cells, pancreatic cells (e.g., islet cells), etc.), the first and/or second exogenous and/or heterologous nucleic acid molecules described herein (e.g., encoding fat-2 and/or fat-1 gene) can be expressed globally within the animal body or in a tissue-specific manner.

The cells and tissues of the transgenic animals described herein can contain an altered PUFA content. For example, the cells and tissues of the transgenic animals carrying both of the first and the second exogenous and/or heterologous nucleic acid molecules (e.g., encoding fat-2 and fat-1 gene) can be more desirable for consumption because they are engineered to have a cell or tissue content with a high level of n-3 fatty acids but a reduced level of n-6 fatty acids, as compared to the transgenic animals without these genes. Thus, transgenic livestock or animals that are consumed (e.g., by human or mammals) as food, when are engineered to express a first heterologous enzyme that converts saturated fat and/or carbohydrates to n-6 fatty acids and a second heterologous enzyme that converts at least one n-6 fatty acid to one or more n-3 fatty acids (e.g., desaturase enzymes encoded by the fat-2 and fat-1 gene, respectively), can be superior or healthier sources of food.

Accordingly, other aspects provided herein relate to food or food products obtained, derived, or processed from one or more embodiments of the nonhuman transgenic animals described herein, wherein the nonhuman transgenic animals carry a first heterologous gene that converts saturated fat and/or carbohydrates to n-6 fatty acids and a second heterologous gene that converts at least one n-6 fatty acid to one or more n-3 fatty acids. In one embodiment, the first heterologous gene can comprise a fat-2 gene. In one embodiment, the second heterologous gene can comprise a fat-1 gene. Non-limiting examples of food or food products can include, but are not limited to, meat, milk, tissue, tendons, oil, eggs, dairy products (e.g., cheese), and any combinations thereof. In some embodiments, the ratio of n-6 fatty acids to omega-3 fatty acids in food products described herein can be about 1:1 or less.

The food or food products described herein (e.g., food or food products obtained, derived, or processed from nonhuman transgenic animals carrying both fat-2 and fat-1 genes) can be provided to healthy individuals or to those suffering from a deficiency in n-3 fatty acids. Diseases or disorders associated with a deficiency in n-3 fatty acids are known in the art, including, e.g., but not limited to obesity, diabetes, cancer, heart diseases, inflammatory diseases, neurodegenerative diseases, neuropsychiatric diseases, osteoarthritis, lupus, non-alcoholic fatty liver disease, colitis, and any combinations thereof. Accordingly, methods for treating a condition (e.g., a disease or disorder) associated with a deficiency in n-3 fatty acids are also provided herein. By administering to a subject diagnosed to have or have a risk for a condition (e.g., a disease or disorder) associated with a deficiency in n-3 fatty acids, the food or food products described herein (e.g., food or food product obtained, derived, or processed from a nonhuman transgenic animal carrying both fat-2 and fat-1 genes), the n-3 fatty acid content in the subject can be increased or the ratio of the n-6 fatty acids to n-3 fatty acids in the subject can be decreased, thereby treating the condition in the subject.

Further aspects provide methods of increasing n-3 fatty acid content in a non-human animal or a food product derived therefrom. The method comprises feeding a nonhuman transgenic animal described herein that converts carbohydrates and/or saturated fat to n-6 and n-3 fatty acids (e.g., a transgenic animal carrying both fat-2 and fat-1 genes described herein) with a diet high in carbohydrates and/or saturated fat. The transgenic animal can convert at least a portion (e.g., at least 30% or more) of the carbohydrates and/or saturated fat from its diet to n-6 and n-3 fatty acids.

In some embodiments, the diet fed to the transgenic animals described herein can have PUFA (e.g., essential fatty acids) of less than 30% or lower. In some embodiments, the diet fed to the transgenic animals can exclude any PUFA or essential fatty acids.

In some embodiments, upon feeding the transgenic animals with a diet high in carbohydrates and/or saturated fat, the ratio of n-6 fatty acids to the omega 3 fatty acids in the transgenic animal or food product derived therefrom can be about 1 or less. In some embodiments, at least a portion of the n-6 fatty acids, e.g., converted from the carbohydrates and/or saturated fat in the diet, or directly from the diet, are not converted to n-3 fatty acids. In some embodiments, substantially all of the n-6 fatty acids, e.g., converted from the carbohydrates and/or saturated fat in the diet, or directly from the diet, are converted to n-3 fatty acids.

In one aspect, provided herein is a transgene construct comprising a first exogenous and/or heterologous nucleic acid molecule operably linked to a promoter, wherein the first exogenous and/or heterologous nucleic acid molecule comprises a nucleotide sequence encoding a delta 12 fatty acid desaturase (e.g., a fat-2 gene) or a biologically active variant thereof, and wherein the promoter directs expression of the first exogenous and/or heterologous nucleic acid molecule in an animal cell upon introduction of the transgene construct into the cell. For example, the transgene construct can be introduced into the cell by microinjection.

In some embodiments, the first exogenous and/or heterologous nucleic acid molecule can comprise (i) a nucleotide sequence of SEQ ID NO. 1 or (ii) a nucleotide sequence that is a biologically active variant of SEQ ID NO. 1 and is at least about 70% identical to SEQ ID NO. 1.

In some embodiments, the transgene construct can further comprise a second exogenous and/or heterologous nucleic acid molecule, the second exogenous and/or heterologous nucleic acid molecule comprising a nucleotide sequence encoding an enzyme that converts an n-6 fatty acid to an n-3 fatty acid. In some embodiments, the nucleotide sequence encoding an enzyme that converts an n-6 fatty acid to an n-3 fatty can be a nucleotide sequence encoding an n-3 fatty acid desaturase, or a biologically active variant thereof.

In some embodiments, the second exogenous and/or heterologous nucleic acid molecule can comprise (i) a nucleotide sequence of SEQ ID NO. 2 or (ii) a nucleotide sequence that is a biologically active variant of SEQ ID NO. 2 and is at least about 70% identical to SEQ ID NO. 2.

In some embodiments where the second exogenous and/or heterologous nucleic acid molecule is present in a transgene construct described herein, the second exogenous and/or heterologous nucleic acid molecule can be operably linked to the same promoter or a different promoter. The promoter can direct expression of the second exogenous and/or heterologous nucleic acid in the transgenic animal cell upon introduction of the transgene construct into the cell.

Examples of animal cells to which the transgene construct can be introduced include, but are not limited to, animal cells derived from a cow, a mouse, a rat, a pig, a sheep, a goat, a fish, a buffalo, a rabbit, a poultry, a livestock or a domestic animal.

Methods of determining an effect of n-6 and/or n-3 fatty acids on a condition (e.g., a disease or disorder) associated with fat metabolism are also provided herein. In some embodiments, the method comprises (a) inducing in a nonhuman transgenic animal described herein, or cells or tissues derived therefrom described herein, at least one phenotype of a condition (e.g., a disease or disorder) associated with fat metabolism; (b) feeding the nonhuman transgenic animal, or cells or tissues derived therefrom with a composition high in carbohydrates and/or saturated fat; (c) detecting response(s) of the nonhuman transgenic animal from (b); and (d) comparing the detected response(s) of the nonhuman transgenic animal with a control, wherein the difference in the response between the nonhuman transgenic animal and the control determines an effect of n-6 and/or n-3 fatty acids on the condition.

In some embodiments, a phenotype of a condition (e.g., a disease or disorder) associated with fat metabolism can be induced by modifying at least one gene in the genome of the nonhuman transgenic animal, or cells or tissues derived therefrom, where the gene is associated with the condition. The gene modification can include, e.g., addition, deletion, and/or mutation of the gene of interest. In some embodiments, a phenotype of a condition (e.g., a disease or disorder) associated with fat metabolism can be induced by exposing the transgenic animal, or cells or tissues derived therefrom, to an agent that induces the condition. The condition-inducing agent can be a protein, a peptide, a nucleic acid, a drug, a small molecule, radiation, or any combinations thereof.

After feeding the transgenic animal described herein with a composition high in carbohydrates and/or saturated fat, various assays and/or analyses can be used to detect response(s) of the nonhuman transgenic animal described herein can be performed. For example, responses of the nonhuman transgenic animal can comprise expression level of an analyte associated with genomics, metabolomics, lipidomics, or proteomics.

By comparing the detected responses of the nonhuman transgenic animal to a control, an effect of n-6 fatty acid and/or n-3 fatty acid on the condition (e.g., disease or disorder) being studied can be determined. In some embodiments, the control can be a nonhuman transgenic animal described herein, or cells or tissues derived therefrom, that is/are fed a composition low in carbohydrates and/or saturated fat. In some embodiments, the control can be a nonhuman animal that cannot convert carbohydrates and/or saturated fat to n-6 fatty acids and/or n-3 fatty acids. In some embodiments, the control can be a wild type nonhuman animal.

Other features and advantages of the invention will be apparent from the following detailed description, the drawings, and the Examples.

BRIEF DESCRIPTION OF THE DRAWINGS

FIG. 1A is a roadmap for the conversion of essential fatty acids from non-essential nutrients in Omega mice. In mammals, carbohydrates can be converted to saturated fatty acids (SFA), and SFA can be converted into monounsaturated fatty acids (MUFA) by stearoyl-CoA desaturase-1 (SCD-1). Introduction of the fat-2 and fat-1 transgenes allows mammals to further convert MUFA into n-6 polyunsaturated fatty acids (PUFA), and n-6 PUFA into n-3 PUFA, respectively. FIG. 1B show fat-1 and fat-2 transgene expression in wild-type (WT), fat-2, and Omega mouse littermates by PCR. FIG. 1C are partial gas chromatograph traces showing the fatty acid profiles of total lipids extracted from skeletal muscles of a wild-type mouse (WT, upper panel), a fat-2 transgenic mouse (Fat-2, middle panel), and an Omega transgenic mouse (Omega, lower panel). All mice were 10-week-old males and fed with the same diet high in SFA and carbohydrates and low in n-6 PUFA. FIG. 1D is a bar graph showing quantification of PUFA from muscle tissue of WT, fat-2, and Omega mice (left panel) and comparison of the n-6/n-3 PUFA ratio among the phenotypes (right panel). For significance values of fatty acid profile in various tissues, refer to Table 1. Values expressed as mean±s.d. (n=3 per group; *P<0.05, P<0.01, *P<0.001).

FIG. 2A are images showing lipid accumulation as shown by oil red O staining. FIG. 2B is a bar graph showing measurement of total hepatic TG content (n=4; *P<0.05, *P<0.001). FIG. 2C** show hepatic expression of SCD-1, FASN, and ACC and GAPDH measured by PCR (left panel) and quantitative relative gene expression values to GAPDH (right panel) (n=3; *P<0.05, P<0.01, *P<0.001).

FIG. 3A shows a picture of representative plate cultures of *Escherichia coli* (left panel) and quantification of stool bacterial DNA by qPCR of Enterobacteriaceae (right panel). FIG. 3B shows a picture of representative plate cultures of *Bifidobacterium* (left panel) and quantification of stool bacterial DNA by qPCR of *Bifidobacterium* (right panel). Values expressed as mean±s.d. (n=5; *P<0.05, P<0.01, *P<0.001).

FIG. 4A shows plasma levels of key inflammatory cytokines measured via multiplex assay (n=5; *P<0.05, P<0.01). FIG. 4B** shows plasma levels of LPS measured via limulus amebocyte lysate assay (n=5; *P<0.05, **P<0.01).

DETAILED DESCRIPTION OF THE INVENTION

Figures 1A, 1B, 1C, 1D:
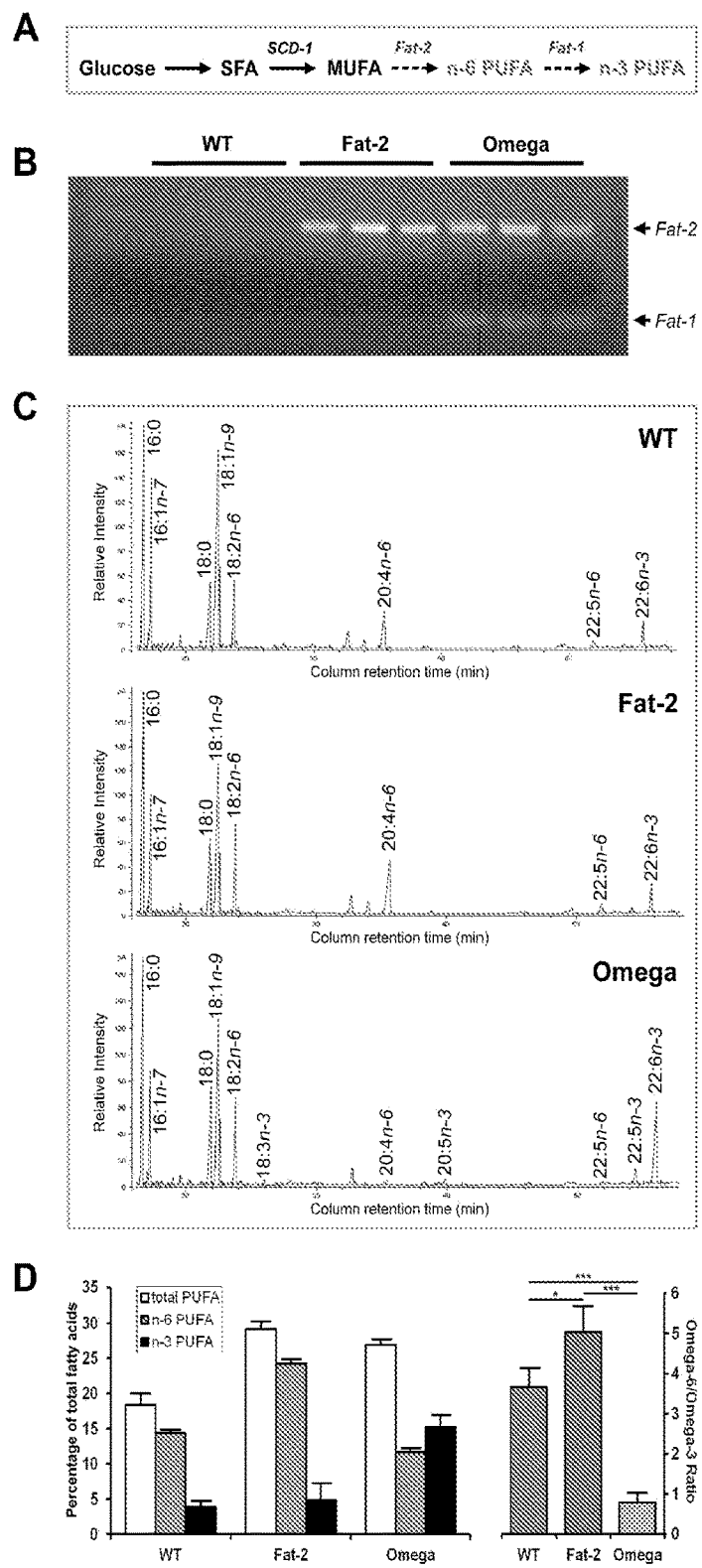
FIGS. 1A-1D show schematic generation of essential fatty acids and experimental data on genotyping, and phenotyping of the fat-2 and Omega transgenic mice.

Embodiments of various aspects described herein are, in part, based on the discovery that delta 12 fatty acid desaturase gene (fat-2) and n-3 fatty acid desaturase gene (fat-1) from low life form (e.g., roundworms) can be optimized and introduced into higher life form or genomically complex animal cells (e.g., mammalian cells) to generate a non-human animal that can produce essential n-6 and/or n-3 fatty acids from saturated fats and/or carbohydrates. In one aspect of the discovery, the inventors have successfully generated fat-2 transgenic mice that are capable of converting carbohydrates and/or saturated fat to n-6 fatty acids de novo or in vivo. In another aspect of the discovery, the inventors have also successfully engineered transgenic mice to carry both optimized fat-2 and fat-1 from roundworm *Caenorhabditis elegans* (*C. elegans*) such that the transgenic mice (referred to as "Omega mice" hereafter) can produce essential n-6 and n-3 fatty acids from saturated fats and/or carbohydrates. Further, the inventor has shown that Omega mice exhibited a balanced n-6/n-3 fatty acids ratio in body tissues. For example, when maintained on a high-fat diet lacking essential fatty acids or a high-carbohydrate, no-fat diet, the Omega mice exhibited high tissue levels of both n-6 and n-3 fatty acids, with a ratio of ~1:1. Furthermore, when the three genotypes—wild-type (incapable of producing essential fatty acids), fat-2 transgenic (producing only n-6 and no n-3 fatty acids), and Omega transgenic (producing both n-6 and n-3 fatty acids) mice—were fed the same diet, they presented distinct profiles of characteristics associated with many metabolic diseases (e.g., hepatic lipogenesis, gut microbiota, and low-grade inflammation). The discovery thus provides a novel transgenic non-human animal model that can endogenously synthesize essential n-6 and n-3 fatty acids, e.g., for addressing fat metabolism and disease, as well as an innovative technology for increased production of both n-6 and n-3 essential fatty acids.

Accordingly, some aspects described herein provide for compositions and methods for effectively modifying the contents of polyunsaturated fatty acids (PUFAs), e.g., n-6 and n-3 fatty acids, in animals or cells thereof (i.e., cells other than those of *C. elegans*, for example, but not limited to, mammalian cells). In some embodiments, an optimized fat-2 and/or fat-1 nucleic acid or amino acid sequence or a biologically active variant thereof can be operably linked to a regulatory sequence or a constitutively active or tissue-specific promoter. Regulatory sequences encompass not only promoters, but also enhancers or other expression control sequence, such as a polyadenylation signal, that facilitates expression of the nucleic acid. The engineered animal cells (e.g., in vitro, in vivo or ex vivo) that can produce n-6 and/or n-3 fatty acids from saturated fat and/or carbohydrates, transgenic non-human animals containing the cells, food products obtained from those transgenic non-human animals (e.g., meat or other edible parts of the animals (e.g., liver, kidney, or thymus), and methods of using the same are also described herein.

Nonhuman Transgenic Animals

Some aspects described herein relate to nonhuman transgenic animals that are capable of producing n-6 fatty acids from saturated fats, monounsaturated fats and/or carbohydrates. For example, in one aspect, described herein is a nonhuman transgenic animal having a genome comprising a first exogenous and/or heterologous nucleic acid molecule operably linked to a promoter, wherein the first exogenous and/or heterologous nucleic acid molecule comprises a nucleotide sequence encoding an enzyme that converts saturated fats, monounsaturated fats and/or carbohydrates to omega-6 (or n-6 fatty acids). Upon expression of the first exogenous and/or heterologous nucleic acid molecule within the transgenic animal, the transgenic animal produces omega-6 (or n-6 fatty acids) from saturated fats, monounsaturated fats and/or carbohydrates.

In some embodiments, the conversion efficiency of the heterologous enzyme converting saturated fats, monounsaturated fats and/or carbohydrates to n-6 fatty acids within the transgenic animal can be at least about 30% or more, including, e.g., at least about 40%, at least about 50%, at least about 60%, at least about 70%, at least about 80%, at least about 90%, at least about 95% or more. In some embodiments, the conversion efficiency of the heterologous enzyme converting saturated fats, monounsaturated fats and/or carbohydrates to n-6 fatty acids within the transgenic animal can be 100%.

As used herein, the term "saturated fats" refers to triglycerides containing substantial amounts of saturated fatty acids. In some embodiments, the saturated fats can comprise at least about 50% or more, including, e.g., at least about 60%, at least about 70%, at least about 80%, at least about 90%, at least about 95% or more, including up to 100% of the saturated fatty acids. In some embodiments, the saturated fats can contain less than 5% or lower (including, e.g., less than 4%, less than 3%, less than 2%, less than 1%, less than 0.5% or lower) polyunsaturated fatty acids. In some embodiments, the saturated fats do not contain any polyunsaturated fatty acids such as n-3 fatty acids and/or n-6 fatty acids. In some embodiments, the saturated fats can encompass monounsaturated fats, e.g., in no more than 50% of the total fatty acids. Generally, saturated fatty acids have no double bonds between the individual carbon atoms of the fatty acid chain. That is, the chain of carbon atoms is fully "saturated" with hydrogen atoms. There are many kinds of naturally occurring saturated fatty acids, which differ mainly in number of carbon atoms, for example, from 3 carbons (propionic acid) to 36 carbons (hexatriacontanoic acid). In some embodiments, saturated fats can have a carbon chain length between C8 and C22. Examples of saturated fatty acids include, but are not limited to, caprylic acid (C8), decanoic acid (C10), lauric acid (C12), myristic acid (C14), palmitic acid (C16), and a combination of two or more thereof. Examples of saturated fats include, but are not limited to coconut oil, safflower oil, sunflower oil, and tallow. Additional examples of saturated fatty acids include palmitate, stearate, and myristate, and acyclic, cyclic, heterocyclic, aromatic ester derivatives thereof containing one or more groups selected from hydroxy, acyloxy, aryloxy, amino, sulfhydryl, sulfonate, sulfate, phosphonate, phosphate, bis-, tris- and polyphosphonates and phosphates, phosphatidyl, nucleosides, oligosaccharides, polysaccharides, and polyols. Saturated fats can be solid or liquid at room temperature. Saturated fats can be naturally occurring or synthetic.

The term "unsaturated fatty acids" as used herein refers to triglycerides with at least one or more, including, e.g., at least two or more, double bonds along their carbon backbones. Unsaturated fatty acids can include monounsaturated fatty acids (or monounsaturated fats) or polyunsaturated fatty acids.

As used herein, the term "monounsaturated fats" refers to unsaturated fatty acids with only one "double bond" along the carbon backbone. In some embodiments, the double bond can be present between the $9^{th}$ and $10^{th}$ carbon atom as for palmitoleic acid (16:1) and oleic acid (18:1). Unsaturated fatty acids are generally fatty acids that have at least one or more double bonds along their carbon backbones. The structure of a fatty acid can be represented by a notation system of "X:Y", where X is the total number of carbon (C) atoms and Y is the number of double bonds.

As used herein, the term "polyunsaturated fatty acids" (or "PUFAs") refers to unsaturated fatty acids with at least two double bonds along the carbon backbone. By way of example only, the double bonds can be present between the 9th and 10th, and 12th and 13th carbon atoms for linoleic acid (18:2); or between the 9th and 10th, 12th and 13th, and 15th and 16th carbon atoms for α-linolenic acid (18:3).

"PUFAs" can be classified into two major families (depending on the position (n) of the first double bond nearest the methyl end of the fatty acid carbon chain). Fatty acids have two ends, the carboxylic acid (—COOH) end, which is generally considered the beginning of the chain, thus "alpha", and the methyl ($CH_3$) end, which is generally considered the "tail" of the chain, thus "omega." The way in which a fatty acid is named is determined by the location of the first double bond, counted from the methyl end, that is, the omega (ω-) or the n-end. Thus, the "n-6 fatty acids" or "omega-6 fatty acids" have the first unsaturated double bond starting at the sixth carbon atom from the omega (methyl) end of the molecule and additionally have one or more double bonds toward the carboxyl end of the molecule. Non-limiting examples of n-6 fatty acids include linoleic acid, gamma-linolenic acid, calendic acid, eicosadienoic acid, dihomo-gamma-linolenic acid, arachidonic acid, docosadienoic acid, adrenic acid, docosapentaenoic acid, tetracosatetraenoic acid, tetracosapentaenoic acid, and a combination of two or more thereof.

In contrast, the "n-3 fatty acids" or "omega-3 fatty acids" have the first unsaturated double bond starting at the third carbon atom away from the omega end of the molecule and additionally have one or more double bonds toward the carboxyl end of the molecule. Non-limiting examples of n-3 fatty acids include hexadecatrienoic acid, α-linolenic acid, stearidonic acid, eicosatrienoic acid, eicosatetraenoic acid, eicosapentaenoic acid, heneicosapentaenoic acid, docosapentaenoic acid, docosahexaenoic acid, tetracosapentaenoic acid, tetracosahexaenoic acid, and a combination of two or more thereof.

As used herein, the term "carbohydrates," also known as sugars or saccharides, refers to molecules comprising or consisting of carbon, hydrogen and oxygen having the general formula $C_x(H_2O)_y$. In some embodiments, x and y can be greater than or equal to 3. In some embodiments, x and y can be independently 3, 4, 5, 6, 7, 8, 9, 10 or more.

Integers x and y can be the same or different. Carbohydrates can include monosaccharides, dissacharides, polysaccharides, and mixtures thereof. The term "monosaccharide" or "monosaccharides" are generally hydroxy aldehydes or hydroxy ketones which cannot be hydrolyzed into any simpler carbohydrate. Examples of monosaccharides include, but are not limited to, hexose, dextrose, glucose, fructose and galactose. The term "disaccharides or "disaccharide" refers to two monosaccharides linked by a glycoside bond. Non-limiting examples of disaccharides include, but are not limited to sucrose, maltose, cellobiose, and lactose. The term "polysaccharide" or "polysaccharides" include those saccharides containing more than two monosaccharide units. An exemplary polysaccharide can include, but is not limited to, starch (e.g., corn starch). This term also includes oligosaccharides (e.g., but not limited to, fructo-oligosaccharides and mannan oligosaccharides). The carbohydrates can be naturally occurring or synthetic.

In some embodiments, upon expression of the first exogenous and/or heterologous nucleic acid molecule comprising a nucleotide sequence encoding an enzyme that converts saturated fats, monounsaturated fats and/or carbohydrates to omega-6 (or n-6 fatty acids), the content of n-6 fatty acids in the transgenic animal (e.g., within body tissue and/or cells) is increased, as compared to the n-6 fatty acid content in a wild-type or non-transgenic animal. In some embodiments, the increase in the n-6 fatty acids content can be at least about 30% or higher, including, at least about 40%, at least about 50%, at least about 60%, at least about 70%, at least about 80%, at least about 90%, at least about 95% or more, as compared to the n-6 fatty acid content in a non-transgenic or wild-type animal (e.g., an animal whose genome does not comprise the first exogenous and/or heterologous nucleic acid molecule encoding an enzyme that converts saturated fats and/or carbohydrates to n-6 fatty acids). In some embodiments, the increase in the n-6 fatty acids content can be at least about 1.1-fold or higher, including, at least about 2-fold, at least about 3-fold, at least about 4-fold, at least about 5-fold, at least about 6-fold, at least about 7-fold, at least about 8-fold, at least about 9-fold, at least about 10-fold or more, as compared to the n-6 fatty acid content in a non-transgenic or wild-type animal (e.g., an animal whose genome does not comprise the first exogenous and/or heterologous nucleic acid molecule encoding an enzyme that converts saturated fats and/or carbohydrates to n-6 fatty acids).

In some embodiments, the nucleotide sequence encoding an enzyme that converts saturated fats and/or carbohydrates to n-6 fatty acids can be derived from any species that is capable of synthesizing n-6 fatty acids from carbohydrates and/or saturated fat de novo or in vivo within a cell or animal. For example, an enzyme that converts saturated fat and/or carbohydrates to n-6 fatty acids can be derived from invertebrate animals, insects, worms, plants (e.g., peanuts, soybeans, rapeseeds, and flaxseeds), bacteria, fungus, fish, crustaceans, molluscs, nematodes, cyanobacteria, or algae.

By way of example only, in some embodiments, the enzyme that converts saturated fat and/or carbohydrates to n-6 fatty acids can comprise delta 12 fatty acid desaturase or a biologically active variant thereof. In one embodiment, the nucleotide sequence encoding a delta 12 fatty acid desaturase or a biologically active variant thereof can be derived from a worm. In one embodiment, the nucleotide sequence encoding a delta 12 fatty acid desaturase or a biologically active variant thereof can be derived from C. elegans. In one embodiment, the nucleotide sequence encoding a delta 12 fatty acid desaturase or a biologically active variant thereof can be derived from peanuts. Yu et al. J Genet Genomics. 2008; 35: 679-85. In another embodiment, the nucleotide sequence encoding a delta 12 fatty acid desaturase or a biologically active variant thereof can be derived from a fungus. Sakuradani et al. Eur J. Biochem. 1999; 261: 812-20.

As used herein and throughout the specification, the term "exogenous" refers to addition and/or incorporation of a nucleic acid sequence encoding a gene of interest that is not naturally present in a host to be made transgenic (e.g. nucleic acids encoding fat-2 and/or fat-1) in a genome of the host.

As used herein and throughout the specification, the term "heterologous" refers to a nucleic acid sequence of one species introduced into a cell or a host of a different species. The heterologous nucleic acid sequence is not normally or naturally expressed in the cell or host of a different species.

In some embodiments, the nucleotide sequence encoding an enzyme that converts saturated fat and/or carbohydrates to n-6 fatty acids (e.g., delta 12 fatty acid desaturase) can correspond to or be derived from the nucleotide sequence of a wild-type enzyme that converts saturated fats and/or carbohydrates to n-6 fatty acids (e.g., wild-type delta 12 fatty acid desaturase). In some embodiments, the wild-type delta 12 fatty acid desaturase can be encoded by wild-type fat-2 gene sequence. An exemplary wild-type fat-2 gene sequence derived from C. elegans is shown in SEQ ID NO. 5.

In some embodiments, the nucleotide sequence encoding an enzyme that converts saturated fat and/or carbohydrates to n-6 fatty acids (e.g., delta 12 fatty acid desaturase) can be a modified nucleotide sequence, as compared to the nucleotide sequence of the corresponding wild-type enzyme (e.g., delta 12 fatty acid desaturase). As used herein and throughout the specification, the term "modified" refers to a nucleotide sequence having about 1% or more (including, about 2%, about 3%, about 4%, about 5%, about 10%, about 20%, about 30%, about 40%, about 50%, about 60% or more) of the nucleotides different from a nucleotide sequence encoding a wild-type gene of interest (e.g., but not limited to, delta 12 fatty acid desaturase), and retaining enough of the biological activity of the wild-type gene of interest (e.g., but not limited to, delta 12 fatty acid desaturase). For example, to enable a higher expression of a heterologous gene in a host to be made transgenic, a nucleotide sequence encoding a heterologous gene can be modified by optimization of codon usage for the host cells. In some embodiments, a sequence is optimized for usage in host cells when one or more of the naturally occurring codons that encode the amino acid sequence are altered but still encode the same amino acid sequence. By way of example only, one or more of the codons represented as "GTT," which encodes the amino acid residue valine, can be replaced with CTG, which also encodes valine; one or more of the codons represented as "CGT," which encodes the amino acid residue arginine, can be replaced with CGC, which also encodes arginine; and so forth. The codons are modified to include codons that are preferred by the host into which the recombinant DNA is to be inserted. An optimized sequence can be incorporated in any of the vectors and cells described herein, and used in any of the methods in which a wild-type sequence (e.g., a fat-2 gene and/or fat-1 gene as described below) can be used. In some instances (e.g., in the production of transgenic animals), the use of a codon-optimized sequence may be desirable, e.g., to increase the expression of the heterologous gene introduced into the transgenic animal. Optimization is not the only way in which the nucleic acid sequences can be modified.

The sequence encoding the delta 12 fatty acid desaturase can include at least one optimized codon. The number of codons that are optimized can vary. In some embodiments, the number is sufficient to improve some aspect of expression (e.g., the number of copies transcribed) or to otherwise enhance the utility of the sequence. In some embodiments, modifying only a few codons (e.g., 1-5) can improve the sequence. In other embodiments, a larger number of codons (e.g., at least 5 and up to 150) can be optimized. In some embodiments, and regardless of the original species of the delta 12 fatty acid desaturase-encoding sequence, a nucleic acid molecule can include 5-10, 10-15, 15-20, 20-25, 25-30, 30-35, 35-40, 40-45, 45-50, 50-55, 55-60, 60-65, 65-70, 70-75, 75-80, 80-85, 85-90, 90-95, 95-100, 100-105, 105-110, 110-115, 115-120, 120-125, 125-130, 130-135, 135-140, 140-145, 145-150, 10-125, 25-100, 30-90, 40-80, 50-70, or about 60 optimized codons.

Moreover, the positions of the optimized codons can vary. For example, with respect to the *C. elegans* fat-2 gene (e.g., as shown in SEQ ID NO. 6 where ATG is codon 1), an optimized codon can be found at one or more (e.g., at least 1, at least 2, at least 3, at least 4, at least 5, at least 6, at least 7, at least 8, at least 9, at least 10, at least 20, at least 30, at least 40, at least 50, at least 60, at least 70, at least 80, at least 90, at least 95, or more, including all) of positions 4, 12, 14, 16, 19, 22, 24, 30, 38, 41, 44, 48, 53, 56, 59, 63, 65, 74, 76, 80, 85, 92, 93, 95, 97, 109, 111, 113, 114, 117, 119, 121, 124, 126, 127, 129, 130, 131, 133, 134, 145, 146, 156, 157, 168, 161, 164, 169, 172, 176, 183, 184, 186, 188, 191, 199, 209, 215, 221, 238, 241, 242, 243, 244, 249, 253, 263, 267, 271, 272, 274, 275, 278, 281, 284, 306, 307, 315, 316, 320, 321, 323, 328, 333, 337, 342, 344, 348, 352, 354, 355, 360, 362, 364, 366, 375, 376, and 377. Where desaturase-encoding genes other than the *C. elegans* fat-2 gene are used, codons can be optimized at one or more (e.g., at least 1, at least 2, at least 3, at least 4, at least 5, at least 6, at least 7, at least 8, at least 9, at least 10, at least 20, at least 30, at least 40, at least 50, at least 60, at least 70, at least 80, at least 90, at least 95, or more, including all) of these same positions. In homologous genes (e.g., a delta-12 desaturase gene of a plant or fungus), the positions optimized can be those corresponding to one or more (e.g., at least 1, at least 2, at least 3, at least 4, at least 5, at least 6, at least 7, at least 8, at least 9, at least 10, at least 20, at least 30, at least 40, at least 50, at least 60, at least 70, at least 80, at least 90, at least 95, or more, including all) of the positions listed above.

In some embodiments, the optimized sequence can have a similarity of at least about 70% or more (including, e.g., at least about 80%, at least about 90%, at least about 95% or more) to the wild-type sequence (e.g., *C. elegans* fat-2 gene). In some embodiments, the optimized sequence can have a similarity of about 80% or more to the wild-type sequence (e.g., *C. elegans* fat-2 gene). In some embodiments, the optimized sequence can have a similarity of about 90% or more to the wild-type sequence (e.g., *C. elegans* fat-2 gene). In some embodiments, the optimized sequence can have a similarity of about 91% or more to the wild-type sequence (e.g., *C. elegans* fat-2 gene).

In some embodiments, to enhance the expression of the *C. elegans* fat-2 gene in mammals, the codon of the *C. elegans* fat-2 gene sequence can be optimized based on the mammalian desaturase sequence. In one embodiment, the optimized nucleotide sequence of fat-2 is shown in SEQ ID NO. 1, with its corresponding amino acid sequence shown in SEQ ID NO. 3.

In some embodiments, the nucleotide sequence encoding an enzyme that converts saturated fats and/or carbohydrates to n-6 fatty acids can correspond to or be derived from the nucleotide sequence of delta-12 desaturase. In some embodiments, the delta-12 desaturase can be derived from *Spinacia oleracea*. In one embodiment, the delta-12 desaturase can be encoded by *Spinacia oleracea* FAD2 mRNA sequence as shown in SEQ ID NO. 7.

The first exogenous and/or heterologous nucleic acid molecule can comprise a nucleotide sequence encoding delta 12 fatty acid desaturase or a biologically active variant thereof. The term "biologically active variant" refers to an entity which possesses a biological activity (either functional or structural) that is substantially similar to a biological activity of the entity or molecule it is a functional derivative of. The term "biologically active variant" is intended to include the "fragments," "variants," "analogs," or "chemical derivatives" of a molecule. A "fragment" of a molecule, is meant to refer to any polypeptide subset of the molecule. Fragments of, for example a delta 12 fatty acid desaturase, which have the activity as a wild-type delta 12 fatty acid desaturase to convert saturated fats and/or carbohydrates to n-6 fatty acids are also encompassed for use in various aspects described herein. A "variant" of a molecule, for example a delta 12 fatty acid desaturase, is meant to refer to a molecule substantially similar in structure and function to either the entire molecule, or to a fragment thereof. A molecule is said to be "substantially similar" to another molecule if both molecules have substantially similar structures and/or if both molecules possess a similar biological activity. Thus, provided that two molecules possess a similar activity, they are considered variants as that term is used herein even if the structure of one of the molecules not found in the other, or if the sequence of amino acid residues or nucleotide sequence is not identical. An "analog" of a molecule, for example an analogue of a delta 12 fatty acid desaturase, is meant to refer to a molecule substantially similar in function to either the entire molecule or to a fragment thereof. As used herein, a molecule is said to be a "chemical derivative" of another molecule when it contains additional chemical moieties not normally a part of the molecule. Such moieties can improve the molecule's expression levels, enzymatic activity, solubility, absorption, biological half-life, etc. The moieties can alternatively decrease the toxicity of the molecule, eliminate or attenuate any undesirable side effect of the molecule, etc. Moieties capable of mediating such effects are disclosed in Remington's Pharmaceutical Sciences, 18th edition, A. R. Gennaro, Ed., MackPubl., Easton, Pa. (1990).

In some embodiments, a biologically active variant of the delta 12 fatty acid desaturase can be a variant that retains sufficient biological activity of a wild-type or modified delta 12 fatty acid desaturase described herein (e.g., encoded by SEQ ID NO. 1) to convert carbohydrates and/or saturated fats to n-6 fatty acids. In some embodiments, a biologically active variant of the delta 12 fatty acid desaturase can be a variant that retains sufficient biological activity of a wild-type or modified delta 12 fatty acid desaturase to be therapeutically or clinically effective (e.g., a variant that is useful producing transgenic animals, in treating subjects, or conducting diagnostic or other laboratory tests or assays). For example, biologically active variants of delta 12 fatty acid desaturase can include mutants or fragments of that enzyme that retain at least about 25% or higher (including, e.g., at least about 30%, at least about 40%, at least about 50%, at least about 60%, at least about 70%, at least about 80%, at least about 90%, at least about 95%, at least about 98%, at least about 99% or more) of the biological activity of a wild-type or modified delta 12 fatty acid desaturase (e.g., encoded by SEQ ID NO. 1) to convert carbohydrates and/or saturated fats to n-6 fatty acids. For example, a fragment of a delta 12 fatty acid desaturase enzyme is a biologically active variant of the full-length enzyme when the fragment is capable of converting carbohydrates and/or saturated fats to n-6 fatty acids, and the conversion is at least about 25% or higher (including, e.g., at least about 30%, at least about 40%, at least about 50%, at least about 60%, at least about 70%, at least about 80%, at least about 90%, at least about 95%, at least about 98%, at least about 99% and up to 100%) as efficient as the wild-type or modified enzyme does so under the same conditions.

The biologically active variants of a delta 12 fatty acid desaturase can also contain one or more amino acid substitutions (e.g., 1%, 5%, 10%, 20%, 25%, 30%, 40%, 50%, 60% or more of the amino acid residues in the enzyme sequence can be replaced with another amino acid residue). These substitutions can constitute conservative amino acid substitutions, which are known in the art.

In some embodiments, the biologically active variants of a delta 12 fatty acid desaturase can be at least about 50% or higher (including, e.g., at least about 60%, at least about 70%, at least about 80%, at least about 90%, at least about 95%, at least about 99%) identical to the nucleotide sequence of the wild-type or modified delta 12 fatty acid desaturase (e.g., as encoded by SEQ ID NO. 1). In some embodiments, the biologically active variants of a delta 12 fatty acid desaturase can be at least about 70% identical to the nucleotide sequence of the wild-type or modified delta 12 fatty acid desaturase (e.g., as encoded by SEQ ID NO. 1). In some embodiments, the biologically active variants of a delta 12 fatty acid desaturase can be at least about 90% identical to the nucleotide sequence of the wild-type or modified delta 12 fatty acid desaturase (e.g., as encoded by SEQ ID NO. 1). In some embodiments, the biologically active variants of a delta 12 fatty acid desaturase can be at least about 95% identical to the nucleotide sequence of the wild-type or modified delta 12 fatty acid desaturase (e.g., as encoded by SEQ ID NO. 1). In some embodiments, the biologically active variants of a delta 12 fatty acid desaturase can be at least about 99% identical to the nucleotide sequence of the wild-type or modified delta 12 fatty acid desaturase (e.g., as encoded by SEQ ID NO. 1).

The biological activity of the biologically active variants of a delta 12 fatty acid desaturase (e.g., fat-2) can be evaluated upon expression in a cell or an animal, e.g., by RNA analysis, and/or enzymatic assays, and/or by lipid analysis of the fatty acid composition of the cell or animal. Methods for determining the fatty acid composition of the cell or animal are known in the art. An exemplary method to perform fatty acid composition analysis is using gas chromatography, which is described in Kang et al., BMC Biochem 2005; 6:5, and in U.S. Pat. No. 7,238,851, the content of which is incorporated herein by reference.

Since functional delta 12 fatty acid desaturase (e.g., encoded by fat-2 gene or a biologically active variant thereof) can convert carbohydrates and/or saturated fats to n-6 fatty acids, the n-6 fatty acid content of the transgenic animal carrying heterologous delta 12 fatty acid desaturase enzyme (e.g., encoded by fat-2 gene or a biologically active variant thereof) or cells derived therefrom generally increases when the transgenic animal or cells derived therefrom are fed with a composition comprising carbohydrates and/or saturated fats. For example, a transgenic animal with a heterologous expression of delta 12 fatty acid desaturase enzyme (e.g., encoded by fat-2 gene or a biologically active variant thereof) can display an increase in n-6 fatty acid content in a body tissue and/or cells by at least 30% or more, including, e.g., at least 40%, at least 50%, at least 60%, at least 70%, at least 80%, at least 90%, at least 95% or more, as compared to an animal without the transgene (control), when the transgenic animal and the control are both fed with the same composition comprising carbohydrates and/or saturated fats. In some embodiments, a transgenic animal with a heterologous expression of delta 12 fatty acid desaturase enzyme (e.g., encoded by fat-2 gene or a biologically active variant thereof) can display an increase in n-6 fatty acid content in a body tissue and/or cells by at least 1.1-fold or more, including, e.g., at least 1.5-fold, at least 2-fold, at least 3-fold, at least 4-fold, at least 5-fold, at least 6-fold, or more, as compared to an animal without the transgene (control), when the transgenic animal and the control are both fed with the same composition comprising carbohydrates and/or saturated fats.

In some embodiments, the ratio of n-6 fatty acid(s) to n-3 fatty acid(s) in a transgenic animal with a heterologous expression of delta 12 fatty acid desaturase enzyme (e.g., encoded by fat-2 gene or a biologically active variant thereof) can be greater than 1:1 or higher, upon expression of the first exogenous and/or heterologous nucleic acid molecules in the transgenic animal. For example, the ratio of n-6 fatty acid(s) to n-3 fatty acid(s) in the transgenic animal can be greater than 1.5:1, greater than 2:1, greater than 5:1, greater than 10:1, greater than 15:1 or greater than 20:1 or higher.

In some embodiments, the genome of a nonhuman transgenic animal can further comprise a second exogenous and/or heterologous nucleic acid molecule. The second exogenous and/or heterologous nucleic acid molecule can comprise a nucleotide sequence encoding a gene that is associated with metabolism of saturated fats and/or carbohydrates. Examples of genes associated with metabolism of saturated fats and/or carbohydrates include, but are not limited to n-3 fatty acid desaturase, fatty acid synthase (FAS), and stearoyl-CoA desaturase-1 (SCD-1), and a combination of two or more thereof.

In some embodiments, the second exogenous and/or heterologous nucleic acid molecule can comprise a nucleotide sequence encoding an enzyme that converts at least one or more n-6 fatty acids to one or more n-3 fatty acids.

In some embodiments, the conversion efficiency of the heterologous enzyme converting at least one or more n-6 fatty acids to one or more n-3 fatty acids within the transgenic animal can be at least about 30% or more, including, e.g., at least about 40%, at least about 50%, at least about 60%, at least about 70%, at least about 80%, at least about 90%, at least about 95% or more. In some embodiments, the conversion efficiency of the heterologous enzyme converting saturated fats, monounsaturated fats and/or carbohydrates to n-6 fatty acids within the transgenic animal can be 100%. Accordingly, upon expression of the first and second exogenous and/or heterologous nucleic acid molecules in the transgenic animal, the transgenic animal is capable of producing n-3 fatty acids and n-6 fatty acids (at least some or all of which can be converted to n-3 fatty acids) from saturated fats and/or carbohydrates.

In some embodiments, upon expression of the second exogenous and/or heterologous nucleic acid molecule comprising a nucleotide sequence encoding an enzyme that converts at least one n-6 fatty acid to one or more n-3 fatty acids, the content of n-3 fatty acid(s) in the transgenic animal (e.g., within body tissue and/or cells) is increased, as compared to the n-3 fatty acid content in an animal of the same species without the second exogenous and/or heterologous nucleic acid molecule (e.g., a wild-type animal or a transgenic animal with a heterologous expression of the first exogenous nucleic acid molecule described herein). In some embodiments, the increase in the n-3 fatty acids content can be at least about 30% or higher, including, at least about 40%, at least about 50%, at least about 60%, at least about 70%, at least about 80%, at least about 90%, at least about 95% or more, as compared to the n-3 fatty acid content in an animal of the same species without the second exogenous and/or heterologous nucleic acid molecule (e.g., a wild-type animal or a transgenic animal with a heterologous expression of the first exogenous nucleic acid molecule described herein). In some embodiments, the increase in the n-3 fatty acids content can be at least about 1.1-fold or higher, including, at least about 2-fold, at least about 3-fold, at least about 4-fold, at least about 5-fold, at least about 6-fold, at least about 7-fold, at least about 8-fold, at least about 9-fold, at least about 10-fold or more, as compared to the n-3 fatty acid content in an animal of the same species without the second exogenous and/or heterologous nucleic acid molecule (e.g., a wild-type animal or a transgenic animal with a heterologous expression of the first exogenous nucleic acid molecule described herein).

Accordingly, another aspect described herein provides a nonhuman transgenic animal that is capable of producing n-3 fatty acids from saturated fats and/or carbohydrates. In this aspect, a nonhuman transgenic animal can have a genome comprising (i) a first exogenous and/or heterologous nucleic acid molecule encoding an enzyme that converts saturated fats and/or carbohydrates to n-6 fatty acids (e.g., as encoded by a fat-2 gene sequence or a biologically active variant thereof); and (ii) a second exogenous and/or heterologous nucleic acid molecule comprising a nucleotide sequence that encodes an enzyme for converting an n-6 fatty acid to an n-3 fatty acid. Upon expression of the first and second exogenous and/or heterologous nucleic acid molecules within the transgenic animal, the transgenic animal can produce n-3 fatty acids and optionally n-6 fatty acids (at least some or all of which can be converted to n-3 fatty acids) from saturated fats and/or carbohydrates.

In some embodiments, the enzyme that converts an n-6 fatty acid to an n-3 fatty acid can comprise an n-3 fatty acid desaturase or a biologically active variant thereof. Upon expression of the second exogenous and/or heterologous nucleic acid molecule enables the transgenic animal to convert n-6 fatty acid to n-3 fatty acid. The International Patent Application No. WO 2005/077022 and the U.S. Pat. No. 7,238,851, the contents of each of which are incorporated by reference, describe transgenic animals that can convert n-6 fatty acids to n-3 fatty acids, compositions and method of making the same, as well as uses of the same, which can be used herein for the purposes of various aspects described herein.

In some embodiments, the nucleotide sequence encoding an n-3 fatty acid desaturase can be derived from any species that can synthesize n-3 fatty acid(s) from n-6 fatty acid(s) de novo or in vivo within the cell or animal. For example, an n-3 fatty acid desaturase can be derived from invertebrate animals, insects, worms, plants (e.g., peanuts, soybeans, rapeseeds, flaxseeds), bacteria, fungus, fish, crustaceans, molluscs, a nematode, cyanobacteria, or algae.

By way of example only, in one embodiment, the nucleotide sequence encoding an n-3 fatty acid desaturase can be derived from a worm. In one embodiment, the nucleotide sequence encoding an n-3 fatty acid desaturase can be derived from *C. elegans*.

In some embodiments, the nucleotide sequence encoding an n-3 fatty acid desaturase can correspond to or be derived from the nucleotide sequence of a wild-type n-3 fatty acid desaturase. In some embodiments, the wild-type n-3 fatty acid desaturase can be encoded by wild-type fat-1 gene sequence. An exemplary wild-type fat-1 gene sequence derived from *C. elegans* is shown in SEQ ID NO. 8.

In some embodiments, the nucleotide sequence encoding an n-3 fatty acid desaturase can be a modified nucleotide sequence, as compared to the nucleotide sequence of the corresponding wild-type enzyme. For example, a modified n-3 fatty acid desaturase is a nucleotide sequence having about 1% or more (including, about 2%, about 3%, about 4%, about 5%, about 10%, about 20%, about 30%, about 40%, about 50%, about 60% or more) of the nucleotides different from a nucleotide sequence encoding a wild-type n-3 fatty acid desaturase, and retaining enough of the biological activity of a wild-type n-3 fatty acid desaturase. As discussed above, to enable the higher expression of a heterologous gene in a host to be made transgenic, the codon of the nucleotide sequence can be, for example, optimized for the host cells. Thus, the sequence encoding the n-3 fatty acid desaturase can include at least one or more optimized codons. The number of codons that are optimized can vary. In some embodiments, the number is sufficient to improve some aspect of expression (e.g., the number of copies transcribed) or to otherwise enhance the utility of the sequence. In some embodiments, modifying only a few codons (e.g., 1-5) can improve the sequence. In other embodiments, a larger number of codons (e.g., at least 5 and up to 150) can be optimized. In some embodiments, and regardless of the original species of the n-3 fatty acid desaturase-encoding sequence, a second exogenous and/or heterologous nucleic acid molecule can include 5-10, 10-15, 15-20, 20-25, 25-30, 30-35, 35-40, 40-45, 45-50, 50-55, 55-60, 60-65, 65-70, 70-75, 75-80, 80-85, 85-90, 90-95, 95-100, 100-105, 105-110, 110-115, 115-120, 120-125, 125-130, 130-135, 135-140, 140-145, 145-150, 10-125, 25-100, 30-90, 40-80, 50-70, or about 60 optimized codons.

Moreover, the positions of the optimized codons can vary. For example, with respect to the *C. elegans* fat-1 gene (e.g., as shown in SEQ ID NO. 8 where ATG is codon 1), an optimized codon can be found at one or more (e.g., at least 1, at least 2, at least 3, at least 4, at least 5, at least 6, at least 7, at least 8, at least 9, at least 10, at least 20, at least 30, at least 40, at least 50, at least 60, at least 70, at least 80, or more, including all) of positions 6, 9, 18, 20, 22, 24, 28-30, 33-36, 47, 49, 52, 54, 58, 60, 61, 64, 67, 69-71, 73, 77, 79, 81, 86, 89, 92, 94-95, 100, 101, 105, 106, 112, 115, 118, 124, 127, 128, 131, 146, 151, 154, 161, 163, 164, 169, 178, 187, 188, 195, 197, 200, 202, 206, 210, 214, 217, 221, 223, 225, 227, 228, 232, 234, 241, 245, 255, 271, 280-282, 284, 285, 301, 303, 310, 312, 327, 362, and 370. Where desaturase-encoding genes other than the *C. elegans* fat-1 gene are used, codons can be optimized at one or more (e.g., at least 1, at least 2, at least 3, at least 4, at least 5, at least 6, at least 7, at least 8, at least 9, at least 10, at least 20, at least 30, at least 40, at least 50, at least 60, at least 70, at least 80, or more, including all) of these same positions. In homologous genes (e.g., an n-3 desaturase gene of a plant or fungus), the positions optimized can be those corresponding to one or more (e.g., at least 1, at least 2, at least 3, at least 4, at least 5, at least 6, at least 7, at least 8, at least 9, at least 10, at least 20, at least 30, at least 40, at least 50, at least 60, at least 70, at least 80, or more, including all) of the positions listed above.

In some embodiments, the optimized sequence can have a similarity of at least about 70% or more (including, e.g., at least about 80%, at least about 90%, at least about 95% or more) to the wild-type sequence (e.g., *C. elegans* fat-1 gene). In some embodiments, the optimized sequence can have a similarity of about 80% or more to the wild-type sequence (e.g., *C. elegans* fat-1 gene). In some embodiments, the optimized sequence can have a similarity of about 90% or more to the wild-type sequence (e.g., *C. elegans* fat-1 gene). In some embodiments, the optimized sequence can have a similarity of about 91% or more to the wild-type sequence (e.g., *C. elegans* fat-1 gene).

In some embodiments, to enhance the expression of the *C. elegans* fat-1 gene in mammals, the codon of the *C. elegans* fat-1 gene sequence can be optimized based on the mammalian desaturase sequence. In one embodiment, the optimized nucleotide sequence of fat-1 is shown in SEQ ID NO. 2, with its corresponding amino acid sequence shown in SEQ ID NO. 4.

The second exogenous and/or heterologous nucleic acid molecule can comprise a nucleotide sequence encoding n-3 fatty acid desaturase or a biologically active variant thereof. The term "biologically active variant" is same as defined above, and is intended to include fragments, variants, analogs, or chemical derivatives of a molecule, e.g., in the context of an n-3 fatty desaturase In some embodiments, a biologically active variant of the n-3 fatty acid desaturase can be a variant that retains sufficient biological activity of a wild-type or modified n-3 fatty acid desaturase described herein (e.g., as encoded by SEQ ID NO. 2) to convert at least one n-6 fatty acid to one or more n-3 fatty acids. In some embodiments, a biologically active variant of the n-3 fatty acid desaturase can be a variant that retains sufficient biological activity of a wild-type or modified n-3 fatty acid desaturase to be therapeutically or clinically effective (e.g., a variant that is useful in producing transgenic animals, treating patients, or conducting diagnostic or other laboratory tests or assays). For example, biologically active variants of n-3 fatty acid desaturase can include mutants or fragments of that enzyme that retain at least about 25% or higher (including, e.g., at least about 30%, at least about 40%, at least about 50%, at least about 60%, at least about 70%, at least about 80%, at least about 90%, at least about 95%, at least about 98%, at least about 99% and up to 100%) of the biological activity of a wild-type or modified n-3 fatty acid desaturase (e.g., as encoded by SEQ ID NO. 2) to convert at least one n-6 fatty acid to one or more n-3 fatty acids. For example, a fragment of an n-3 fatty acid desaturase enzyme is a biologically active variant of the full-length enzyme when the fragment converts at least one n-6 fatty acids to one or more n-3 fatty acids, and the conversion is at least about 25% or higher (including, e.g., at least about 30%, at least about 40%, at least about 50%, at least about 60%, at least about 70%, at least about 80%, at least about 90%, at least about 95%, at least about 98%, at least about 99% and up to 100%) as efficient as the wild-type or modified enzyme does so under the same conditions.

The biologically active variants of an n-3 fatty acid desaturase can also contain one or more amino acid substitutions (e.g., 1%, 5%, 10%, 20%, 25%, 30%, 40%, 50%, 60% or more of the amino acid residues in the enzyme sequence can be replaced with another amino acid residue). These substitutions can constitute conservative amino acid substitutions, which are known in the art.

In some embodiments, the biologically active variants of an n-3 fatty acid desaturase can be at least about 50% or higher (including, e.g., at least about 60%, at least about 70%, at least about 80%, at least about 90%, at least about 95%, at least about 99%) identical to the nucleotide sequence of the wild-type or modified n-3 fatty acid desaturase (e.g., as encoded by SEQ ID NO. 2). In some embodiments, the biologically active variants of an n-3 fatty acid desaturase is at least about 70% identical to the nucleotide sequence of the wild-type or modified n-3 fatty acid desaturase (e.g., as encoded by SEQ ID NO. 2). In some embodiments, the biologically active variants of an n-3 fatty acid desaturase is at least about 90% identical to the nucleotide sequence of the wild-type or modified n-3 fatty acid desaturase (e.g., as encoded by SEQ ID NO. 2). In some embodiments, the biologically active variants of an n-3 fatty acid desaturase is at least about 95% identical to the nucleotide sequence of the wild-type or modified n-3 fatty acid desaturase (e.g., as encoded by SEQ ID NO. 2). In some embodiments, the biologically active variants of an n-3 fatty acid desaturase is at least about 99% identical to the nucleotide sequence of the wild-type or modified n-3 fatty acid desaturase (e.g., as encoded by SEQ ID NO. 2).

Similar to fat-2, the biological activity of the biologically active variants of an n-3 fatty acid desaturase (e.g., fat-1) can be evaluated upon expression in a cell or an animal, e.g., by RNA expression and/or enzymatic assays and/or by lipid analysis of the fatty acid composition of the cell or animal using any methods known in the art or as described above.

Since functional n-3 fatty acid desaturase (e.g., encoded by fat-1 gene or a biologically active variant thereof) can convert at least one n-6 fatty acids to one or more n-3 fatty acids, the n-3 fatty acid content of the transgenic animal carrying both heterologous delta 12 fatty acid desaturase enzyme (e.g., encoded by fat-2 gene) and heterologous n-3 fatty acid desaturase (e.g., encoded by fat-1 gene or a biologically active variant thereof) or cells derived therefrom generally increases when the transgenic animal or cells derived therefrom are fed with a composition comprising carbohydrates and/or saturated fats. For example, a transgenic animal with a heterologous expression of n-3 fatty acid desaturase (e.g., encoded by fat-1 gene or a biologically active variant thereof) and delta 12 fatty acid desaturase (e.g., encoded by fat-2 gene or a biologically active variant thereof) can display an increase in n-3 fatty acid content in a body tissue and/or cells by at least 30% or more, including, e.g., at least 40%, at least 50%, at least 60%, at least 70%, at least 80%, at least 90%, at least 95% or more, as compared to an animal without the n-3 fatty acid desaturase transgene (control), when the transgenic animal and the control are both fed with the same composition comprising carbohydrates and/or saturated fats. In some embodiments, a transgenic animal with a heterologous expression of n-3 fatty acid desaturase (e.g., encoded by fat-1 gene or a biologically active variant thereof) and delta 12 fatty acid desaturase (e.g., encoded by fat-2 gene or a biologically active variant thereof) can display an increase in n-3 fatty acids in a body tissue, and/or cells by at least 1.1-fold or more, including, e.g., at least 1.5-fold, at least 2-fold, at least 3-fold, at least 4-fold, at least 5-fold, at least 6-fold, or more, as compared to an animal without the n-3 fatty acid desaturase transgene (control), when the transgenic animal and the control are both fed with the same composition comprising carbohydrates and/or saturated fats.

In some embodiments, the ratio of n-6 fatty acid(s) to n-3 fatty acid(s) in a transgenic animal with heterologous expressions of both n-3 fatty acid desaturase (e.g., encoded by fat-1 gene or a biologically active variant thereof) and delta 12 fatty acid desaturase (e.g., encoded by fat-2 or a biologically active variant thereof) can be lower than 2:1 or less, upon heterologous expression of the first and second exogenous and/or heterologous nucleic acid molecules in the transgenic animal. For example, the ratio of n-6 fatty acid(s) to n-3 fatty acid(s) in the transgenic animal can be less than 1:1 or lower. In some embodiments, the ratio of n-6 fatty acid(s) to n-3 fatty acid(s) in the transgenic animal can be less than 0.9:1, less than 0.8:1, less than 0.7:1, less than 0.6:1, less than 0.5:1, less than 0.4:1 or lower.

As used herein and throughout the specification, the term "transgenic animal" refers to an animal having in some or all of its cells a transgene, which has been introduced into the transgenic animal or an ancestor of the transgenic animal by way of human intervention, such as by the methods described below. For example, a transgene can be introduced into one or more cells of the transgenic animal at a prenatal stage, e.g., an embryonic stage. A "transgene" is a DNA sequence that is integrated into the genome of a host cell from which a transgenic animal develops. The transgene generally comprises a "gene of interest." A "gene of interest" is a nucleic acid sequence that encodes a protein or other molecule (e.g., an enzyme) that is desirable for integration and/or expression in a host cell. For example, in the context of various aspects described herein, the gene of interest include, e.g., delta 12 fatty acid desaturase, n-3 fatty acid desaturase, and/or biologically active variants thereof.

The "animal" to be made transgenic refers to an animal that cannot produce n-6 fatty acids and/or n-3 fatty acids de novo or in vivo in its body, or an animal that do not produce sufficient amount of n-6 and/or n-3 fatty acids de novo in its body for desirable or beneficial effect (e.g., nutritious values or therapeutic effects). In some embodiments, the transgenic animal to be made transgenic is an animal other than *C. elegans*. For example, animals to be made transgenic can include, but are not limited to, any animal kept as livestock or used as a food source (e.g., fish or other aquatic animals (e.g., squid, octopi, crustaceans (e.g., lobsters, crabs, snails, and shrimp), or other edible, water-living animals (e.g., eels). As shown in the Examples, a *C. elegans* fat-2 gene and/or fat-1 gene can be efficiently expressed when delivered to an animal cell, this gene, variants thereof, and other fat-1 genes can be used to generate transgenic mice or larger transgenic animals (such as cows, pigs, sheep, deer, goats, rabbits or any other livestock or domesticated animal; any edible bird (e.g., chicken, turkey, goose, duck, or game hen), and fish including shellfish and crustaceans) according to methods well known in the art. In some embodiment, the animal is a non-human.

In some embodiments of various aspects described herein, the nonhuman transgenic animal can be a transgenic fish. For example, the transgene can include a fat-2 gene or a biologically active variant thereof (e.g., a *C. elegans* fat-2 gene, which may include at least one optimized codon described herein) or both fat-2 and fat-1 genes or biologically active variants thereof (e.g., *C. elegans* fat-2 gene, which may include at least one optimized codon described herein, and *C. elegans* fat-1 gene, which may also include at least one optimized codon described herein). Examples of transgenic fish include, without limitations, cod (or any fish of the family Gadidae, order Gadiformes (e.g., haddock); halibut (the common name for either of two species of flat fish of the genus Hippoglossus); herring (the common name for several fishes of the order Clupeiformes, which also includes the anchovies); mackerel (the common name for a variety of species of imported food fishes in the family Scombridae); salmon (or any fish of the Salmonidae family, including trout); perch (or any fish of the family Percidae); shad (or any fish of the family Clupeidae); skate (or any fish of the family Rajidae); smelt (or any fish of the family Osmeridae); sole (or any fish of the family Soleidae); tuna (or any fish of the family Scombridae); and zebrafish.

In some embodiments, a transgenic fish can have a genome comprising a first exogenous and/or heterologous nucleic acid molecule operably linked to a promoter, wherein the first exogenous and/or heterologous nucleic acid molecule comprises (i) a nucleotide sequence of SEQ ID NO. 1 or (ii) a nucleotide sequence that is a biologically active variant of SEQ ID NO. 1 and is at least about 70% identical to SEQ ID NO. 1, wherein upon expression of the first exogenous and/or heterologous nucleic acid molecule in the transgenic fish, the transgenic fish produces n-6 from saturated fats and/or carbohydrates. In some embodiments, the genome of the transgenic fish can further comprise a second exogenous and/or heterologous nucleic acid molecule, wherein the second exogenous and/or heterologous nucleic acid molecule comprises a nucleotide sequence encoding an enzyme that converts at least one n-6 fatty acid to one or more n-3 fatty acids. Upon expression of the first and second exogenous and/or heterologous nucleic acid molecules in the transgenic fish, the transgenic fish produces n-3 and optionally n-6 from saturated fats and/or carbohydrates. In some embodiments, the nucleotide sequence encoding the enzyme that converts at least one n-6 fatty acid to one or more n-3 fatty acids can be a nucleotide sequence of SEQ ID NO. 2 or (ii) a nucleotide sequence that is a biologically active variant of SEQ ID NO. 2 and is at least about 70% identical to SEQ ID NO. 2.

In some embodiments of various aspects described herein, the nonhuman transgenic animal can be a vertebrate. In some embodiments, the nonhuman transgenic animal can be a mammal. In some embodiments, the mammal is a non-human mammal. In some embodiments, the nonhuman transgenic animal can be selected from the group consisting of a cow, a mouse, a rat, a pig, a sheep, a goat, deer, a rabbit, a buffalo, a fish, a poultry, a livestock, or a domestic animal.

The transgenic animals, tissues or cells derived therefrom of various aspects described herein can allow one to study a cellular mechanism or a biological condition mediated by n-6 fatty acids and/or n-3 fatty acids without feeding them with different fat sources that could in turn introduce additional variables into the system. Accordingly, in some embodiments, the genome of the nonhuman transgenic animals described herein can further comprise a gene modification. The gene modification can comprise addition, deletion, and/or mutation of a gene of interest. For example, the gene of interest can be associated with a cellular mechanism or a biological condition influenced by fat metabolism. Examples of such gene of interest include, but are not limited to, ob (obese) gene, leptin receptor gene, and apolipoprotein (apo) E gene.

In some embodiments, the nonhuman transgenic animals described herein can be further engineered to comprise a mutation in ob gene, thus creating an ob/ob or obese non-human transgenic animal model (e.g., an ob/ob or obese transgenic mouse model) of leptin deficiency.

In some embodiments, the nonhuman transgenic animals described herein can be further engineered to be homozygous for a point mutation in the gene for the leptin receptor, thus creating a db/db non-human transgenic animal model (e.g., a db/db transgenic mouse model) of leptin receptor activity deficiency.

In some embodiments, the nonhuman transgenic animals described herein can be further engineered to knock out apoE, thus creating an apoE knockout non-human transgenic animal model (e.g., an apoE knockout transgenic mouse model) of atherosclerosis.

In some embodiments, the gene modification can comprise modification of a host's gene. In some embodiments, the gene modification can comprise expression of a heterologous gene. The heterologous gene can be, for example, a gene that is associated with fat metabolism pathway, a therapeutic gene (e.g., a receptor for a small molecule or chemotherapeutic agent) or a nucleic acid molecule that include a sequence that encodes a polypeptide that improves the utility of the molecule in an assay (e.g., a marker gene or a sequence encoding a fluorescent protein, such as green fluorescent protein (GFP) or enhanced GFP (EGFP), a non-fluorescent marker, e.g., beta-galactosidase, or any other detectable markers known in the art). The heterologous gene can be co-expressed (by way of the same or a separate expression vector) with the first and/or second exogenous and/or heterologous nucleic acid molecules described herein (e.g., encoding fat-2 and/or fat-1).

Depending on whether the construct used contains a constitutively active promoter or a tissue-specific promoter (e.g., a promoter that is active in, e.g., skeletal muscle cells, breast tissue cells, colon tissue cells, neurons, retinal cells, pancreatic cells (e.g., islet cells), other endocrine cells, endothelial cells, skin cells, adipose cells, retinal cells, etc.), the first and/or second exogenous and/or heterologous nucleic acid molecules described herein (e.g., encoding fat-2 and/or fat-1 gene) can be expressed globally within the animal body or in a tissue-specific manner.

The cells and tissues of the transgenic animals of various aspects described herein can contain an altered PUFA content. For example, the cells and tissues of the transgenic animals carrying both of the first and the second exogenous and/or heterologous nucleic acid molecules (e.g., encoding fat-2 and fat-1 gene) can be more desirable for consumption because they are engineered to have a cell or tissue content with a high level of n-3 fatty acids but a reduced level of n-6 fatty acids, as compared to the transgenic animals without these transgenes. Thus, transgenic livestock or any animals that are consumed (e.g., by human or mammals) as food, when they are engineered to express a first heterologous enzyme that converts saturated fat and/or carbohydrates to n-6 fatty acids and a second heterologous enzyme that converts at least one n-6 fatty acid to one or more n-3 fatty acids (e.g., desaturase enzymes encoded by the fat-2 and fat-1 gene, respectively), can be superior or healthier sources of food.

Exemplary Methods of Making Nonhuman Transgenic Animals Described Herein

Methods for making transgenic animals are known in the art, including, e.g., but not limited to, (1) microinjection of genes into the pronuclei of fertilized ova; (2) DNA transfer by retroviruses; (3) injection of embryonic stem cells and/or embryonic germ cells, previously exposed to foreign DNA, into the cavity of blastocysts; (4) sperm mediated exogenous and/or heterologous DNA transfer during in vitro fertilization; (5) liposome-mediated DNA transfer into cells and embryos; (6) electroporation of DNA into sperms, ova or embryos; (7) biolistics; and (8) nuclear transfer with somatic or embryonic cells, which are described in Wheeler et al., "Transgenic technology and Applications in Swine," Theriogenology 56:1345-1370 (2001); Wolf et al., "Transgenic technology in farm animals—progress and perspectives," Exp Physiol 85.6:615-625 (2000), which is hereby incorporated by reference in its entirety.

For example, in one embodiment, the fat-2 transgene construct is applied to a mouse, e.g., by microinjection, to create the fat-2 transgenic mouse. After the transgenic mice are evaluated for showing fat-2 phenotype and genotype, the heterozygous fat 2 transgenic mice can be backcrossed with wild-type mice (e.g., C57BL6 wild-type (WT) mice) for a number of generations (e.g., ~5 generations), and then crossbred with heterozygous fat-1 transgenic mice. The resulting offspring consisted of WT, fat-1, fat-2, and Omega mice. The WT mice do not express any of the fat-1 or fat-2 transgenes. The fat-2 mice carry only the fat-2 transgene, and the Omega mice express both the fat-1 and fat-2 transgenes. See Examples for additional details In some embodiments, an Omega mice can be produced by introducing a construct comprising both fat-2 and fat-1 transgenes into wild-type mice as shown in the Examples.

In another embodiment, one means available for producing a transgenic animal (e.g., but not limited to a mouse) is as follows: Female mice are mated, and the resulting fertilized eggs are dissected out of their oviducts. The eggs are stored in an appropriate medium such as M2 medium (Hogan B. et al. Manipulating the Mouse Embryo, A Laboratory Manual, Cold Spring Harbor Laboratory (1986), which is hereby incorporated by reference). DNA or cDNA encoding gene, minigene or a recombinatorial substrate is purified from a vector (such as plasmids pCEXV-alpha, plasmid pCAGGS) by methods known in the art. Inducible promoters can be fused with the coding region of the DNA to provide an experimental means to regulate expression of the transgene. Alternatively or in addition, tissue specific regulatory elements can be fused with the coding region to permit tissue-specific expression of the transgene. The DNA, in an appropriately buffered solution, is put into a microinjection needle (which can be made from capillary tubing using a pipet puller), and the egg to be injected is put in a depression slide. The needle is inserted into the pronucleus of the egg, and the DNA solution is injected. The injected egg is then transferred into the oviduct of a pseudopregnant mouse (i.e., a mouse stimulated by the appropriate hormones to maintain pregnancy but which is not actually pregnant), where it proceeds to the uterus, implants, and develops to term. This pronuclear DNA microinjection is a classic method for gene transfer and is described by Brem, "Transgenic animals. In Biotechnology, ed. Rehm, H. J. & Reed, G., pp. 745-832. VCH, Weinheim (1993); and Hammer et al., "Production of transgenic rabbits, sheep and pigs by microinjection," Nature 315, 680-683 (1985), which are hereby incorporated by reference in their entirety. The basic method for DNA microinjection as used in mice is described in Rulicke et al., "Germline transformation of mammals by pronuclear microinjection," Experimental Physiology 85:589-601 (2000), which is hereby incorporated by reference in its entirety. Some species specific modifications would be necessary to this method, for example in the recovery of embryos, the microinjection process, and for the transfer of injected embryos to the recipients (Brem, "Transgenic animals. In Biotechnology, ed. Rehm, H. J. & Reed, G., pp. 745-832. VCH, Weinheim (1993), which is hereby incorporated by reference in its entirety). DNA microinjection is not the only method for inserting DNA into the egg cell, and is used here only for exemplary purposes.

Alternatively, a recombinant retrovirus can be used to deliver a transgene as described herein to a cell, e.g., an oocyte or an embryonic cell, or a one-cell embryo. The transgene, and any associated genetic elements, can thus be integrated into the genome of the host cell as a provirus. The cell may then be allowed to develop into a transgenic animal.

In some embodiments, the recombinant retrovirus used to deliver the transgene (e.g., fat-2 and/or fat-1) can be a modified lentivirus, and thus is able to infect both dividing and non-dividing cells. The recombinant retrovirus can comprise a modified lentiviral genome that includes the transgene (e.g., fat-2 and/or fat-1). Further, the modified lentiviral genome can lack endogenous genes for proteins required for viral replication, thus preventing replication in the transgenic animal. The required proteins are provided in trans in the packaging cell line during production of the recombinant retrovirus, as described herein.

In some embodiments, the transgene is incorporated into a viral construct that comprises an intact retroviral 5' LTR and a self-inactivating 3' LTR. The viral construct is preferably introduced into a packaging cell line that packages viral genomic RNA based on the viral construct into viral particles with the desired host specificity. Viral particles are collected and allowed to infect the host cell.

Methods for generating transgenic animals, particularly animals such as mice or rats, have become conventional in the art and are described, for example, in Ausubel et al. (eds) "Current Protocols in Molecular Biology" John Wiley & Sons, Inc., in Hogan, B., Manipulating the Mouse Embryo, (Cold Spring Harbor Laboratory Press, Cold Spring Harbor, N.Y., 1986) and in U.S. Pat. Nos. 5,614,396 5,487,992, 5,464,764, 5,387,742, 5,347,075, 5, 298,422, 5,288,846, 5,221,778, 5,175,384, 5,175,383, 4,873,191, 4,870,009, 4,736,866 as well as Burke and Olson, Methods in Enzymology, 194:251-270, 1991; Capecchi, Science 244:1288-1292, 1989; Davies et al., Nucleic Acids Research, 20 (11) 2693-2698, 1992; Dickinson et al., Human Molecular Genetics, 2(8):1299-1302, 1993; Duff and Lincoln, "Insertion of a pathogenic mutation into a yeast artificial chromosome containing the human APP gene and expression in ES cells", Research Advances in Alzheimer's Disease and Related Disorders, 1995; Huxley et al., Genomics, 9:742-750 1991; Jakobovits et al., Nature, 362:255-261 1993; Lamb et al., Nature Genetics, 5: 22-29, 1993; Pearson and Choi, Proc. Natl. Acad. Sci. USA, 1993, 90:10578-82; Rothstein, Methods in Enzymology, 194:281-301, 1991; Schedl et al., Nature, 362: 258-261, 1993; Strauss et al., Science, 259:1904-1907, 1993, WO 94/23049, WO93/14200, WO 94/06908 and WO 94/28123 also provide information.

Various aspects described herein are not limited to a particular animal. In some embodiments, various aspects described herein can be applied to human and non-human animals. For example, in some embodiments, rodents (e.g., mice or rats) or primates are provided as animal models for alterations in fat metabolism and screening of compounds.

Some aspects described herein provide commercially useful transgenic animals (e.g., livestock animals such as pigs, cows, or sheep) overexpressing the first and/or second exogenous and/or heterologous nucleic acid molecules described herein (e.g., encoding fat-2- or fat-1-related protein). Meat from such transgenic animals can have desirable properties such as lower fat content and higher muscle content. Any suitable technique for generating transgenic livestock can be utilized. In some embodiments, retroviral vector infection is utilized (See e.g., U.S. Pat. No. 6,080,912 and WO/0030437; each of which is herein incorporated by reference in its entirety).

Similar methods can be used for production of other transgenic animals. A transgenic founder animal can be identified based upon the presence of the transgene in its genome and/or expression of transgenic mRNA in tissues or cells of the transgenic animals. For example, a transgenic founder animal carrying a fat-2- or fat-1-related transgene can then be used to breed additional animals carrying the transgene. Moreover, transgenic animals carrying a transgene can further be bred to other transgenic animals carrying other transgenes. A transgenic animal also includes animals in which the entire animal or tissues in the transgenic animal have been produced using the homologously recombinant host cells described herein.

Any techniques known in the art may be used to introduce the transgene, e.g., fat-2 and/or fat-1 genes, expressibly into animals to produce the mammal lines of animals. Such techniques include, but are not limited to, pronuclear microinjection (U.S. Pat. No. 4,873,191); retrovirus mediated gene transfer into germ lines [Van der Putten, et al., 1985, Proc. Natl. Acad. Sci., USA 82, 6148-6152]; gene targeting in embryonic stem cells, such as homologous recombination mediated gene targeting [Thompson, et al., 1989, Cell 56, 313-321 and U.S. Pat. No. 5,614,396]; electroporation of embryos [Lo, 1983, Mol. Cell. Biol. 3, 1803-1814]; and sperm-mediated gene transfer [Nakanishi and Iritani, Mol. Reprod. Dev. 36:258-261 (1993); Maione, Mol. Reprod. Dev. 59:406 (1998); Lavitrano et al. Transplant. Proc. 29:3508-3509 (1997); Lavitrano et al., Proc. Natl. Acad. Sci. USA 99:14230-5 (2002); Lavitrano et al., Mol. Reprod. Dev. 64-284-91 (2003)). Similar techniques are also described in U.S. Pat. No. 6,376,743; U.S. Pat. Publ. Nos. 20010044937, 20020108132, and 20050229263.

In some embodiments, transgene(s) (e.g., fat-2- or fat-1 genes) can be integrated into the genome of a cell of the transgenic animal. The cell can be a somatic cell or a germline cell. In some embodiments, the transgene(s) (e.g., fat-2- or fat-1 genes) can be integrated into the genome of a cell from which a transgenic animal develops and which remains in the genome of the mature animal in one or more cell types or tissues of the transgenic animal.

Transgene(s) (e.g., fat-2- or fat-1 genes) can be overexpressed in a non-human animal such as a mammal. The mammal can be, for example, a rodent such as a mouse, hamster, guinea pig, rabbit or rat, a primate, a porcine, an ovine, a bovine, a feline, a canine, and the like. In specific embodiments, the transgenic animal can be a sheep, goat, horse, cow, bull, pig, rabbit, guinea pig, hamster, rat, gerbil, mouse, or the like. In other embodiments, the transgenic animal can be a bird. In some embodiments, the transgenic animal is a chimeric animals (i.e., those composed of a mixture of genetically different cells), a mosaic animals (i.e., an animal composed of two or more cell lines of different genetic origin or chromosomal constitution, both cell lines derived from the same zygote), an immature animal, a fetus, a blastula, and the like.

Transgenic, non-human animals containing a fat-2- or fat-1-related transgene can be prepared by methods known in the art. In general, a fat-2- or fat-1-related transgene is introduced into target cells, which are then used to prepare a transgenic animal. A fat-2- or fat-1-related transgene can be introduced into target cells, such as for example, pluripotent or totipotent cells such as embryonic stem (ES) cells (e.g., murine embryonal stem cells) or other stem cells (e.g., adult stem cells); germ cells (e.g., primordial germ cells, oocytes, eggs, spermatocytes, or sperm cells); fertilized eggs; zygotes; blastomeres; fetal or adult somatic cells (either differentiated or undifferentiated); and the like. In some embodiments, a fat-2- or fat-1-related transgene is introduced into embryonic stem cells or germ cells of animals (e.g., a rodent) to prepare a transgenic animal overexpressing fat-2- or fat-1-related.

Methods for generating transgenic animals via embryo manipulation and microinjection, particularly animals such as mice, are described, for example, in U.S. Pat. Nos. 4,736,866 and 4,870,009, both by Leder et al., U.S. Pat. No. 4,873,191 by Wagner et al. and in Hogan, B., Manipulating the Mouse Embryo, (Cold Spring Harbor Laboratory Press, Cold Spring Harbor, N.Y., 1986).

Embryonic stem cells can be manipulated according to published procedures (see, e.g., Teratocarcinomas and Embryonic Stem Cells: A Practical Approach, Robertson (ed.), IRL Press, Washington, D.C. (1987); Zjilstra et al., Nature 342:435-38 (1989); Schwartzberg et al., Science 246:799-803 (1989); U.S. Pat. Nos. 6,194,635; 6,107,543; and 5,994,619; each of which is incorporated herein by reference in their entirety). Methods for isolating primordial germ cells are well known in the art. For example, methods of isolating primordial germ cells from ungulates are disclosed in U.S. Pat. No. 6,194,635 (the disclosure of which is incorporated by reference herein in its entirety).

Transgene(s) (e.g., fat-2- or fat-1 genes) can be introduced into a target cell by any suitable method. For example, a fat-2- or fat-1-related transgene can be introduced into a cell by transfection (e.g., calcium phosphate or DEAE-dextran mediated transfection), lipofection, electroporation, microinjection (e.g., by direct injection of naked DNA), biolistics, infection with a viral vector containing a fat-2- or fat-1-related transgene, cell fusion, chromosome-mediated gene transfer, microcell-mediated gene transfer, nuclear transfer, and the like. A fat-2- or fat-1-related transgene can be introduced into cells by electroporation (see, e.g., Wong and Neumann, Biochem. Biophys. Res. Commun. 107:584-87 (1982)) and biolistics (e.g., a gene gun; Johnston and Tang, Methods Cell Biol. 43 Pt A:353-65 (1994); Fynan et al., Proc. Natl. Acad. Sci. USA 90:11478-82 (1993)).

In certain embodiments, a fat-2- or fat-1-related transgene can be introduced into target cells by transfection or lipofection. Suitable agents for transfection or lipofection include, for example, calcium phosphate, DEAE dextran, lipofectin, lipfectamine, DIMRIE C, Superfect, and Effectin (Qiagen), unifectin, maxifectin, DOTMA, DOGS (Transfectam; dioctadecylamidoglycylspermine), DOPE (1,2-dioleoyl-sn-glycero-3-phosphoethanolamine), DOTAP (1,2-dioleoyl-3-trimethylammonium propane), DDAB (dimethyl dioctadecylammonium bromide), DHDEAB (N,N-di-n-hexadecyl-N,N-dihydroxyethyl ammonium bromide), HDEAB (N-n-hexadecyl-N,N-dihydroxyethylammonium bromide), polybrene, poly(ethylenimine) (PEI), and the like. (See, e.g., Banerjee et al., Med. Chem. 42:4292-99 (1999); Godbey et al., Gene Ther. 6:1380-88 (1999); Kichler et al., Gene Ther. 5:855-60 (1998); Birchaa et al., J. Pharm. 183:195-207 (1999); each incorporated by reference herein in its entirety.)

In some embodiments, a fat-2- or fat-1-related transgene can be microinjected into pronuclei of fertilized oocytes or the nuclei of ES cells. A typical method is microinjection of the fertilized oocyte. The fertilized oocytes are microinjected with nucleic acids encoding fat-2- or fat-1-related by standard techniques. The microinjected oocytes are typically cultured in vitro until a "pre-implantation embryo" is obtained. Such a pre-implantation embryo can contain approximately 16 to 150 cells. Methods for culturing fertilized oocytes to the pre-implantation stage include those described by Gordon et al. (Methods in Enzymology 101: 414 (1984)); Hogan et al. (in Manipulating the Mouse Embryo, Cold Spring Harbor Laboratory Press, Cold Spring Harbor, N.Y. (1986)); Hammer et al. (Nature 315:680 (1986)); Gandolfi et al. (J. Reprod. Fert. 81:23-28 (1987)); Rexroad et al. (J. Anim. Sci. 66:947-53 (1988)); Eyestone et al. (J. Reprod. Fert. 85:715-20 (1989)); Camous et al. (J. Reprod. Fert. 72:779-85 (1989)); and Heyman et al. (Theriogenology 27:5968 (1989)) for mice, rabbits, pigs, cows, and the like. (These references are incorporated herein in their entirety.) Such pre-implantation embryos can be thereafter transferred to an appropriate (e.g., pseudopregnant) female. Depending upon the stage of development when the fat-2- or fat-1-related transgene, or a fat-2- or fat-1-related transgene-containing cell is introduced into the embryo, a chimeric or mosaic animal can result. Mosaic and chimeric animals can be bred to form true germline transgenic animals by selective breeding methods. Alternatively, microinjected or transfected embryonic stem cells can be injected into appropriate blastocysts and then the blastocysts are implanted into the appropriate foster females (e.g., pseudopregnant females).

A fat-2- or fat-1-related transgene also can be introduced into cells by infection of cells or into cells of a zygote with an infectious virus containing the mutant gene. Suitable viruses include retroviruses (see generally Jaenisch, Proc. Natl. Acad. Sci. USA 73:1260-64 (1976)); defective or attenuated retroviral vectors (see, e.g., U.S. Pat. No. 4,980, 286; Miller et al., Meth. Enzymol. 217:581-99 (1993); Boesen et al., Biotherapy 6:291-302 (1994); these references are incorporated herein in their entirety), lentiviral vectors (see, e.g., Naldini et al., Science 272:263-67 (1996), incorporated by reference herein in its entirety), adenoviruses or adeno-associated virus (AAV) (see, e.g., Ali et al., Gene Therapy 1:367-84 (1994); U.S. Pat. Nos. 4,797,368 and 5,139,941; Walsh et al., Proc. Soc. Exp. Biol. Med. 204: 289-300 (1993); Grimm et al., Human Gene Therapy 10:2445-50 (1999); the disclosures of which are incorporated by reference herein in their entirety).

Viral vectors can be introduced into, for example, embryonic stem cells, primordial germ cells, oocytes, eggs, spermatocytes, sperm cells, fertilized eggs, zygotes, blastomeres, or any other suitable target cell. In an exemplary embodiment, retroviral vectors which transduce dividing cells (e.g., vectors derived from murine leukemia virus; see, e.g., Miller and Baltimore, Mol. Cell. Biol. 6:2895 (1986)) can be used. The production of a recombinant retroviral vector carrying a gene of interest is typically achieved in two stages. First, a fat-2- or fat-1-related transgene can be inserted into a retroviral vector which contains the sequences necessary for the efficient expression of the fat-2- or fat-1-related transgene (including promoter and/or enhancer elements which can be provided by the viral long terminal repeats (LTRs) or by an internal promoter/enhancer and relevant splicing signals), sequences required for the efficient packaging of the viral RNA into infectious virions (e.g., a packaging signal (Psi), a tRNA primer binding site (−PBS), a 3[prime] regulatory sequence required for reverse transcription (+PBS)), and a viral LTRs). The LTRs contain sequences required for the association of viral genomic RNA, reverse transcriptase and integrase functions, and sequences involved in directing the expression of the genomic RNA to be packaged in viral particles.

Following the construction of the recombinant vector, the vector DNA is introduced into a packaging cell line. Packaging cell lines provide viral proteins required in trans for the packaging of viral genomic RNA into viral particles having the desired host range (e.g., the viral-encoded core (gag), polymerase (pol) and envelope (env) proteins). The host range is controlled, in part, by the type of envelope gene product expressed on the surface of the viral particle. Packaging cell lines can express ecotrophic, amphotropic or xenotropic envelope gene products. Alternatively, the packaging cell line can lack sequences encoding a viral envelope (env) protein. In this case, the packaging cell line can package the viral genome into particles which lack a membrane-associated protein (e.g., an env protein). To produce viral particles containing a membrane-associated protein which permits entry of the virus into a cell, the packaging cell line containing the retroviral sequences can be transfected with sequences encoding a membrane-associated protein (e.g., the G protein of vesicular stomatitis virus (VSV)). The transfected packaging cell can then produce viral particles which contain the membrane-associated protein expressed by the transfected packaging cell line; these viral particles which contain viral genomic RNA derived from one virus encapsidated by the envelope proteins of another virus are said to be pseudotyped virus particles.

Oocytes which have not undergone the final stages of gametogenesis are typically infected with the retroviral vector. The injected oocytes are then permitted to complete maturation with the accompanying meiotic divisions. The breakdown of the nuclear envelope during meiosis permits the integration of the proviral form of the retrovirus vector into the genome of the oocyte. When pre-maturation oocytes are used, the injected oocytes are then cultured in vitro under conditions that permit maturation of the oocyte prior to fertilization in vitro. Oocytes can be matured in vivo and employed in place of oocytes matured in vitro. Methods for the superovulation and collection of in vivo matured (e.g., oocytes at the metaphase 2 stage) oocytes are known for a variety of mammals (e.g., for superovulation of mice, see Hogan et al., in Manipulating the Mouse Embryo: A Laboratory Manual, 2nd ed., Cold Spring Harbor Laboratory Press, Cold Spring Harbor, N.Y. (1994), pp. 130-133; the disclosure of which is incorporated by reference herein in its entirety).

In some embodiments, a transgenic animal is prepared by nuclear transfer. The terms "nuclear transfer" or "nuclear transplantation" refer to methods of preparing transgenic animals wherein the nucleus from a donor cell is transplanted into an enucleated oocyte. Nuclear transfer techniques or nuclear transplantation techniques are known in the art. (See, e.g., Campbell et al., Theriogenology 43:181 (1995); Collas and Barnes, Mol. Reprod. Dev. 38:264-67 (1994); Keefer et al., Biol. Reprod. 50:935-39 (1994); Sims et al., Proc. Natl. Acad. Sci. USA 90:6143-47 (1993); Prather et al., Biol. Reprod. 37:59-86 (1988); Roble et al., J. Anim. Sci. 64:642-64 (1987); International Patent Publications WO 90/03432, WO 94/24274, and WO 94/26884; U.S. Pat. Nos. 4,994,384 and 5,057,420; the disclosures of which are incorporated by reference herein in their entirety.) For example, nuclei of transgenic embryos, pluripotent cells, totipotent cells, embryonic stem cells, germ cells, fetal cells or adult cells (i.e., containing a fat-2- or fat-1-related transgene) can be transplanted into enucleated oocytes, each of which is thereafter cultured to the blastocyst stage. (As used herein, the term "enucleated" refers to cells from which the nucleus has been removed as well as to cells in which the nucleus has been rendered functionally inactive.) The nucleus containing a fat-2- or fat-1-related transgene can be introduced into these cells by any suitable method. The transgenic cell is then typically cultured in vitro to the form a pre-implantation embryo, which can be implanted in a suitable female (e.g., a pseudo-pregnant female).

The transgenic embryos optionally can be subjected, or resubjected, to another round of nuclear transplantation. Additional rounds of nuclear transplantation cloning can be useful when the original transferred nucleus is from an adult cell (e.g., fibroblasts or other highly or terminally differentiated cell) to produce healthy transgenic animals.

Other methods for producing a transgenic animal expressing a fat-2- or fat-1-related transgene include the use male sperm cells to carry the fat-2- or fat-1-related transgene to an egg. In one example, a fat-2- or fat-1-related transgene can be administered to a male animal's testis in vivo by direct delivery. The fat-2- or fat-1-related transgene can be introduced into the seminiferous tubules, into the rete testis, into the vas efferens or vasa efferentia, using, for example, a micropipette.

In some embodiments, a fat-2- or fat-1-related transgene can be introduced ex vivo into the genome of male germ cells. A number of known gene delivery methods can be used for the uptake of nucleic acid sequences into the cell. Suitable methods for introducing a fat-2- or fat-1-related transgene into male germ cells include, for example, liposomes, retroviral vectors, adenoviral vectors, adenovirus-enhanced gene delivery systems, or combinations thereof.

Following transfer of a fat-2- or fat-1-related transgene into male germ cells, a transgenic zygote can be formed by breeding the male animal with a female animal. The transgenic zygote can be formed, for example, by natural mating (e.g., copulation by the male and female vertebrates of the same species), or by in vitro or in vivo artificial means. Suitable artificial means include, but are not limited to, artificial insemination, in vitro fertilization (IVF) and/or other artificial reproductive technologies, such as intracytoplasmic sperm injection (ICSI), subzonal insemination (SUZI), partial zona dissection (PZD), and the like, as will be appreciated by the skilled artisan. (See, e.g., International Patent Publication WO 00/09674, the disclosure of which is incorporated by reference herein in its entirety.)

A variety of methods can be used to detect the presence of a fat-2- or fat-1-related transgene in target cells and/or transgenic animals. Since the frequency of transgene incorporation can be low, although reliable, the detection of transgene integration in the pre-implantation embryo can be desirable. In one aspect, embryos are screened to permit the identification of fat-2- or fat-1-related-transgene-containing embryos for implantation to form transgenic animals. For example, one or more cells are removed from the pre-implantation embryo. When equal division of the embryo is used, the embryo is typically not cultivated past the morula stage (32 cells). Division of the pre-implantation embryo (see, e.g., Williams et al., Theriogenology 22:521-31 (1986)) results in two "hemi-embryos" (hemi-morula or hemi-blastocyst), one of which is capable of subsequent development after implantation into the appropriate female to develop in utero to term. Although equal division of the pre-implantation embryo is typical, it is to be understood that such an embryo can be unequally divided either intentionally or unintentionally into two hemi-embryos. Essentially, one of the embryos which is not analyzed usually has a sufficient cell number to develop to full term in utero. In a specific embodiment, the hemi-embryo (which is not analyzed), if shown to be transgenic, can be used to generate a clonal population of transgenic animals, such as by embryo splitting.

One of the hemi-embryos formed by division of pre-implantation embryos can be analyzed to determine if the fat-2- or fat-1-related transgene has integrated into the genome of the organism. Each of the other hemi-embryos can be maintained for subsequent implantation into a recipient female, typically of the same species. A typical method for detecting a fat-2- or fat-1-related transgene at this early stage in the embryo's development uses these hemi-embryos in connection with allele-specific PCR, which can differentiate between a fat-2- or fat-1-related transgene and an endogenous transgene. (See, e.g., McPherson et al. (eds) PCR2: A Practical Approach, Oxford University Press (1995); Cha et al., PCR Methods Appl. 2:14-20 (1992); the disclosures of which are incorporated by reference herein.)

After a hemi-embryo is identified as a transgenic hemi-embryo, it optionally can be cloned. Such embryo cloning can be performed by several different approaches. In one cloning method, the transgenic hemi-embryo can be cultured in the same or in a similar media as used to culture individual oocytes to the pre-implantation stage. The "transgenic embryo" so formed (typically a transgenic morula) can then be divided into "transgenic hemi-embryos" which can be implanted into a recipient female to form a clonal population of two transgenic non-human animals. Alternatively, the two transgenic hemi-embryos obtained can be again cultivated to the pre-implantation stage, divided, and recultivated to the transgenic embryo stage. This procedure can be repeated until the desired number of clonal transgenic embryos having the same genotype are obtained. Such transgenic embryos can then be implanted into recipient females to produce a clonal population of transgenic non-human animals.

In addition to the foregoing methods for detecting the presence of a fat-2- or fat-1-related transgene, other methods can be used. Such methods include, for example, in utero and postpartum analysis of tissue. In utero analysis can be performed by several techniques. In one example, transvaginal puncture of the amniotic cavity is performed under echoscopic guidance (see, e.g., Bowgso et al., Bet. Res. 96:124-27 (1975); Rumsey et al., J. Anim. Sci. 39:386-91 (1974)). This involves recovering amniotic fluid during gestation. Most of the cells in the amniotic fluid are dead. Such cells, however, contain genomic DNA which can be subjected to analysis (e.g., by PCR) for the fat-2- or fat-1-related transgene as an indication of a successful transgenesis. Alternatively, fetal cells can be recovered by chorion puncture. This method also can be performed transvaginally and under echoscopic guidance. In this method, a needle can be used to puncture the recipient animal's placenta, particularly the placentonal structures, which are fixed against the vaginal wall. Chorion cells, if necessary, can be separated from maternal tissue and subjected to PCR analysis for the fat-2- or fat-1-related transgene as an indication of successful transgenesis.

The presence of a fat-2- or fat-1-related transgene also can be detected after birth. In such cases, the presence of a fat-2- or fat-1-related transgene can be detected by taking an appropriate tissue biopsy, such as from an ear or tail of the putative transgenic animal. The presence of a fat-2- or fat-1-related transgene can also be detected by assaying for expression of the fat-2- or fat-1-related transgene polypeptide in a tissue.

The location and number of integration events can be determined by methods known to the skilled artisan. (See, e.g., Ausubel et al., supra; Sambrook et al., supra.) For example, PCR or Southern blot analysis of genomic DNA extracted from infected oocytes and/or the resulting embryos, offspring and tissues derived therefrom, can be employed when information concerning the site of integration of the viral DNA into the host genome is desired. To examine the number of integration sites present in the host genome, the extracted genomic DNA can typically be digested with a restriction enzyme which cuts at least once within the vector sequences. If the enzyme chosen cuts twice within the vector sequences, a band of known (i.e., predictable) size is generated in addition to two fragments of novel length which can be detected using appropriate probes.

Clones of the non-human transgenic animals described herein can also be produced according to the methods described in Wilmut et al., Nature 385:810-813 (1997) and PCT International Publication Nos. WO 97/07668 and WO 97/07669. For example, a cell, e.g., a somatic cell, from the transgenic animal can be isolated and induced to exit the growth cycle and enter GO phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal is a clone of the transgenic animal from which the cell, e.g., the somatic cell, is isolated.

Other methods of preparing transgenic animals are disclosed, for example, in U.S. Pat. Nos. 5,633,076 or 6,080,912; and in International Patent Publications WO 97/47739, WO 99/37143, WO 00/75300, WO 00/56932, and WO 00/08132, the disclosures of which are incorporated herein by reference in their entirety.

In a related aspect, a non-human transgenic animal expressing a fat-2- or fat-1-related transgene can be a source of cells to establish cell lines expressing the fat-2- or fat-1-related transgene. For example, cell lines can be derived from mice that express a cognate, heterologous fat-2- or fat-1-related transgene.

The transgenic animals described herein can have other genetic alterations in addition to the presence of the fat-2- or fat-1-related transgenes. For example, the host's genome may be altered to affect the function of endogenous genes encoding a disease-related gene or a therapeutic gene, contain marker genes, or other genetic alterations consistent with the desired applications. For example, although not necessary to the operability of various aspects described herein, the transgenic animals described herein can have alterations to endogenous genes in addition to (or alternatively) for fat-2 and/or fat-1 gene, the genetic alterations described above.

Clones of the transgenic animals described herein can also be produced according to the methods described in Wilmut, I. et al. Nature 385:810-813 (1997) and PCT International Publication Nos. WO 97/07668 and WO 97/07669. In brief, a cell, e.g., a somatic cell, from the transgenic animal can be isolated and induced to exit the growth cycle and enter GO phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal is a clone of the transgenic animal from which the cell, e.g., the somatic cell, is isolated.

Yet another aspect provides a population of cells isolated from the transgenic animals described herein. For example, the transgenic animals described herein can be used as a source of cells for cell culture.

Transgene Constructs for Making Transgenic Animals Described Herein

In one aspect, provided herein is a transgene construct comprising a first exogenous and/or heterologous nucleic acid molecule operably linked to a promoter, wherein the first exogenous and/or heterologous nucleic acid molecule comprises a nucleotide sequence encoding a delta 12 fatty acid desaturase, e.g., fat-2, or a nucleotide sequence that is a biologically active variant thereof, wherein the nucleotide sequence does not correspond to *C. elegans* wild-type fat-2 gene, and wherein the promoter directs expression of the first exogenous and/or heterologous nucleic acid molecule in an animal cell upon introduction of the transgene construct into the cell. For example, the transgene construct can be introduced into the cell by microinjection.

In some embodiments, the first exogenous and/or heterologous nucleic acid molecule can comprise (i) a nucleotide sequence of SEQ ID NO. 1 or (ii) a nucleotide sequence that is a biologically active variant of SEQ ID NO. 1 and is at least about 70% or more (including, e.g., at least about 80%, at least about 90%, at least about 95% or more) identical to SEQ ID NO. 1.

In some embodiments, the transgene construct can further comprise a second exogenous and/or heterologous nucleic acid molecule, the second exogenous and/or heterologous nucleic acid molecule comprising a nucleotide sequence encoding an enzyme that converts at least one n-6 fatty acid to one or more n-3 fatty acids. In some embodiments, the nucleotide sequence encoding an enzyme that converts at least one n-6 fatty acid to one or more n-3 fatty acids can be a nucleotide sequence encoding an n-3 fatty acid desaturase, or a nucleotide sequence that is a biologically active variant thereof, wherein the nucleotide sequence does not correspond to *C. elegans* wild-type fat-1 gene.

In some embodiments, the second exogenous and/or heterologous nucleic acid molecule can comprise (i) a nucleotide sequence of SEQ ID NO. 2 or (ii) a nucleotide sequence that is a biologically active variant of SEQ ID NO. 2 and is at least about 70% or more (including, e.g., at least about 80%, at least about 90%, at least about 95% or more) identical to SEQ ID NO. 2.

In some embodiments where the second exogenous and/or heterologous nucleic acid molecule is present in a transgene construct described herein, the second exogenous and/or heterologous nucleic acid molecule can be operably linked to the same promoter or a different promoter, wherein said the same promoter or the different promoter directs expression of the second exogenous and/or heterologous nucleic acid in the transgenic animal cell upon introduction of the transgene construct into the cell. Examples of animal cells include, but are not limited to, cells derived from any animals described herein, e.g., but not limited to a cow, a mouse, a rat, a pig, a sheep, a goat, a rabbit, a buffalo, a fish, a poultry, a livestock or a domestic animal.

In some embodiments, the transgene construct can comprise a vector (e.g., an expression vector). In some embodiments, a vector can be an adenoviral vector. Other viral vectors that can be employed as expression constructs include vectors derived from viruses such as vaccinia virus (e.g., a pox virus or a modified vaccinia virus ankara (MVA)), an adeno-associated virus (AAV), or a herpes virus. These viruses offer several attractive features for use in connection with animal cells, including human cells. For example, herpes simplex viruses (e.g., HSV-1) can be selected to deliver a desaturase (e.g., fat-1/fat-2 or a homologue thereof (or biologically active variants, including codon-optimized variants)) to cells of interest.

Retroviruses, liposomes, and plasmid vectors are also well known in the art and can also be used to deliver a fat-2 and/or fat-1-encoding sequence to a cell (e.g., the expression vector pUR278 can be used when one wishes to fuse a desaturase-encoding (e.g., fat-1 and/or fat-2) sequence to the lacZ gene; lacZ encodes the detectable marker β-galactosidase (see, e.g., Ruther et al, EMBOJ. 2:1791, 1983)).

As noted, a desaturase-encoding sequence (e.g. a fat-1 and/or fat-2 sequence) or a biologically active variant thereof (including a codon optimized sequence) can also be fused to other types of heterologous sequences, such as a sequence that encodes another therapeutic gene or a sequence that, when expressed, improves the quantity or quality (e.g., solubility or circulating half-life) of the fusion protein. For example, pGEX vectors can be used to express the desaturase enzymes fused to glutathione S-transferase (GST). In general, such fusion proteins are soluble and can be readily purified from lysed cells by adsorption to glutathione-agarose beads followed by elution in the presence of free glutathione. The pGEX vectors (Pharmacia Biotech Inc; Smith and Johnson, Gene 67:31-40, 1988) are designed to include thrombin or factor Xa protease cleavage sites so that the cloned target gene product can be released from the GST moiety. Other fusion partners include albumin and a region (e.g., the Fc region, with or without the hinge region) of an immunoglobulin molecule (e.g., IgG, IgA, IgM, or IgE). Other useful vectors include pMAL (New England Biolabs, Beverly, Mass.) and pRIT5 (Pharmacia, Piscataway, N.J.), which fuse maltose E binding protein and protein A, respectively, to an n-3 desaturase.

Transgene expression can be sufficiently prolonged from episomal systems, so that readministration of any given expression vector, with its transgene, is not necessary.

Alternatively, the vector can be designed to promote integration into the host genome, preferably in a site-specific location, which would help ensure that the transgene is not lost during the cell's lifetime. Whatever the means of delivery, transcriptional control, exerted by the host cell, would promote tissue specificity and regulate transgene expression.

Accordingly, the nucleic acid molecules described herein can include sequences that promote integration of a desaturase-encoding sequence into a host's genome.

The expression vector can be selected or designed depending on, for example, the type of host cell to be transformed and the level of protein expression desired. For example, when the host cells are mammalian cells, the expression vector can include viral regulatory elements, such as promoters derived from polyoma, Adenovirus 2, cytomegalovirus and Simian Vims 40. These regulatory elements can be used with non-mammalian (e.g., avian or fish) cells as well. The nucleic acid inserted (i.e., the sequence to be expressed; here, a desaturase such as fat-1 and/or fat-2) can also be modified to encode residues that are preferentially utilized in *E. coli* (Wada et al, Nucleic Acids Res. 20:2111-2118, 1992). Similarly, one can preferentially modify codons, if necessary or desired, in organisms other than *E. coli*. Modifications such as these (e.g., incorporation of various regulatory elements and codon optimization) can be achieved by standard recombinant techniques. More generally, the expression vectors can be designed to express proteins in prokaryotic or eukaryotic cells. For example, polypeptides can be expressed in bacterial cells (e.g., *E. coli*), fungi, yeast, or insect cells (e.g., using baculovirus expression vectors). For example, a baculovirus such as *Autographa californica* nuclear polyhedrosis virus (AcNPV), which grows in *Spodoptera frugiperda* cells, can be used as a vector to express a fat-1 and/or fat-2 gene. While the invention is not so limited, *E. coli*, yeast, and insect cells can serve as host cells when a primary objective of the expression is the production and purification of an n-3 desaturase. As noted herein, the invention also encompasses expression of an n-3 desaturase in higher order cells, including those within a wide variety of different types of transgenic animals.

As noted above, when the host cell is obtained from, or is a cell within, a multicellular animal, the expression vectors and nucleic acids used to express the desaturase (e.g., a fat-1 and/or fat-2 nucleic acid sequence) can also contain a tissue-specific promoter. Such promoters are known in the art and include, but are not limited to liver-specific promoters (e.g., albumin; Miyatake et al, J. Virol. 71:5124-5132, 1997), muscle-specific promoters (e.g., myosin light chain 1 (Shi et al, Hum. Gene Ther. 8:403-410, 1997) or α-actin), pancreatic-specific promoter (e.g., insulin or glucagon promoters), neural-specific promoters (e.g., the tyrosine hydroxylase promoter or the neuron-specific enolase promoter), endothelial cell-specific promoters (e.g., von Willebrandt; Ozaki et al, Hum Gene Ther. 7:1483-1490, 1996), and smooth muscle-cell specific promoters (e.g., 22a). Tumor-specific promoters are also being used in developing cancer therapies, including tyrosine kinase-specific promoters for B16 melanoma (Diaz et al, J. Virol. 72:789-795, 1998), DF3/MUC1 for certain breast cancers (Wen et al, Cancer Res. 53:641-651, 1993; for breast cancer, an adipose-specific promoter region of human aromatase cytochrome p450 (p450arom) can also be used (see U.S. Pat. No. 5,446,143; Mahendroo et al, J. Biol. Chem. 268:19463-19470, 1993; and Simpson et al, Clin. Chem. 39:317-324, 1993). An α-fetoprotein promoter can be used to direct expression in hepatomas (Chen et al, Cancer Res. 55:5283-5287, 1995). Where tissue-specific expression is not required or desired, the desaturase (e.g., fat-1 and/or fat-2)-encoding sequence can be placed under the control of (e.g., operatively linked to) a constitutively active promoter (e.g., a (β-actin promoter). Other constitutively active promoters are known and used in the art.

The vectors and other nucleic acid molecules (e.g., the fat-1 and/or fat-2 cDNA per se) can also include sequences that limit the temporal expression of the transgene. For example, the transgene can be controlled by drug inducible promoters by, for example, including a cAMP response element (CRE) enhancer in a promoter and treating the transfected or infected cell with a cAMP modulating drug (Suzuki et al, Hum. Gene Ther. 7:1883-1893, 1996). Alternatively, repressor elements can prevent transcription in the presence of the drug (Hu et al, Cancer Res. 57:3339-3343, 1997). Spatial control of expression has also been achieved by using ionising radiation (radiotherapy) in conjunction with the ergl gene promoter. Constructs that contain such regulatory sequences are also provided herein.

Host cells that include a nucleic acid molecule described herein, including an expression vector, are also within the scope of various aspects described herein. The cells can be prokaryotic or eukaryotic. Suitable prokaryotic cells include bacterial cells, and suitable eukaryotic cells include those of mammals, birds, and fish. Cell lines, including those established and deposited in public depositories, can also be used as host cells. Any of these cells can be used, inter alia, in the process of optimizing a nucleic acid sequence. The cell may be considered healthy or diseased (e.g., the cell can be affected by inflammation or can be one that is transformed and/or proliferating at an undesirable (e.g., undesirably high) rate).

Delta 12 Fatty Acid Desaturase and/or n-3 Fatty Acid Desaturase Transgenes:

A "delta 12 fatty acid desaturase transgene" refers to a nucleic acid encoding an enzyme that converts carbohydrates and/or saturated fats to n-6 fatty acids, or a biologically active variant or fragment thereof. The delta 12 fatty acid desaturase transgene can be, for example, a portion of genomic DNA, cDNA, mRNA, RNA or a fragment thereof encoding a functional enzyme or a functionally active fragment or functional derivative of the enzyme. An exemplary delta 12 fatty acid desaturase can be a full length fat-2 transgene or a functionally active fragment or functional derivative thereof.

As used herein, the term "n-3 fatty acid desaturase transgene" refers to a nucleic acid encoding an enzyme that can convert at least one n-6 fatty acid to one or more n-3 fatty acids, or a biologically active variant thereof as defined herein. The n-3 fatty acid desaturase transgene can be, for example, a portion of genomic DNA, cDNA, mRNA, RNA or a fragment thereof encoding a functional enzyme or a functionally active fragment or functional derivative of the enzyme. An exemplary n-3 fatty acid desaturase can be a full length fat-1 gene or a functionally active fragment or functional derivative thereof.

The term "functional derivative" refers to a fragment, homologue, derivative or analog having one or more functions associated with a full-length (wild-type) polypeptide (e.g., enzymatic activity of producing essential fatty acids). In some embodiments, a functional derivative of a delta 12 fatty acid desaturase is a fragment, homologue, derivative or analog of the full length (e.g., wild-type) enzyme such that the functional derivative is capable of converting saturated fats and/or carbohydrates to n-6 fatty acids. In some embodiments, a functional derivative of an n-3 fatty acid desaturase is a fragment, homologue, derivative or analog of the full length (e.g., wild-type) enzyme such that the functional derivative is capable of converting at least one n-6 fatty acid to one or more n-3 fatty acids.

In some embodiments, delta 12 fatty acid desaturase and/or n-3 fatty acid desaturase transgenes can be cognate heterologous transgenes from one species expressed in a host of a different species. For example, a cognate heterologous fat-2 or fat-1 transgene refers to a corresponding gene from another species; thus, if murine is the host to be made transgenic, a fat-1 gene or fat-2 gene from C. elegan is a cognate heterologous gene. In some embodiments, the delta 12 fatty acid desaturase and/or n-3 fatty acid desaturase transgenes can be derived from the same species as the transgenic animal (e.g., a fish fat-2 or fat-1 related transgene overexpressed in a fish).

A transgene containing various gene segments encoding a cognate heterologous protein sequence may be readily identified, e.g. by hybridization or DNA sequencing, as being from a species of organism other than the transgenic animal. In some embodiments, the cognate fat-2- or fat-1-related transgene is at least 75%, at least 80%, at least 85%, at least 90% or at least 95% identical to the C. elegans fat-2- or fat-1-related transgene. As used herein, the terms "identical" or "percent identity," in the context of two or more nucleic acids or polypeptide sequences, refer to two or more sequences or subsequences that are the same or have a specified percentage of nucleotides or amino acid residues that are the same, when compared and aligned for maximum correspondence, as measured using one of the following sequence comparison algorithms, or by visual inspection. The phrase "substantially identical," in the context of two nucleic acids or polypeptides, refers to two or more sequences or subsequences that have at least 60%, typically 80%, most typically 90-95% nucleotide or amino acid residue identity, when compared and aligned for maximum correspondence, as measured using one of the following sequence comparison algorithms, or by visual inspection. An indication that two polypeptide sequences are "substantially identical" is that one polypeptide is immunologically reactive with antibodies raised against the second polypeptide.

In some embodiments, the fat-2- or fat-1-related enzyme is at least 75%, at least 80%, at least 85%, at least 90% or at least 95% similar to the *C. elegans* fat-2- or fat-1-related enzyme. As used herein, "similarity" or "percent similarity" in the context of two or polypeptide sequences, refer to two or more sequences or subsequences that are the same or have a specified percentage of amino acid residues or conservative substitutions thereof, that are the same, when compared and aligned for maximum correspondence, as measured using one of the following sequence comparison algorithms, or by visual inspection. By way of example, a first amino acid sequence can be considered similar to a second amino acid sequence when the first amino acid sequence is at least 50%, 60%, 70%, 75%, 80%, 90%, or even 95% identical, or conservatively substituted, to the second amino acid sequence when compared to an equal number of amino acids as the number contained in the first sequence, or when compared to an alignment of polypeptides that has been aligned by a computer similarity program known in the art, as discussed below.

The term "substantial similarity" in the context of polypeptide sequences, indicates that the polypeptide comprises a sequence with at least 60% sequence identity to a reference sequence, or 70%, or 80%, or 85% sequence identity to the reference sequence, or most preferably 90% identity over a comparison window of about 10-20 amino acid residues. In the context of amino acid sequences, "substantial similarity" further includes conservative substitutions of amino acids. Thus, a polypeptide is substantially similar to a second polypeptide, for example, where the two peptides differ by one or more conservative substitutions.

The term "conservative substitution," when describing a polypeptide, refers to a change in the amino acid composition of the polypeptide that does not substantially alter the polypeptide's activity. Thus, a "conservative substitution" of a particular amino acid sequence refers to substitution of those amino acids that are not critical for polypeptide activity or substitution of amino acids with other amino acids having similar properties (e.g., acidic, basic, positively or negatively charged, polar or non-polar, etc.) such that the substitution of even critical amino acids does not substantially alter activity. Conservative substitution tables providing functionally similar amino acids are well known in the art. For example, the following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W). (See also Creighton, Proteins, W. H. Freeman and Company (1984).) In addition, individual substitutions, deletions or additions that alter, add or delete a single amino acid or a small percentage of amino acids in an encoded sequence are also "conservative substitutions."

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, for example, by the local homology algorithm of Smith and Waterman (Adv. Appl. Math. 2:482 (1981), which is incorporated by reference herein), by the homology alignment algorithm of Needleman and Wunsch (J. Mol. Biol. 48:443-53 (1970), which is incorporated by reference herein), by the search for similarity method of Pearson and Lipman (Proc. Natl. Acad. Sci. USA 85:2444-48 (1988), which is incorporated by reference herein), by computerized implementations of these algorithms (e.g., GAP, BESTFIT, FASTA, and TFASTA in the Wisconsin Genetics Software Package, Genetics Computer Group, 575 Science Dr., Madison, Wis.), or by visual inspection. (See generally Ausubel et al. (eds.), Current Protocols in Molecular Biology, 4th ed., John Wiley and Sons, New York (1999)).

One example of a useful algorithm is PILEUP. PILEUP creates a multiple sequence alignment from a group of related sequences using progressive, pairwise alignments to show the percent sequence identity. It also plots a tree or dendogram showing the clustering relationships used to create the alignment. PILEUP uses a simplification of the progressive alignment method of Feng and Doolittle (J. Mol. Evol. 25:351-60 (1987), which is incorporated by reference herein). The method used is similar to the method described by Higgins and Sharp (Comput. Appl. Biosci. 5:151-53 (1989), which is incorporated by reference herein). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of an algorithm that is suitable for determining percent sequence identity and sequence similarity is the BLAST algorithm, which is described by Altschul et al. (J. Mol. Biol. 215:403-410 (1990), which is incorporated by reference herein). (See also Zhang et al., Nucleic Acid Res. 26:3986-90 (1998); Altschul et al., Nucleic Acid Res. 25:3389-402 (1997), which are incorporated by reference herein). Software for performing BLAST analyses is publicly available through the National Center for Biotechnology Information internet web site. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al. (1990), supra). These initial neighborhood word hits act as seeds for initiating searches to find longer HSPs containing them. The word hits are then extended in both directions along each sequence for as far as the cumulative alignment score can be increased. Extension of the word hits in each direction is halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a word-length (W) of 11, the BLOSUM62 scoring matrix (see Henikoff and Henikoff, Proc. Natl. Acad. Sci. USA 89:10915-9 (1992), which is incorporated by reference herein) alignments (B) of 50, expectation (E) of 10, M=5, N=−4, and a comparison of both strands.

In addition to calculating percent sequence identity, the BLAST algorithm also performs a statistical analysis of the similarity between two sequences (see, e.g., Karlin and Altschul, Proc. Natl. Acad. Sci. USA 90:5873-77 (1993), which is incorporated by reference herein). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more typically less than about 0.01, and most typically less than about 0.001.

In some embodiments, the fat-2- or fat-1-related transgene is expressed from an expression construct comprising a transcriptional unit. A "transcriptional unit" refers to a polynucleotide sequence that comprises a fat-2- or fat-1-related transgene (e.g., the structural gene (exons)) or a functionally active fragment thereof, a cis-acting linked promoter and other cis-acting sequences necessary for efficient transcription of the structural sequences, distal regulatory elements necessary for appropriate tissue-specific and developmental transcription of the structural sequences (as appropriate), and additional cis sequences for efficient transcription and translation (e.g., polyadenylation site, mRNA stability controlling sequences, or the like). Regulatory or other sequences useful in expression vectors can form part of the transgene sequence. This includes intronic sequences and polyadenylation signals, if not already included. The promoter and other cis-acting sequences are operatively linked to the structural gene.

In some embodiments, the promoter is a tissue-specific promoter, for example, a muscle specific promoter, a bone specific promoter, or an organ-specific promoter. Exemplary muscle-specific promoter are, for example but not limited to, α-myosin heavy chain which is specific for cardiac muscle, the myosin light chain-2 gene control region which is active in skeletal muscle (Shani, Nature 314:283-86 (1985)); and the gonadotropic releasing hormone gene control region which is active in the hypothalamus (Mason et al., Science 234:1372-78 (1986)). In an exemplary embodiment, the promoter is the MKC promoter for expression in skeletal muscle cells. In alternative embodiments, the muscle promoter is a smooth muscle promoter, for example but no limited to SM22a, which directs expression in vascular smooth muscle cells.

In some embodiments, the muscle specific promoter is an inducible muscle-specific promoter. For example, the delta 12 fatty acid desaturase (e.g., fat-2) and/or n-3 fatty acid desaturase (e.g., fat-1) transgenes can operably linked to one or more regulatory elements that provides regulated or conditional expression, e.g., tissue specific or inducible expression, of an operatively linked nucleic acid. One skilled in the art can readily determine an appropriate tissue-specific promoter or enhancer that allows expression of the transgene in a desired tissue. Any of a variety of inducible promoters or enhancers can also be included in the vector for regulatable expression of the transgene. An "inducible" promoter is a system that allows for controllable and careful regulation of gene expression. See, Miller and Whelan, Human Gene Therapy, 8:803-815 (1997). The phrase "inducible promoter" or "inducible system" as used herein includes systems wherein promoter activity can be regulated using an externally delivered agent.

Such systems include, for example, systems using the lac repressor from *E. coli* as a transcription modulator to regulate transcription from lac operator-bearing mammalian cell promoters (Brown et al. Cell, 49:603-612, 1987); systems using the tetracycline repressor (tetR)(Gossen and Bujard, Proc. Natl. Acad. Sci. USA 89: 5547-5551, 1992; Yao et al., Human Gene Ther. 9:1939-1950, 1998; Shokelt et al., Proc. Natl. Acad. Sci. USA 92:6522-6526, 1995). Other such systems include, for example but not limited to; FK506 dimer, VP16 or p65 using castradiol, RU486/mifepristone, diphenol muristerone or rapamycin (see, Miller and Whelan, supra, at FIG. 2). Yet another example is an ecdysone inducible system (see, e.g. Karns et al, MBC Biotechnology 1:11, 2001). Inducible systems are available, e.g., from Invitrogen, Clontech, and Ariad. Systems using a repressor with the operon are preferred.

Some inducible promoters cause little or undetectable levels of expression (or no expression) in the absence of the appropriate stimulus. Other inducible promoters cause detectable constitutive expression in the absence of the stimulus. Whatever the level of expression is in the absence of the stimulus, expression from any inducible promoter is increased in the presence of the correct stimulus. Such inducible systems, include, for example, tetracycline inducible system (Gossen & Bizard, Proc. Natl. Acad. Sci. USA, 89:5547-5551 (1992); Gossen et al., Science, 268:1766-1769 (1995); Clontech, Palo Alto, Calif.); metalothionein promoter induced by heavy metals; insect steroid hormone responsive to ecdysone or related steroids such as muristerone (No et al., Proc. Natl. Acad. Sci. USA, 93:3346-3351 (1996); Yao et al., Nature, 366:476-479 (1993); Invitrogen, Carlsbad, Calif.); mouse mammary tumor virus (MMTV) induced by steroids such as glucocortocoid and estrogen (Lee et al., Nature, 294:228-232 (1981); and heat shock promoters inducible by temperature changes. Other example systems include a Gal4 fusion inducible by an antiprogestin such as mifepristone in a modified adenovirus vector (Burien et al., Proc. Natl. Acad. Sci. USA, 96:355-360 (1999). Another such inducible system utilizes the drug rapamycin to induce reconstitution of a transcriptional activator containing rapamycin binding domains of FKBP12 and FRAP in an adeno-associated virus vector (Ye et al., Science, 283:88-91 (1999)). Other inducible systems are known by persons skilled in the art and can be used in the methods described herein.

Another example of a regulated expression system is the cre/loxP recombinase system of bacteriophageP1. For a description of the cre/loxP recombinase system, see, e.g., Lakso et al. PNAS 89:6232-6236 (1992). Another example of a recombinase system is the FLP recombinase system of *S. cerevisiae* (O'Gorman et al. Science 251:1351-1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

One can adapt these "inducible" systems so that the fatty acid desaturase enzymes (e.g., fat-2- or fat-1-related enzymes), constitutively active isoform of is regulated by the addition of an external agent, but is only expressed in a specific tissue. Such a promoter system is termed "inducible tissue-specific promoter" herein. Thus, in some embodiments, the fatty acid desaturase transgene (e.g., fat-2 and/or or fat-1-related transgene) is operatively linked to an inducible promoter that regulates the expression of the transgene in tissue. Such a system may be comprised on one or more exogenous and/or heterologous DNAs or transgenes, which may be may be operatively linked.

In one embodiment, a regulatory element such as a transcriptional regulatory element or an enhancer can be included in the transgene. In one embodiment, a "transcriptional regulatory element" or "TRE" is introduced for regulation of the gene of interest. As used herein, a TRE is a polynucleotide sequence, preferably a DNA sequence, that regulates (i.e., controls) transcription of an operably-linked polynucleotide sequence by an RNA polymerase to form RNA. As used herein, a TRE increases transcription of an operably linked polynucleotide sequence in a host cell that allows the TRE to function. The TRE comprises an enhancer element and/or pox promoter element, which may or may not be derived from the same gene. The promoter and enhancer components of a TRE may be in any orientation and/or distance from the coding sequence of interest, and comprise multimers of the foregoing, as long as the desired transcriptional activity is obtained. As discussed herein, a TRE may or may not lack a silencer element. For example, In some embodiments, an "enhancer" for regulation of the gene of interest can be included in the transgene constructs described herein. An enhancer is a term well understood in the art and is a polynucleotide sequence derived from a gene which increases transcription of a gene which is operably-linked to a promoter to an extent which is greater than the transcription activation effected by the promoter itself when operably-linked to the gene, i.e. it increases transcription from the promoter. Having "enhancer activity" is a term well understood in the art and means what has been stated, i.e., it increases transcription of a gene which is operably linked to a promoter to an extent which is greater than the increase in transcription effected by the promoter itself when operatively linked to the gene, i.e., it increases transcription from the promoter.

The activity of a regulatory element such as a TRE or an enhancer generally depends upon the presence of transcriptional regulatory factors and/or the absence of transcriptional regulatory inhibitors. Transcriptional activation can be measured in a number of ways known in the art (and described in more detail below), but is generally measured by detection and/or quantization of mRNA or the protein product of the coding sequence under control of (i.e., operatively linked to) the regulatory element. As discussed herein, the regulatory element can be of varying lengths, and of varying sequence composition. By transcriptional activation, it is intended that transcription can be increased above basal levels in the target cell by at least about 2-fold, preferably at least about 5-fold, preferably at least about 10-fold, more preferably at least about 20-fold. More preferably at least about 50-fold, more preferably at least about 100-fold, even more preferably at least about 200-fold, even more preferably at least about 400- to about 500-fold, even more preferably at least about 1000-fold. Basal levels are generally the level of activity, if any, in a non-target cell, or the level of activity (if any) of a reporter construct lacking the TRE of interest as tested in a target cell type.

The transgene may also include a reporter gene, e.g., reporter genes include β-galactosidase, luciferase, Green fluorescent protein (GFP), chloramphenicol acetyltransferase (CAT), alkaline phosphatase, horse radish peroxidase and the like. In one embodiment, a reporter gene is fused to fat-2- or fat-1-related gene.

Regulatory or other sequences useful in expression vectors can form part of the transgenic sequence. This includes, but is not limited to, intronic sequences, transcription termination signals and polyadenylation signals, if not already included. A conditional regulatory sequence(s) can be operably linked to the transgene to direct expression of the transgene to particular cells.

Use of the Nonhuman Transgenic Animals, or Cells or Tissues Derived Therefrom

Accordingly, another aspect provided herein relates to food or food products obtained, derived, or processed from one or more embodiments of the nonhuman transgenic animals described herein, wherein the nonhuman transgenic animals carry a first heterologous gene that converts saturated fat and/or carbohydrates to n-6 fatty acids and a second heterologous gene that converts at least one n-6 fatty acid to one or more n-3 fatty acids. In one embodiment, the first heterologous gene can comprise a fat-2 gene. In one embodiment, the second heterologous gene can comprise a fat-1 gene. The food product can comprise meat, milk, eggs, tissues, tendons, oil, dairy products (e.g., cheese), and any combinations thereof. In some embodiments, the ratio of n-6 fatty acids to omegat-3 fatty acids in a food product described herein can be about 1:1 or less.

Food products or dietary supplements that include these non-human transgenic animals or a tissue or processed part thereof are also provided herein. The products can be unprocessed (as in the case of whole animals, or whole parts of animals (e.g., joints, knuckles, or organs)) or processed from a slaughtered animal or a part thereof (e.g., the bones, fat, skin, or oils obtained therefrom). Methods of making dietary supplements (e.g., fish-oil capsules) are known in the art and can be applied to the genetically modified or transgenic animals described herein to make dietary supplements. Accordingly, methods of making food products or dietary supplements from an animal described herein (e.g., a transgenic mammal, bird or fish) are also described herein. These methods can be carried out in any manner, including any currently known process, and the source is, or includes, a non-human transgenic animal (or a part thereof), generated as described herein.

As noted, the nucleic acid molecules and/or transgene constructs described herein (including those in which codon usage has been optimized for the host) can be used to generate non-human transgenic animals. Without wishing to be limited, the nucleic acids and/or transgene constructs described herein can be used to genetically modify animals that are farmed or otherwise considered a source of food. The transgenic animals can be generated using techniques known in the art. More specifically, the mammals and fish can be generated using the methods described herein.

In some embodiments, the food or food products (including, e.g., dietary supplements) can be derived from transgenic fish or transgenic bird that is genetically modified to express a heterologous nucleic acid sequence encoding a delta 12 fatty acid desaturase (e.g., fat-2) and a n-3 fatty acid desaturase (e.g., fat-1) or biologically active variants thereof. The transgenic fish can include, but are not limited to, a cod or any fish of the family Gadidae, order Gadiformes; halibut; herring or any fish of the order Clupeiformes; mackerel or any fish in the family Scombridae;

salmon or any fish of the Salmonidae family, including trout; perch or any fish of the family Percidae; shad or any fish of the family Clupeidae; skate or any fish of the family Rajidae; smelt or any fish of the family Osmeridae; sole or any fish of the family Soleidae; tuna or any fish of the family Scombridae, and other fish that are described above and known to those of skill in the art, e.g., zebrafish.

Food or food products (including, e.g., dietary supplements) obtained or derived from the nonhuman transgenic animals described herein (e.g., carrying both fat-2 and fat-1 genes described herein) can be provided to healthy individuals or to those suffering from a deficiency in essential fatty acids (e.g., n-3 fatty acids). Diseases or disorders associated with a deficiency in n-3 fatty acids are known in the art, including, e.g., obesity, diabetes, cancer, heart diseases, inflammatory diseases, neurodegenerative diseases, neuropsychiatric diseases, osteoarthritis, lupus, non-alcoholic fatty liver disease, colitis, and any combinations thereof. Accordingly, methods for treating a condition (e.g., a disease or disorder) associated with a deficiency in n-3 fatty acids are also provided herein. By administering to a subject diagnosed to have or have a risk for a condition (e.g., a disease or disorder) associated with a deficiency in n-3 fatty acids, food or a food product obtained or derived from a nonhuman transgenic animal described herein (e.g., carrying both fat-2 and fat-1 genes), the n-3 fatty acid content of the treated subject can be increased, e.g., by at least about 30% or above, including, e.g., at least about 40%, at least about 50%, at least about 60%, at least about 70%, at least about 80%, at least about 90%, at least about 95% or above, as compared to a subject with a deficiency in n-3 fatty acids without the administration of the food or food product described herein. In some embodiments, the n-3 fatty acid content in a treated subject can be increased, e.g., by at least about 1.1-fold or above, including, e.g., at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold or above, as compared to a subject with a deficiency in n-3 fatty acids without the administration of the food or food product described herein.

In some embodiments, the ratio of the n-6 fatty acid(s) to n-3 fatty acid(s) in the treated subject can be decreased, e.g., by at least about 10% or above, including, e.g., at least about 20%, at least about 30%, at least about 40%, at least about 50%, at least about 60%, at least about 70%, at least about 80%, at least about 90%, at least about 95% or above, as compared to a subject with a deficiency in n-3 fatty acids without the administration of the food or food product described herein.

The subject can be apparently healthy or may have been diagnosed as having or having a risk for disease or disorder, e.g., having cancer (e.g., breast cancer, colon cancer, prostate cancer, liver cancer, cervical cancer, lung cancer, brain cancer, skin cancer, stomach cancer, head and neck cancer, pancreatic cancer, a blood cancer, or ovarian cancer). Thus, the subject may be one who has been diagnosed as having a neurodegenerative disease (e.g., Alzheimer's disease, Parkinson's disease, or Huntington's disease). Other treatable or preventable conditions include an arrhythmia, cardiovascular disease, cancer, an inflammatory disease, an autoimmune disease, a malformation or threatened malformation of the retina or brain, diabetes, obesity, a skin disorder, a renal disease, ulcerative colitis, Crohn's disease, or chronic obstructive pulmonary disease. The subject may also be one who has received or who is scheduled to receive, a transplant comprising a biological organ, tissue, or cell. The method can be carried out by administering to either the subject or the transplant, a nucleic acid molecule described herein.

Further aspects provide methods of increasing n-3 fatty acid content in an animal (e.g., a non-human animal) or a food product derived therefrom. The method comprises feeding a nonhuman transgenic animal described herein that converts carbohydrates and/or saturated fat to n-6 fatty acids and n-3 fatty acids (e.g., a transgenic animal carrying both fat-2 and fat-1 genes described herein) with a composition or diet high in carbohydrates and/or saturated fats. Therefore, the transgenic animal can convert at least a portion (e.g., at least about 30% or more, including, e.g., at least about 40%, at least about 50%, at least about 60%, at least about 70%, at least about 80%, at least about 90%, at least about 95% or more, including up to 100%) of the carbohydrates and/or saturated fat from its diet to n-3 fatty acids.

As used herein, the term "a composition or diet high in carbohydrates and/or saturated fats" refers to a composition or diet in which at least about 50% or more (including, e.g., at least about 60%, at least about 70%, at least about 80%, at least about 90%, at least about 95% or more, including up to 100%) of the total calories is provided by carbohydrates, saturated fats, or a combination of both. In some embodiments, the composition or diet can further comprise protein, minerals, vitamins, fibers, and a combination of two or more thereof. In some embodiments, the composition or diet high in carbohydrates and/or saturated fats can be a no-fat composition or diet. In these embodiments, carbohydrates can be present in an amount that provides about 50% to about 90% of the total calories. In some embodiments, the composition or diet high in carbohydrates and/or saturated fats can comprise carbohydrates in an amount that provides about 40%-60% of the total calories, and saturated fats in an amount that provides about 20%-40% of the total calories.

In some embodiments, the composition or diet high in carbohydrates and/or saturated fats can be a low-PUFA composition or diet. In these embodiments, the composition or diet can have PUFA (e.g., essential fatty acids) in an amount that provides less than 30% or lower of the total calories. In some embodiments, PUFAs can be present in an amount that provides less than 20%, less than 10%, less than 5%, less than 1% or lower of the total calories. In some embodiments, the low-PUFA composition or diet can exclude any PUFA or essential fatty acids.

In some embodiments, upon feeding the transgenic animals with a composition or diet high in carbohydrates and/or saturated fats, the ratio of n-6 fatty acids to the n-3 fatty acids in the transgenic animal or food product derived therefrom can be about 1:1 or less, including, e.g., about 0.75:1 or about 0.5:1.

In some embodiments, at least a portion of the n-6 fatty acids, e.g., converted from the carbohydrates and/or saturated fat in the diet, or directly from the diet, are not converted to n-3 fatty acids. In some embodiments, substantially all of the n-6 fatty acids, e.g., converted from the carbohydrates and/or saturated fat in the diet, or directly from the diet, are converted to n-3 fatty acids.

Methods of determining an effect of n-6 fatty acid(s) and/or n-3 fatty acid(s) on a condition (e.g., a disease or disorder) associated with fat metabolism are also provided herein. In some embodiments, the method comprises (a) inducing in a nonhuman transgenic animal described herein, or cells or tissues derived therefrom described herein, at least one phenotype of a condition (e.g., a disease or disorder) associated with fat metabolism; (b) feeding the nonhuman transgenic animal, or cells or tissues derived therefrom with a composition high in carbohydrates and/or saturated fat; (c) detecting response(s) of the nonhuman transgenic animal, cells or tissues from (b); and (d) comparing the detected response of the nonhuman transgenic animal, cells or tissues with a control, wherein the difference in the response(s) between the nonhuman transgenic animal, cells or tissues, and the control determines an effect of n-6 and/or n-3 fatty acid(s) on the condition.

In some embodiments, a phenotype of a condition (e.g., a disease or disorder) associated with fat metabolism can be induced by modifying at least one gene in the genome of the nonhuman transgenic animal, or cells or tissues derived therefrom, where the gene is associated with the condition. The gene modification can include, e.g., addition, deletion, and/or mutation of the gene of interest. In some embodiments, a phenotype of a condition (e.g., a disease or disorder) associated with fat metabolism can be induced by exposing the transgenic animal, or cells or tissues derived therefrom, to an agent that induces at least one phenotype of the condition. The condition-inducing agent can be a protein, a peptide, a nucleic acid, a drug, a small molecule, radiation, or any combinations thereof.

After feeding the transgenic animal described herein with a composition high in carbohydrates and/or saturated fat, various assays and/or analyses can be used to detect response(s) of the nonhuman transgenic animal described herein can be performed. For example, responses of the nonhuman transgenic animal can comprise expression level of an analyte associated with genomics, metabolomics, lipidomics, or proteomics.

By comparing the detected responses of the nonhuman transgenic animal to a control, an effect of n-6 fatty acid and/or n-3 fatty acid on the condition (e.g., disease or disorder) being studied can be determined. In some embodiments, the control can be a nonhuman transgenic animal described herein, or cells or tissues derived therefrom, that is/are not fed a composition high in carbohydrates and/or saturated fats. In some embodiments, the control can be a nonhuman animal that cannot convert carbohydrates and/or saturated fat to n-6 fatty acids or n-3 fatty acids. In some embodiments, the control can be a wild type nonhuman animal.

In some embodiments, the transgenic animals described herein (e.g., expressing a fat-2- or fat-1-related transgene) can be bred into animals of varying genetic backgrounds, including animals with phenotypes of interest, e.g., obesity, diabetes, angiogenic defects, cardiovascular defects. Such animals are known to the skilled artisan, and, for example, can be found in the Mouse Genome Database (Blake J A, Richardson J E, Bult C J, Kadin J A, Eppig J T, and the members of the Mouse Genome Database Group. 2003. MGD: The Mouse Genome Database. Nucleic Acids Res 31: 193-195; Eppig J T., Blake, J A, Burkhart D L, Goldsmith C W, Lutz C M, Smith C L. 2002. Corralling conditional mutations: a unified resource for mouse phenotypes. Genesis 32:63-65) or the Oak Ridge National Laboratory mutant mouse database.

In alternative embodiments, cells and/or the transgenic animals described herein (e.g., expressing a fat-2- or fat-1-related transgene) can be used in an assay to identify targets that affect fat metabolism that may in turn influence muscle growth, angiogenesis, obesity, insulin sensitivity and/or cardiovascular function.

Some aspects also provide methods for identifying genes and gene products, protein, protein products, lipid, or metabolites regulated by the fat-2- or fat-1-related enzyme, associated with fat metabolism function include identification of mRNAs, functional RNAs, e.g., microRNAs, and/or proteins differentially expressed in transgenic animals described herein. Such methods are known to the skilled artisan and may include methods described below.

Genes and gene products identified by the methods described herein are useful for further characterization in order to examine the effects of the identified genes and gene products on fat metabolism that may be involved in muscle growth and biology, as well as angiogenesis, insulin sensitivity and fat mass reduction/growth.

The genes identified by the methods described herein can be used for the construction of transgenic animals, e.g., knock-out animals, e.g., animals with exogenous and/or heterologous expression, for the identification of muscle secreted factors or the study of muscle growth, angiogenesis, obesity, insulin sensitivity and cardiovascular function. Furthermore, transgenic, including knock-out, animals may be bred to the fat-2 or fat-1 transgenic mouse described herein.

The genes identified by the methods described herein can be analyzed computationally or experimentally for characteristics of interest. In one embodiment, the genes identified as associated with fat metabolism are computationally screened for characteristics identifying the genes as secreted factors, i.e., possession of putative signal sequences and lack of putative transmembrane domains. Any other domain or sequence characteristics of interest, e.g., nucleic acid or amino acid sequence, may be utilized in selecting genes and gene products from the genes and gene products identified by the methods described herein.

Transgenic animal models and/or cells described herein (e.g., expressing a fat-2- or fat-1-related transgene) can also be used to assay test compounds (e.g., a drug candidate) for efficacy on fat metabolism involved in muscle development, muscle growth, obesity, insulin sensitivity and cardiovascular function in test animals, or in samples or specimens (e.g., a biopsy) from the test animals. In some cases, it can be advantageous to measure the markers of muscle growth, obesity, insulin sensitivity and cardiovascular function in samples, blood, which may be obtained from the test animal without sacrifice of the transgenic animal.

Embodiments of various aspects described herein can be defined in any of the following numbered paragraphs:

1. A nonhuman transgenic animal having a genome comprising a first exogenous and/or heterologous nucleic acid molecule operably linked to a promoter, wherein the first exogenous and/or heterologous nucleic acid molecule comprises (i) a nucleotide sequence of SEQ ID NO. 1 or (ii) a nucleotide sequence that is a biologically active variant of SEQ ID NO. 1 and is at least about 70% identical to SEQ ID NO. 1, wherein upon expression of the first exogenous and/or heterologous nucleic acid molecule in the transgenic animal, the transgenic animal produces n-6 from saturated fats and/or carbohydrates.

2. The nonhuman transgenic animal of paragraph 1, wherein the genome further comprises a second exogenous and/or heterologous nucleic acid molecule, the second exogenous and/or heterologous nucleic acid molecule comprises a nucleotide sequence encoding an enzyme that converts an n-6 fatty acid to an n-3 fatty acid, wherein upon expression of the first and second exogenous and/or heterologous nucleic acid molecules in the transgenic animal, the transgenic animal produces n-3 and optionally n-6 from saturated fats and/or carbohydrates.

3. The nonhuman transgenic animal of paragraph 2, wherein the nucleotide sequence encoding an enzyme that converts an n-6 fatty acid to an n-3 fatty is a nucleotide sequence of SEQ ID NO. 2 or (ii) a nucleotide sequence that is a biologically active variant of SEQ ID NO. 2 and is at least about 70% identical to SEQ ID NO. 2.
4. The nonhuman transgenic animal of any of paragraph 1-3, wherein the ratio of n-6 fatty acid to n-3 fatty acid in the transgenic animal is about 1:1 or lower.
5. The nonhuman transgenic animal of any of paragraphs 1-4, wherein the nonhuman transgenic animal is selected from the group consisting of a cow, a mouse, a rat, a pig, a sheep, a goat, a fish, a buffalo, a rabbit, a poultry, and a livestock.
6. The nonhuman transgenic animal of any of paragraphs 1-5, wherein the genome further comprises a gene modification associated with a condition influenced by fat metabolism.
7. The nonhuman transgenic animal of paragraph 6, wherein the gene modification comprises addition, deletion, and/or mutation of a gene associated with a condition influenced by fat metabolism.
8. A food product derived from the nonhuman transgenic animal of any of paragraphs 2-5.
9. The food product of paragraph 8, wherein the food product comprises meat, milk, an egg, dairy products, or any combinations thereof.
10. The food product of paragraph 8 or 9, wherein the ratio of n-6 fatty acid to the n-3 fatty acid in the food product is about 1 or less.
11. A method of increasing n-3 fatty acid content in an animal or a food product derived therefrom comprising feeding a nonhuman transgenic animal of any of paragraphs 2-7 with a diet high in carbohydrates and/or saturated fat, whereby the transgenic animal converts at least a portion of the carbohydrates and/or saturated fat to n-3 fatty acid.
12. The method of paragraph 11, wherein the diet high in carbohydrate and/or saturated fat excludes essential fatty acids.
13. The method of paragraph 11 or 12, wherein at least a portion of the carbohydrates and/or saturated fat is converted to n-6 fatty acid.
14. The method of any of paragraphs 11-13, wherein the ratio of n-6 fatty acid to the n-3 fatty acid in the transgenic animal or food product derived therefrom is about 1 or less.
15. A transgene construct comprising a first exogenous and/or heterologous nucleic acid molecule operably linked to a promoter, wherein the first exogenous and/or heterologous nucleic acid molecule comprises (i) a nucleotide sequence of SEQ ID NO. 1 or (ii) a nucleotide sequence that is a biologically active variant of SEQ ID NO. 1 and is at least about 70% identical to SEQ ID NO. 1, and wherein the promoter at least directs expression of the first exogenous and/or heterologous nucleic acid molecule in an animal cell.
16. The transgene construct of paragraph 15, further comprising a second exogenous and/or heterologous nucleic acid molecule, the second exogenous and/or heterologous nucleic acid molecule comprising a nucleotide sequence encoding an enzyme that converts an n-6 fatty acid to an n-3 fatty acid.
17. The transgene construct of paragraph 16, wherein the nucleotide sequence encoding an enzyme that converts an n-6 fatty acid to an n-3 fatty acid is a nucleotide sequence of SEQ ID NO. 2 or (ii) a nucleotide sequence that is a biologically active variant of SEQ ID NO. 2 and is at least about 70% identical to SEQ ID NO. 2.
18. The transgene construct of paragraph 16 or 17, wherein the second exogenous and/or heterologous nucleic acid molecule is operably linked to the same promoter or a different promoter, wherein said the same promoter or the different promoter directs expression of the second exogenous and/or heterologous nucleic acid in the transgenic animal cell.
19. The transgene construct of any of paragraphs 15-18, wherein the transgenic animal cell is derived from an animal selected from the group consisting of a cow, a mouse, a rat, a pig, a sheep, a goat, a fish, a buffalo, a rabbit, a poultry, and a livestock.
20. A method of treating a condition associated with a deficiency in n-3 fatty acid comprising administering to a subject diagnosed to have or have a risk for, a condition associated with a deficiency in n-3 fatty acid, a food product of any of paragraphs 8-10, wherein the administration of the food product increases the n-3 fatty acid content in the subject, thereby treating the condition.
21. The method of paragraph 20, wherein the condition is selected from the group consisting of obesity, diabetes, cancer, heart diseases, inflammatory diseases, neurodegenerative diseases, neuropsychiatric diseases, osteoarthritis, lupus, non-alcoholic fatty liver disease, colitis, and any combinations thereof.
22. A method of determining an effect of n-3 fatty acid(s) on a condition associated with fat metabolism comprising:
    a. inducing in a nonhuman transgenic animal of any of paragraphs 1-7 at least one phenotype of a condition associated with fat metabolism;
    b. feeding the nonhuman transgenic animal with a diet high in carbohydrates and/or saturated fat;
    c. detecting a response of the nonhuman transgenic animal from (b); and
    d. comparing the detected response of the nonhuman transgenic animal with a control,
wherein the difference in the response between the nonhuman transgenic animal and the control determines an effect of n-3 fatty acid(s) on the condition.
23. The method of paragraph 22, wherein the inducing comprises modifying at least one gene in the genome of the nonhuman transgenic animal, where the at least one gene is associated with the condition.
24. The method of paragraph 23, wherein the at least one gene in the genome is modified by addition, deletion, and/or mutation.
25. The method of any of paragraphs 22-24, wherein the inducing comprises administering to the nonhuman transgenic animal an agent that induces the condition.
26. The method of any of paragraphs 22-25, wherein the control is a nonhuman transgenic animal of the same kind with a diet low in carbohydrates and/or saturated fat.
27. The method of any of paragraphs 22-25, wherein the control is a nonhuman animal that cannot convert carbohydrates and/or saturated fat to at least one or more n-3 fatty acids.
28. The method of any of paragraphs 22-25, wherein the control is a wild-type nonhuman animal.
29. The method of any of paragraphs 22-28, wherein the response of the nonhuman transgenic animal comprises expression level of an analyte associated with genomics, metabolomics, lipidomics, or proteomics.

Some Selected Definitions

Unless defined herein, terms used herein have their ordinary meanings, and can be further understood in the context of the specification.

As used herein, the term "operably linked," refers to a functional relationship between two or more nucleic acid (e.g., DNA) segments: for example, a promoter or enhancer is operably linked to a coding sequence if it stimulates the transcription of the sequence in an appropriate host cell or other expression system. Generally, sequences that are operably linked are contiguous. However, enhancers need not be located in close proximity to the coding sequences whose transcription they enhance. Furthermore, a gene transcribed from a promoter regulated in trans by a factor transcribed by a second promoter may be said to be operably linked to the second promoter. In such a case, transcription of the first gene is said to be operatively linked to the first promoter and is also said to be operably linked to the second promoter.

As used herein, the term "conversion efficiency" refers to the efficiency and/or the amount by which an enzyme (e.g., a desaturase) can convert a substrate to a product. The conversion efficiency is measured according to the following formula: ([product amount]/[original substrate amount])*100. In some embodiments, the product can include the immediate product and all products in the pathway derived from it.

As used herein, the term "delta 12 fatty acid desaturase" refers to an enzyme that can convert carbohydrates and/or saturated fats to n-6 fatty acids, or a biologically active variant thereof as defined herein. An exemplary delta 12 fatty acid desaturase is an enzyme encoded by fat-2 gene or a biologically active variant thereof, e.g., derived from *C. elegans*.

As used herein, the term "n-3 fatty acid desaturase" refers to an enzyme that can convert n-6 fatty acids to n-3 fatty acids, or a biologically active variant thereof as defined herein. An exemplary n-3 fatty acid desaturase is an enzyme encoded by fat-1 gene or a biologically active variant thereof, e.g., derived from *C. elegans*.

The term "expression" as used herein refers to the transcription and stable accumulation of sense (mRNA) or antisense RNA derived from nucleic acid molecules (e.g., the first and/or second exogenous and/or heterologous nucleic acid molecules described herein). Expression can also refer to translation of mRNA into a polypeptide.

The term "nucleic acid" is well known in the art. A "nucleic acid" as used herein generally refers to a molecule (i.e., strand) of DNA, RNA or a derivative or analog thereof, comprising a nucleobase. A nucleobase includes, for example, a naturally occurring purine or pyrimidine base found in DNA (e.g. an adenine "A," a guanine "G." a thymine "T" or a cytosine "C") or RNA (e.g. an A, a G. an uracil "U" or a C). The term "nucleic acid" encompasses the terms "oligonucleotide" and "polynucleotide," each as a subgenus of the term "nucleic acid." The term "oligonucleotide" refers to a molecule of between about 3 and about 100 nucleobases in length. The term "polynucleotide" refers to at least one molecule of greater than about 100 nucleobases in length. The term "nucleic acid" also refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides. The terms "polynucleotide sequence" and "nucleotide sequence" are also used interchangeably herein.

As used herein, the term "gene" refers to a nucleic acid comprising an open reading frame encoding a polypeptide, including both exon and (optionally) intron sequences. A "gene" refers to coding sequence of a gene product, as well as non-coding regions of the gene product, including 5'UTR and 3'UTR regions, introns and the promoter of the gene product. These definitions generally refer to a single-stranded molecule, but in specific embodiments also encompass an additional strand that is partially, substantially or fully complementary to the single-stranded molecule. Thus, a nucleic acid may encompass a double-stranded molecule or a double-stranded molecule that comprises one or more complementary strand(s) or "complement(s)" of a particular sequence comprising a molecule. As used herein, a single stranded nucleic acid may be denoted by the prefix "ss", a double stranded nucleic acid by the prefix "ds", and a triple stranded nucleic acid by the prefix "is." The term "gene" refers to the segment of DNA involved in producing a polypeptide chain, it includes regions preceding and following the coding region as well as intervening sequences (introns) between individual coding segments (exons). A "promoter" is a region of a nucleic acid sequence at which initiation and rate of transcription are controlled. It may contain elements at which regulatory proteins and molecules may bind, such as RNA polymerase and other transcription factors, to initiate the specific transcription of a nucleic acid sequence. The term "enhancer" refers to a cis-acting regulatory sequence involved in the transcriptional activation of a nucleic acid sequence. An enhancer can function in either orientation and may be upstream or downstream of the promoter.

The term "entity" refers to any structural molecule or combination of molecules.

The term "subject" as used herein refers to human and non-human animals. The term "non-human animals" as used herein includes all vertebrates, e.g., mammals, such as non-human primates, (particularly higher primates), sheep, dog, rodent (e.g. mouse or rat), guinea pig, goat, pig, cat, rabbits, cows, and non-mammals such as chickens, amphibians, reptiles etc. In some embodiments, the non-human animals are non-human mammals. In one embodiment, the subject is human. In another embodiment, the subject is an experimental animal or animal substitute as a disease model. The term does not denote a particular age or sex. Thus, adult and newborn subjects, as well as fetuses, whether male or female, are intended to be covered. Examples of subjects include humans, dogs, cats, cows, goats, and mice. The term subject is further intended to include transgenic species.

The term "tissue" is intended to include intact cells, blood, blood preparations such as plasma and serum, bones, joints, muscles, smooth muscles, and organs.

The term "disease" or "disorder" is used interchangeably herein, refers to any alternation in state of the body or of some of the organs, interrupting or disturbing the performance of the functions and/or causing symptoms such as discomfort, dysfunction, distress, or even death to the person afflicted or those in contact with a person. A disease or disorder can also related to a distemper, ailing, ailment, amlady, disorder, sickness, illness, complaint, inderdisposion, affection.

As used herein, the term "treating" includes reducing or alleviating at least one adverse effect or symptom of a condition, disease or disorder associated with inappropriate proliferation, for example cancer.

As used herein, the terms "administering," and "introducing" are used interchangeably herein and refer to the placement of agents into a subject by a method or route which results in at least partial localization of the agents at a desired site. The agents can be administered by any appropriate route which results in an effective treatment in the subject.

As used herein, a "promoter" or "promoter region" or "promoter element" used interchangeably herein, refers to a segment of a nucleic acid sequence, typically but not limited to DNA or RNA or analogues thereof, that controls the transcription of the nucleic acid sequence to which it is operatively linked. The promoter region includes specific sequences that are sufficient for RNA polymerase recognition, binding and transcription initiation. This portion of the promoter region is referred to as the promoter. In addition, the promoter region includes sequences which modulate this recognition, binding and transcription initiation activity of RNA polymerase. These sequences may be cis-acting or may be responsive to trans-acting factors. Promoters, depending upon the nature of the regulation may be constitutive or regulated.

The term "regulatory sequences" is used interchangeably with "regulatory elements" herein refers element to a segment of nucleic acid, typically but not limited to DNA or RNA or analogues thereof, that modulates the transcription of the nucleic acid sequence to which it is operatively linked, and thus act as transcriptional modulators. Regulatory sequences modulate the expression of gene and/or nucleic acid sequence to which they are operatively linked. Regulatory sequence often comprise "regulatory elements" which are nucleic acid sequences that are transcription binding domains and are recognized by the nucleic acid-binding domains of transcriptional proteins and/or transcription factors, repressors or enhancers etc. Typical regulatory sequences include, but are not limited to, transcriptional promoters, inducible promoters and transcriptional elements, an optional operate sequence to control transcription, a sequence encoding suitable mRNA ribosomal binding sites, and sequences to control the termination of transcription and/or translation.

Regulatory sequences can be a single regulatory sequence or multiple regulatory sequences, or modified regulatory sequences or fragments thereof. Modified regulatory sequences are regulatory sequences where the nucleic acid sequence has been changed or modified by some means, for example, but not limited to, mutation, methylation etc.

The articles "a" and "an" are used herein to refer to one or to more than one (i.e., to at least one) of the grammatical object of the article.

For convenience, certain terms employed in the entire application (including the specification, examples, and appended claims) are collected here. Unless defined otherwise, all technical and scientific terms used herein have the same meaning as commonly understood by one of ordinary skill in the art to which this invention belongs.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used to described the present invention, in connection with percentages means±5%.

In one aspect, the present invention relates to the herein described compositions, methods, and respective component(s) thereof, as essential to the invention, yet open to the inclusion of unspecified elements, essential or not ("comprising"). In some embodiments, other elements to be included in the description of the composition, method or respective component thereof are limited to those that do not materially affect the basic and novel characteristic(s) of the invention ("consisting essentially of"). This applies equally to steps within a described method as well as compositions and components therein. In other embodiments, the inventions, compositions, methods, and respective components thereof, described herein are intended to be exclusive of any element not deemed an essential element to the component, composition or method ("consisting of").

All patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents

EXAMPLES

The following examples illustrate some embodiments and aspects of the inventions described herein. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

Example 1. Generation of Transgenic Animals that can Produce Essential n-6 and n-3 Polyunsaturated Fatty Acids (PUFA) from Non-Essential Nutrients To eliminate the need for fatty acid supplementation, animal models capable of producing essential n-6 and n-3 PUFA from non-essential nutrients were generated. In some embodiments, the transgenic animal model is a murine model. An example approach of making such transgenic murine model was to first create fat-2 transgenic mice, possessing the *C. elegans* fat-2 gene (or variants thereof) encoding an enzyme that converts monounsaturated fatty acids (MUFA) into n-6 linoleic acid (18:2n-6, LA) (17), and then cross the fat-2 transgenic mice with fat-1 transgenic mice, which were generated previously to possess the *C. elegans* fat-1 gene (or variants thereof), encoding an enzyme that converts n-6 to n-3 PUFA (18). Through this approach, a compound fat-1/fat-2 transgenic mouse—hereafter referred to as the "Omega" mouse—was generated. The "Omega" mouse is capable of producing both n-6 and n-3 PUFA from a diet containing only saturated fat and/or carbohydrates (FIG. 1A).

To enable the higher expression of the *C. elegans* fat-2 gene in mammals, the codon of the fat-2 sequence was first optimized based on a mammalian desaturase sequence, and a promoter, e.g., a chicken beta-actin promoter, was utilized to build a transgene construct. The optimized fat-2 sequence used in this Example is SEQ ID NO. 1. The transgene construct was then applied to a mouse, e.g., by microinjection, to create the fat-2 transgenic mouse. After the transgenic mice were evaluated for showing fat-2 phenotype and genotype, the heterozygous fat-2 transgenic mice were backcrossed with wild-type mice (e.g., C57BL6 wild-type (WT) mice) for a number of generations (e.g., ~5 generations), and then crossbred with heterozygous fat-1 transgenic mice. The resulting offspring consisted of WT, fat-1, fat-2, and Omega mice. The fat-1 transgenic mouse has been previously described (12, 19). The genotypes and phenotypes of the WT, fat-2, and Omega littermates were evaluated. Expression of the fat-1 and fat-2 transgenes was determined by PCR. The WT mice do not express any of the fat-1 or fat-2 transgenes. The fat-2 mice carry only the fat-2 transgene, and the Omega mice express both the fat-1 and fat-2 transgenes (FIG. 1B).

When WT, fat-2, and Omega mouse littermates were fed the same diet high in saturated fat and carbohydrates and low in n-6 PUFA, phenotype determination, e.g., by gas chromatography (GC), showed three distinct tissue fatty acid profiles (FIGS. 1C and 1D). The WT mice exhibited high levels of saturated fat and very low levels of essential fatty acids, primarily n-6 PUFA, with an n-6/n-3 PUFA ratio of approximately 3.5. The fat-2 transgenic mice displayed a significant increase in total tissue PUFA content, with the n-6 PUFA content in the muscle tissue doubling from about 700 ug/g to 1350 ug/g due to the conversion of oleic acid into n-6 linoleic acid (LA) and arachidonic acid (AA), without much change in n-3 PUFA levels, resulting in an n-6/n-3 PUFA ratio of about 5. The Omega transgenic mice also exhibited significantly increased total PUFA content, but the tissue content of n-3 PUFA was increased by approximately five-fold compared to their WT and fat-2 littermates, due to the conversion of almost half the n-6 PUFA content into n-3 PUFA, with a markedly decreased n-6/n-3 PUFA ratio of 0.75 (FIG. 1D). MUFA levels were accordingly reduced in the fat-2 and Omega mice, showing that n-6 PUFA had been converted from MUFA. No significant differences in saturated fatty acids (SFA) levels were detected among the three phenotypes. Table 1 on the next page shows comparison of the fatty acid profile in various tissues among the three genotypes.

TABLE 1

Comparison of the fatty acid profile in various tissues among the three genotypes.

| | | SFA | MUFA | Total PUFA | n-6 PUFA | n-3 PUFA | n-6/n-3 |
|---|---|---|---|---|---|---|---|
| Muscle | WT | 38.96 ± 0.98 | 42.87 ± 1.99 | 18.19 ± 1.34 | 14.23 ± 1.59 | 3.96 ± 0.48 | 3.59 ± 0.95 |
| | Fat-2 | 41.15 ± 2.02 | 29.71 ± 2.13 | 29.01 ± 0.01 | 24.29 ± 1.29 | 4.72 ± 1.30 | 5.15 ± 1.33 |
| | Omega | 41.08 ± 0.47 | 33.03 ± 2.12 | 25.9 ± 1.95 | 11.23 ± 2.43 | 14.67 ± 2.09 | 0.78 ± 0.24 |
| | WT vs Fat-2 | n.s. | *** | *** | *** | n.s. | *** |
| | WT vs Omega | n.s. | ** | *** | n.s. | *** | *** |
| | Fat-2 vs Omega | n.s. | n.s. | n.s. | *** | *** | * |
| Liver | WT | 36.70 ± 1.81 | 48.78 ± 1.62 | 13.44 ± 1.32 | 11.86 ± 1.33 | 2.57 ± 0.07 | 4.61 ± 0.96 |
| | Fat-2 | 37.33 ± 2.25 | 33.87 ± 3.05 | 28.82 ± 1.55 | 25.03 ± 1.69 | 3.78 ± 0.29 | 6.65 ± 0.82 |
| | Omega | 37.90 ± 2.09 | 34.21 ± 3.75 | 27.9 ± 2.50 | 17.38 ± 1.76 | 10.52 ± 0.74 | 1.65 ± 0.05 |
| | WT vs Fat-2 | n.s. | ** | *** | *** | ** | * |
| | WT vs Omega | n.s. | ** | *** | * | *** | ** |
| | Fat-2 vs Omega | n.s. | n.s. | n.s. | ** | *** | *** |
| Heart | WT | 40.62 ± 1.23 | 25.62 ± 1.95 | 33.78 ± 2.98 | 27.11 ± 1.72 | 6.67 ± 1.58 | 4.20 ± 0.79 |
| | Fat-2 | 40.73 ± 5.23 | 19.47 ± 3.75 | 39.8 ± 2.06 | 33.58 ± 2.73 | 6.22 ± 0.95 | 5.57 ± 1.42 |
| | Omega | 39.19 ± 2.88 | 21.22 ± 2.88 | 39.6 ± 2.72 | 20.56 ± 3.94 | 19.04 ± 3.33 | 1.12 ± 0.33 |
| | WT vs Fat-2 | n.s. | * | * | * | n.s. | n.s. |
| | WT vs Omega | n.s. | n.s. | * | * | *** | ** |
| | Fat-2 vs Omega | n.s. | n.s. | n.s. | *** | *** | *** |
| Tail | WT | 29.41 ± 1.55 | 62.39 ± 2.19 | 8.20 ± 0.63 | 7.27 ± 0.41 | 0.93 ± 0.23 | 8.07 ± 1.38 |
| | Fat-2 | 33.16 ± 3.42 | 47.65 ± 3.55 | 19.2 ± 1.57 | 17.85 ± 1.50 | 1.35 ± 0.33 | 13.81 ± 3.87 |
| | Omega | 32.79 ± 2.73 | 49.02 ± 2.15 | 18.2 ± 1.18 | 10.16 ± 1.62 | 8.04 ± 0.44 | 1.27 ± 0.27 |
| | WT vs Fat-2 | n.s. | *** | *** | *** | n.s. | n.s. |
| | WT vs Omega | n.s. | *** | *** | n.s. | *** | * |
| | Fat-2 vs Omega | n.s. | n.s. | n.s. | *** | *** | ** |

WT: Wild-type;
SFA: saturated fatty acids;
MUFA: monounsaturated fatty acids;
PUFA: polyunsaturated fatty acids;
n-6: n-6;
n-3: n-3;
n.s.: non-significant.
N = 3 for each group;
* $P < 0.05$,
** $P < 0.01$,
*** $P < 0.001$.

Furthermore, when fed a high-carbohydrate, no-fat diet, the fat-2 and Omega mice still exhibited significant tissue levels of n-6 and n-3 PUFA, respectively, indicating their ability to produce essential fatty acids when lacking dietary fat and given only carbohydrates (Table 2).

TABLE 2

Fatty acid profile of tail tissue in mice fed with the no-fat diet.

|  | SFA | MUFA | Total PUFA | n-6 PUFA | n-3 PUFA | n-6/n-3 |
|---|---|---|---|---|---|---|
| WT | 28.85 ± 7.64 | 64.09 ± 8.13 | 7.06 ± 0.89 | 6.4 ± 0.75 | 0.66 ± 0.14 | 9.93 ± 1.2 |
| Fat-2 | 27.78 ± 1.56 | 57.14 ± 2.01 | 15.1 ± 0.65 | 14.44 ± 0.74 | 0.65 ± 0.09 | 22.44 ± 3.82 |
| Omega | 29.06 ± 3.43 | 56.98 ± 2.65 | 13.97 ± 0.78 | 8.82 ± 0.75 | 5.16 ± 0.28 | 1.71 ± 0.18 |
| WT vs Fat-2 | n.s. | n.s. | *** | *** | n.s. | ** |
| WT vs Omega | n.s. | n.s. | *** | * | *** | * |
| Fat-2 vs Omega | n.s. | n.s. | n.s. | *** | *** | *** |

WT: Wild-type;
SFA: saturated fatty acids;
MUFA: monounsaturated fatty acids;
PUFA: polyunsaturated fatty acids;
n-6: n-6;
n-3: n-3;
n.s.: non-significant.
N = 3 for each group;
* $P < 0.05$,
** $P < 0.01$,
*** $P < 0.001$.

The tissue abundance of n-6 PUFA in the fat-2 mouse and of both n-3 and n-6 PUFA in the Omega mouse, despite the diet containing little of these fatty acids, demonstrates the capability of the transgenic mice to produce essential fatty acids from non-essential nutrients, e.g., MUFA, SFA, and even carbohydrates. This technology permits use of a single diet to create different tissue levels of essential fatty acids, so that the specific effects of different fats on health conditions can be evaluated without confounding factors of diet.

Example Methods for Generation of the Transgenic Animals as Described Above

Codon Optimization:

In order to efficiently express a gene from the lower-life C. elegans in mammals in vivo, the codon usage by C. elegans is adjusted to match those used by mammals. The fat-2 gene sequence was obtained from the gene bank (GenBank accession number NM_070159). Mammalian desaturases as well as the previously optimized fat-1 gene were used as references to determine the differences in codon usages of desaturases between C. elegans and mammals. The codon was then manually adjusted to achieve over 80% optimization. An example optimized Fat-2 sequence is a nucleotide sequence of SEQ ID NO. 1.

Figure 5:
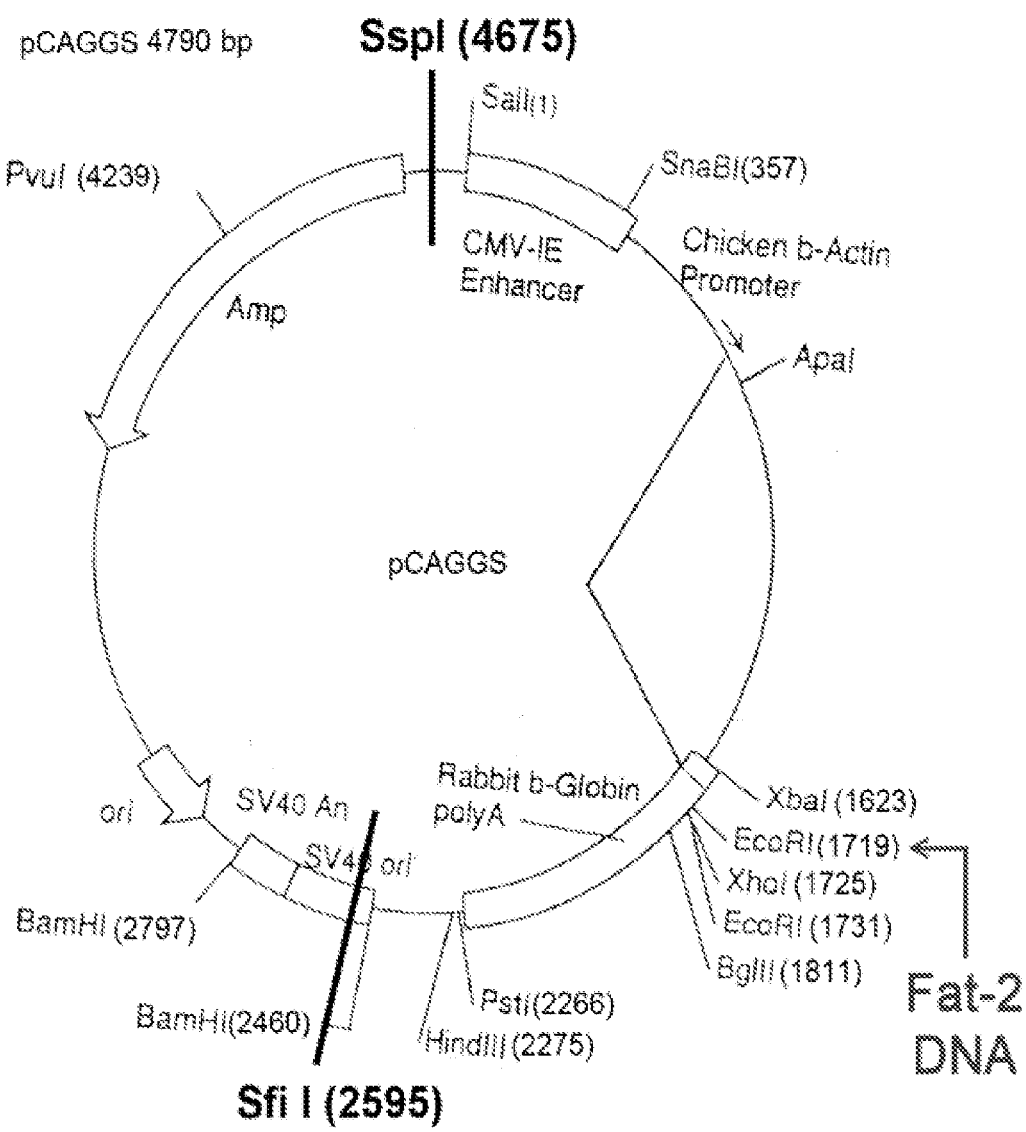
FIG. 5 is a schematic diagram showing the pCAGGS plasmid containing a fat-2 construct, which can be used, e.g., for microinjection, to generate Fat-2 transgenic animals.

Gene Synthesis:

After modifying the gene sequence to optimize the codon usage, the fat-2 gene was synthesized, e.g., by GenScript (Piscataway, N.J.). The gene was synthesized to be flanked with restriction sites, e.g., EcoR I digestion sites, and delivered on a plasmid or vector, e.g., pUC57 plasmid. After amplification, the fat-2 sequence was inserted into an expression plasmid containing a promoter and a control element. In one embodiment, the fat-2 sequence was inserted into a pCAGGS expression plasmid containing the chicken beta-actin promoter and cytomegalovirus enhancer. After ligation, the orientation was confirmed and the plasmid was amplified. Finally, the fragment containing the promoter, the fat-2 sequence, and the polyA sequence was excised with appropriate restriction endonucleases, e.g., SspI and Sfi I, for microinjection (FIG. 5).

Microinjection:

Transgenic animal lines were produced by injecting the purified, digested fragments (e.g., digestion by Ssp I and Sfi I) into fertilized eggs of an animal of interest, e.g., fertilized eggs of C57BL/6×C3H mice. The DNA-injected eggs were transplanted to pseudo-pregnant animals (e.g., B6C3F1 mice) to produce transgenic animals (e.g., transgenic mice). The founder transgenic mice were then subjected to genotyping and phenotyping.

Genotyping and Phenotyping:

Genotyping was carried out by removing a tissue of the transgenic animal (e.g., the tip of the mouse tail) to acquire a DNA sample for RT-PCR, which was performed with the following primers:fat-2 forward, GCGGCCA GACCCA-GACCATC; and fat-2 reverse, GGGCGAC GTGACCGT-TGGTA. PCR products were run through gel electrophoresis on 2% agarose gel. Phenotyping by fatty acid composition analysis using gas chromatography (GC) was performed as previously described in Ref. 26. The fat-2 mice were maintained after weaning on a low-PUFA diet (Table 3).

TABLE 3

Compositions of the low-PUFA diet and the no-fat diet.
(PUFA: polyunsaturated fatty acids.)

|  | Low-PUFA diet | No-fat diet |
|---|---|---|
| Protein (kcal %) | 16.8 | 18.6 |
| Carbohydrates (kcal %) | 51.4 | 81.4 |
| Fat (kcal %) | 31.8 | 0.0 |
| Protein (g) | 18.4 | 16.8 |
| Casein | 18.1 | 16.5 |
| DL-Methionine | 0.3 | 0.3 |
| Carbohydrates (g) | 56.4 | 73.5 |
| Corn starch | 24.3 | 31.6 |
| Sucrose | 32.1 | 41.9 |
| Fat (g) | 15.5 | 0 |
| Coconut oil | 5.2 | 0 |
| Beef tallow | 10.3 | 0 |
| Cellulose | 5 | 5 |
| Mineral Mix S10001 | 3.5 | 3.5 |
| Vitamine Mix V10001 | 1 | 1 |
| Choline Bitartrate | 0.2 | 0.2 |
| Total | 100 | 100 |
| kcal/g | 4.39 | 3.61 |

GC was carried out after 20 days on the diet to allow for clearer phenotypes. Tissue samples (e.g., tail tissue samples) were ground to powder under liquid nitrogen and subjected to total lipid extraction and fatty acid methylation by heating at ~100° C. for ~1 h under ~14% boron trifluoride (BF3)-methanol reagent (Sigma-Aldrich, St. Louis, Mo.) and hexane (Sigma-Aldrich) (26). Fatty acid methyl esters were analyzed by GC using a fully automated 6890N Network GC System (Agilent Technologies, Santa Clara, Calif.) equipped with a flame-ionization detector. Peaks of resolved fatty acids were identified by comparison with fatty acid standards (Nu-chek Prep, Elysian, Minn.), and area percentages for all resolved peaks were analyzed using GC ChemStation Software (Agilent).

After identifying the genotype and phenotype, the fat-2 mice were mated with wild-type (WT) animals (e.g., C57BL6 mice) to create the F1 generation. The F1 generation was then backcrossed with WT animals (e.g., WT C57BL6 mice) at least 5 times in order to verify that the gene is transmittable as well as to establish a pure background, so that fat-2 lines could be maintained with a significant phenotype. Each generation was subjected to genotyping by RT-PCR and phenotyping by GC.

Generation of Omega Mice:

The compound fat-1/fat-2 transgenic mice were created by crossbreeding heterozygous fat-2 transgenic mice with heterozygous fat-1 transgenic mice, which were previously described in Ref. 18 and U.S. Pat. No. 7,238,851, the content of which is incorporated herein by reference. After weaning, the offspring were maintained either on low-PUFA diet or a no-fat diet (Table 3 as shown above), and then genotyped by RT-PCR and phenotyped by GC. Genotyping by RT-PCR of the Omega mice was carried out with the following primers: fat-1 forward, TGTTCATGCCTTCT TCTTTTTCC; fat-1 reverse, GCGACCATACC TCAAACTTGGA; fat-2 forward, GCGGCCA GACCCAGACCATC; fat-2 reverse, GGGCGAC GTGACCGTTGGTA. Phenotyping by fatty acid composition analysis using GC was performed as previously described in Ref. 26.

Example 2. Characterization and Utility of Transgenic Animals that can Produce Essential n-6 and n-3 Polyunsaturated Fatty Acids (PUFA) from Non-Essential Nutrients To illustrate the utility of the transgenic animals to study a condition, e.g., associated with fat metabolism, the transgenic mice described in Example 1, namely WT mice, fat-2 transgenic mice and Omega mice, were examined using several parameters that are commonly linked to the development of metabolic disease.

Figures 2A, 2B, 2C:
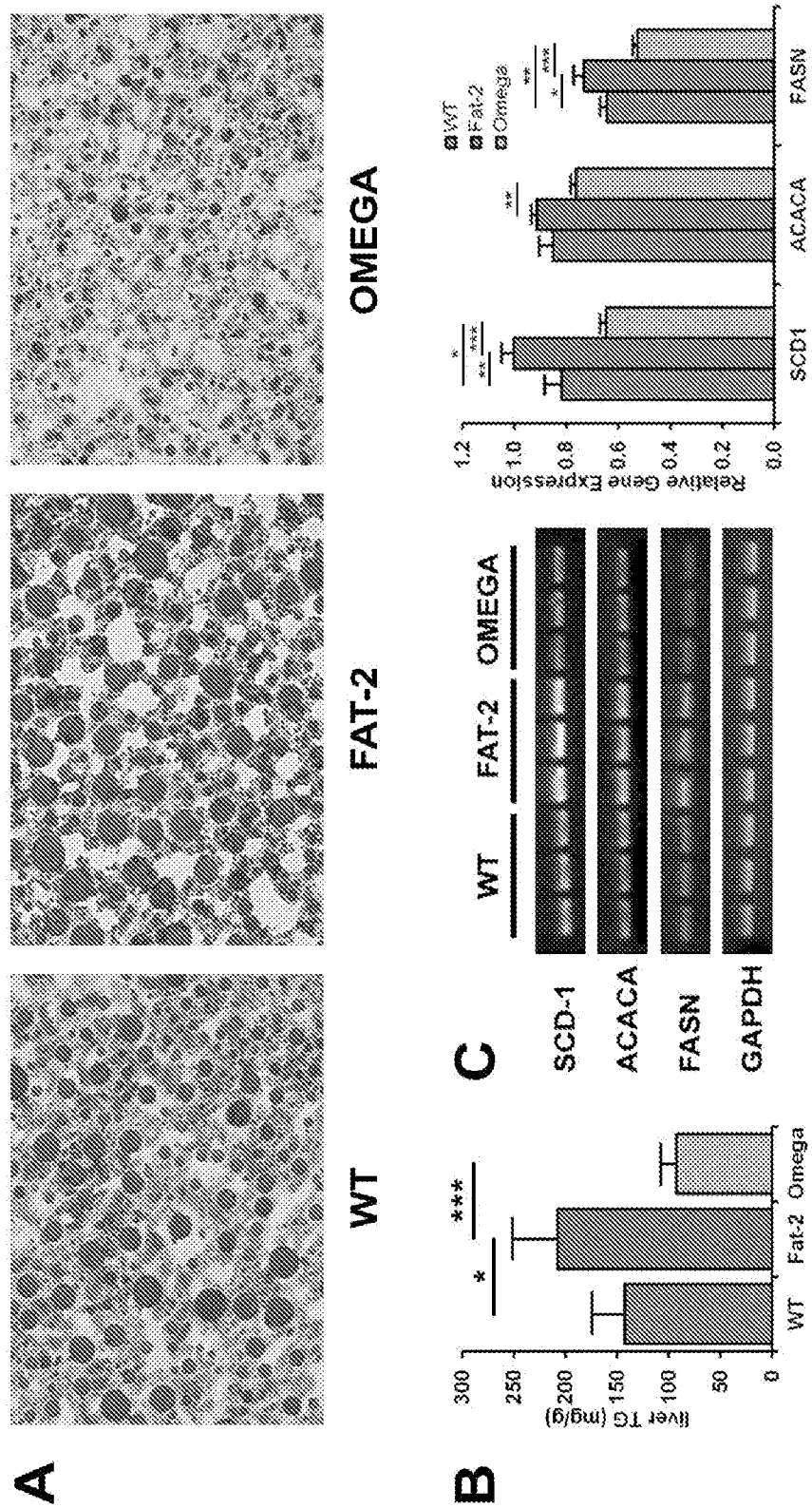
FIG. 2A-2C are experimental data showing that hepatic lipogenesis is markedly increased in fat-2 mice and decreased in Omega mice. The three groups of mice were fed with the same diet high in SFA and carbohydrates and low in n-6 PUFA for about two months, and then liver samples were subjected to analysis.

Increased hepatic lipogenesis is the pathological basis for fatty liver, which is associated with metabolic diseases including obesity, diabetes, and cancer (4). To assess the difference in hepatic lipogenesis among different fatty acid profiles, hepatic lipid content was analyzed. Oil red O staining showed striking differences in lipid accumulation among the three phenotypes; specifically, the fat-2 mice with increased tissue n-6 PUFA exhibited significantly more lipid accumulation compared to its WT littermates, while in the Omega mice with increased tissue n-3 PUFA and a balanced n-6/n-3 PUFA ratio, lipid accumulation was markedly reduced (FIG. 2A). Accordingly, measurement of hepatic triglyceride (TG) content showed a similar pattern, with the greatest amount in the fat-2 mice and the lowest amount in the Omega mice (FIG. 2B). Expression of key lipogenesis-related genes, including, e.g., but not limited to, stearoyl-CoA desaturase-1 (SCD-1), fatty acid synthase (FAS), and acetyl-CoA carboxylase (ACC), were elevated in the fat-2 mice but lowered in the Omega mice (FIG. 2C). These results show the differential effects of n-6 and n-3 PUFA on hepatic lipogenesis.

Figure 3A:
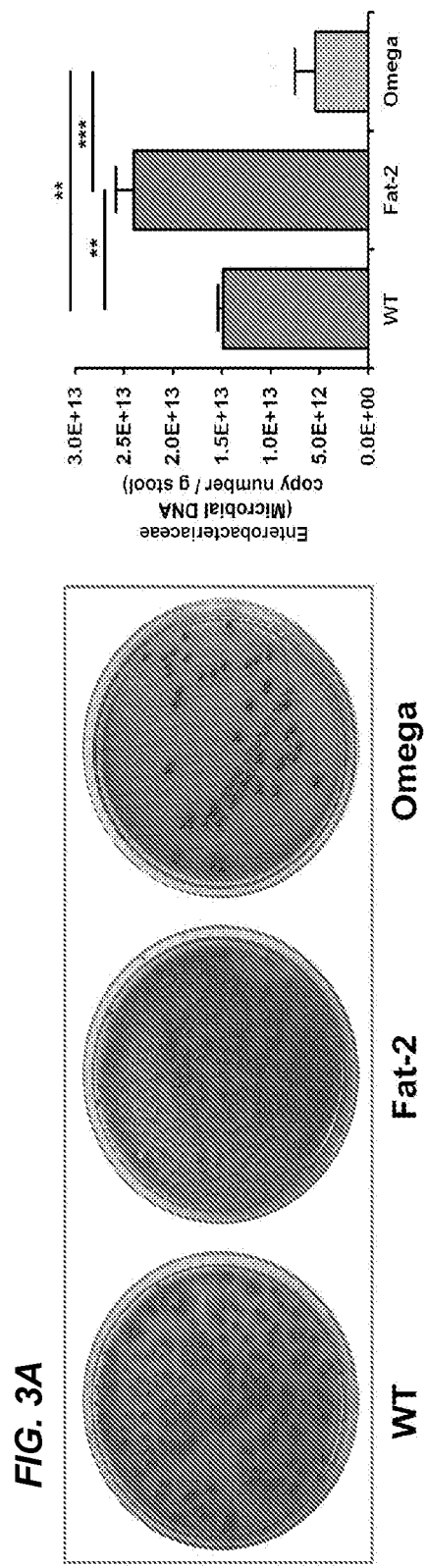
FIGS. 3A-3B are experimental data showing changes in gut microbiota composition with different tissue fatty acid profiles.
Figure 3B:
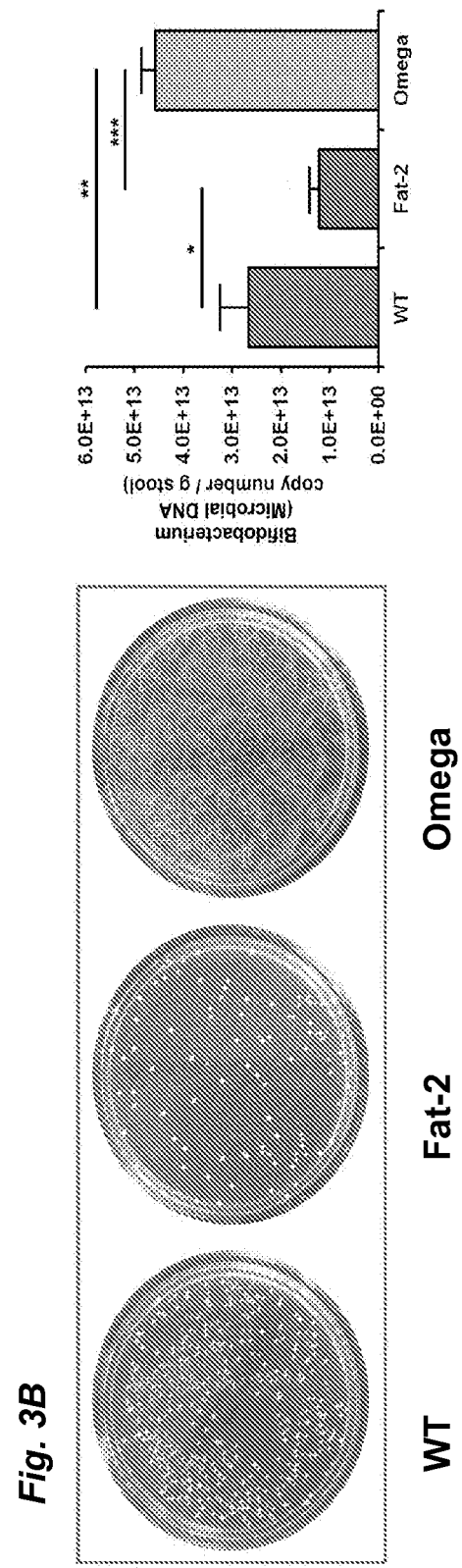

The gut microbiota has been recognized as a critical determinant of numerous physiological and pathological conditions associated with metabolic disease (5). Increased levels of Enterobacteriaceae and decreased levels of *Bifidobacterium* have been linked to endotoxemia-induced low-grade inflammation (20, 21). Accordingly, these two gut microbial species were selected to evaluate how they might be affected by changes in tissue fatty acid profile, through stool culture and PCR measurement of stool bacteria DNA. Remarkably, although the three groups of mice were all fed with an identical diet, the present findings showed that each group exhibited a distinct gut microbiota composition associated with their respective fatty acid profile. As shown in FIG. 3A, Enterobacteriaceae population numbers were increased in the fat-2 mice, but significantly reduced in the Omega mice. In contrast, FIG. 3B shows that *Bifidobacterium* population numbers exhibited the opposite trend, with a greatly reduced presence in the fat-2 mice but elevated in the Omega mice. Previous reports on the impact of diet on gut microbiota have largely attributed the effects to the direct interaction of dietary components in the intestinal lumen with the gut microbiota (22); however, the present findings that three distinct gut microbiota profiles can be created from a single diet show for the first time that these differences can be induced solely due to changes in tissue fatty acid composition. The experimental system or transgenic mice as presented herein thus provides a unique opportunity to explore the interactions between host tissue content and the gut microbiome.

Figure 4A:
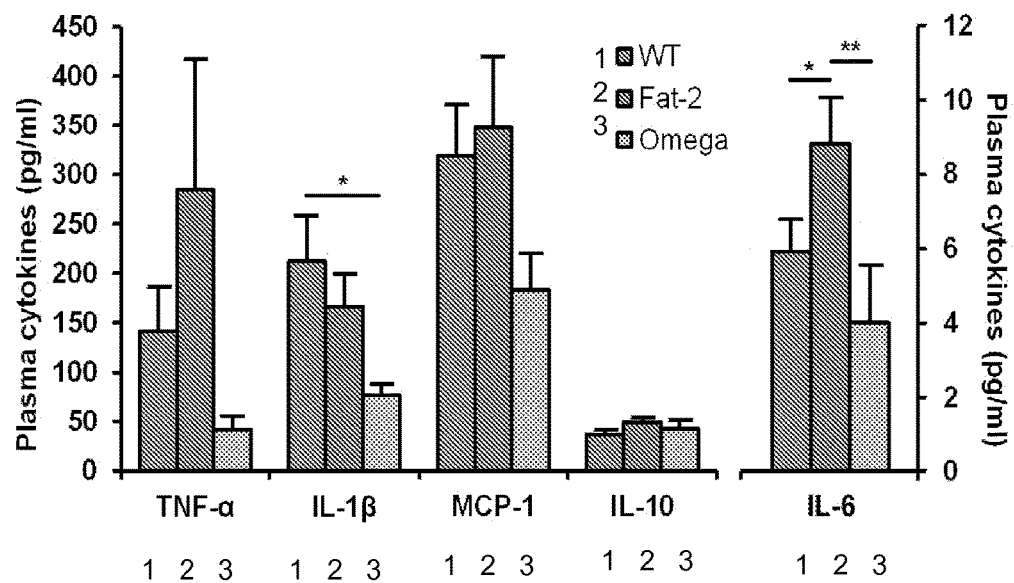
FIGS. 4A-4B are bar graphs showing differential status of low-grade chronic inflammation among the three phenotypes with different tissue fatty acid profiles.
Figure 4B:
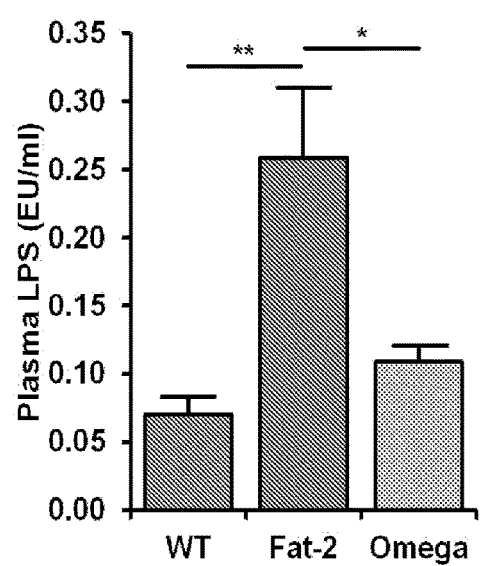

Chronic low-grade inflammation is a common mechanism for many diseases and is primarily characterized by increased plasma levels of inflammatory cytokines, including, e.g., but not limited to, TNF-$\alpha$, IL-1$\beta$, and IL-6 (6, 7, 23). Using multiplex assay, plasma levels of several key inflammatory cytokines were measured. TNF-$\alpha$ and IL-6 levels were found to be significantly different among the three groups, with the highest levels in the fat-2 mice and the lowest levels in the Omega mice (FIG. 4A). As low-grade inflammation can often be induced by gut bacteria-derived plasma endotoxins, such as lipopolysaccharides (LPS) (24, 25), the plasma levels of LPS were measured. As shown in FIG. 4B, LPS levels were the highest in the fat-2 mice and lowest in the Omega mice, consistent with the gut microbiota profile and the inflammatory cytokine levels as shown above. The findings presented herein indicate a potential new mechanism for which alteration of tissue n-6 or n-3 PUFA levels affects low-grade inflammation through modulation of the gut microbiota and related endotoxemia. Together, these findings show that low-grade inflammation is promoted by higher tissue n-6 PUFA levels, but suppressed by increasing tissue n-3 PUFA levels and balancing the tissue n-6/n-3 PUFA ratio.

The Western human diet today is fundamentally different from what it was throughout the majority of human evolution. Among the many shifts in dietary nutrients that have occurred over the last few decades, some key changes include increases in saturated fat, carbohydrates, and n-6 PUFA intake with a decrease in n-3 PUFA intake (1, 2). As a result, modern humans have an n-6 to n-3 PUFA ratio that favors n-6 PUFA by as much as 20:1; evolutionarily, this ratio would have been closer to 1:1, and the discrepancy is believed to have profound physiological consequences (1, 2). At the same time, chronic low-grade inflammation has become a common affliction associated with the rising prevalence of chronic metabolic diseases such as diabetes, obesity, heart disease, and cancer (6, 7). However, it remains debatable whether there is truly a link between the shift in dietary composition, especially the n-6/n-3 PUFA ratio, and the prevalence of low-grade inflammation, and thereby the health epidemics of today.

The present findings using a well-controlled experimental system as described herein provide evidence for this link. In this Example, all mice were fed with a diet high in saturated fat and carbohydrates and low in n-6 PUFA. Although the only difference between the WT mice and the fat-2 mice is that the fat-2 mice have elevated tissue n-6 PUFA levels, the fat-2 mice showed the most unfavorable conditions for hepatic lipo genesis, gut microbiota, and inflammatory cytokine levels. These results indicate that when tissue n-6 PUFA is increased in the presence of high saturated fat and low n-3 PUFA, the risk of health complications leading to metabolic disease is much greater. These results also indicate the necessity of taking into consideration the n-6 PUFA content in the interpretation of animal or human studies using high fat diets, given the significant influence of n-6 PUFA levels on their outcome. Thus far, most existing studies have failed to take n-6 PUFA content into account. In addition, previous studies have not been able to isolate the effects of n-6 PUFA from the potential beneficial effects of other components (such as antioxidants or phytosterols) in the oils or supplements used.

The present findings, as seen in the Omega mice, also indicate how one can resolve the health complications caused by increased tissue n-6 PUFA. The fat-2 and Omega mice differ only in that the Omega mice have decreased tissue n-6 levels and increased n-3 PUFA levels. However, the adverse health outcomes observed in the fat-2 mice were largely reduced in the Omega mice. These findings highlighted the importance of n-3 PUFA and a balanced tissue n-6/n-3 PUFA ratio in lowering the risk for a metabolic disease.

The discoveries presented herein have great implications for modern health epidemics. The fat-2 mouse, whose tissue composition closely resembles those of animals consuming the modern Western diet, shows that high tissue levels of n-6 PUFA appear to be one of the causes of today's health epidemics. The Omega mouse shows that increasing tissue n-3 PUFA levels and decreasing n-6 PUFA levels to balance the tissue n-6/n-3 PUFA ratio can be an effective approach to counteract these adverse health conditions. These findings also indicate the evolutionary preference for a balanced n-6/n-3 PUFA ratio for optimal health (1, 2).

Furthermore, the findings presented herein illustrate how these transgenic animal models can be of great utility in elucidating the impact of altering tissue fat composition on disease conditions. The potential applications are apparent when these models are utilized with other diets of interest or different disease conditions, in combination with analytical technologies such as genomics or metabolomics. Such comprehensive data without confounding factors of diet can enable one to better understand nutrient-gene interactions and resolve current uncertainties of the field, as well as identify new targets or approaches for the prevention and treatment of metabolic diseases.

In addition, one aspect presented herein relates to a new transgenic technology that can produce essential fatty acids, especially the beneficial n-3 PUFA, in animal products (such as meat, milk, eggs, etc.) by feeding animals with solely carbohydrates and/or saturated fat. Given that n-3 PUFA are largely limited to marine sources (such as fish and algae), the transgenic technology and transgenic animals as described herein can therefore generate sustainable and accessible n-3 PUFA resources, especially where only carbohydrates and/or saturated fat are available.

Exemplary Methods for Characterization of the Transgenic Animals

Oil Red O Staining:

To determine hepatic lipid accumulation, frozen liver sections (e.g., 10 μm) were fixed in 4% phosphate-buffered paraformaldehyde, stained with Oil Red O (Sigma-Aldrich), and counterstained with hematoxylin (Sigma-Aldrich). The sections were examined by light microscopy and the images were captured using a CCD camera (QImaging, Surrey, Canada).

Measurement of Hepatic Triglyceride (TG) Content:

Liver tissue was extracted with 5% NP-40 and diluted 10-fold with $dH_2O$, and then subjected to TG measurement using a colorimetric assay kit (Sigma-Aldrich, TR0100), following the manufacturer's instructions.

PCR Assay of Gene Expression:

Liver tissue was excised and grinded in liquid nitrogen. Total RNA extraction was performed with TRIzol reagent (Invitrogen Life Technologies, Grand Island, N.Y.), following the manufacturer's instructions. Three μg of RNA from each sample was reverse transcribed into cDNA with an iScript Reverse Transcription Kit (Bio-Rad, Hercules, Calif.). PCR was carried out using a Mastercycler Pro S Thermal cycler (Eppendorff, Hauppauge, N.Y.) with the program: 95° C., 5 min→4 (95° C., 30 sec→58° C., 30 sec→72° C., 30 sec)×35→72° C., 5 min. 10 μl of PCR product was analyzed by 1.5% agarose gel electrophoresis, visualized under UV light and photographed. The density of each band was quantified using Image J software and the relative quantity of each PCR product was calculated as the ratio of band density to that of the housekeeping gene, GAPDH, in the same sample.

Bacteria Culture:

Individual stool samples were collected, for example, directly in Brain Heart Infusion (BHI) media (200 μl) in microfuge tubes and kept on ice. BHI media was added to each tube by a specific weight:volume ratio (e.g., 10 mg sample:100 μl BHI). Samples were vortexed and serially diluted, then plated on agar plates, for example, MacConkey agar (BD, USA) or Bifido agar (Anaerobe Systems, Morgan Hill, Calif.) plates, to enumerate the family Enterobacteriaceae and *Bifidobacterium* species, respectively. MacConkey agar plates were incubated in ambient air for 24 h at 37° C. and Bifido agar plates were incubated in an anaerobic bag (Fisher Scientific) in a 37° C. incubator for 48 hr.

Quantitative PCR (qPCR) Measurement of Bacterial DNA:

Bacterial genomic DNA was extracted from stool samples of 100 g stored at −80° C. using the QIAamp DNA Stool Mini Kit (Qiagen, Valencia, Calif.), following the manufacturer's instructions. DNA concentration was determined by absorbance at 260 nm, and the purity was estimated by determining the A260/A280 ratio with a Nanodrop spectrophotometer (Biotek, Winooski, Vt.). qPCR was performed using SYBR Green in a PRISM 9000 Light Cycler (Applied Biosystems, USA), following the manufacturer's instructions. The following group-specific 16S rRNA gene primers (Invitrogen) were used: family Enterobacteriaceae forward, 5'-GTG CCA GCA GCC GCG GTA A-3'- and reverse, 5'-CCT CAA GGG CAC AAC CTC CAA G-3'-; *Bifidobacterium* species forward, 5'-TCG CGT CCG GTG TGA AAG3'- and reverse, 5'-CCA CAT CCA GCA TCC AC-3'-. Data analysis was performed using MxPro QPCR software (v4.10, Agilent). The bacterial concentration (microbial DNA copy number/gram of stool) of each stool sample was calculated by comparing the Ct values obtained from the standard curves, which were constructed using serial five-fold dilutions of bacterial genomic DNA of known concentration (BEI Resources, Manassas, Va.) from corresponding reference strains (*Escherichia coli* MG1655 and *Bifidobacterium* sp. strain 12147BFAA). The mass for one bacterial genome was calculated by using the Avogadro constant and assuming the mean molecular weight of a base pair to be 660 g/mol. Standard curves were normalized to the copy number of the 16S rRNA gene for each group of bacteria. The 16S rRNA gene copies in each sample were normalized to gram of feces.

Measurement of Plasma Cytokine Levels:

Serum samples were analyzed for levels of TNF-α, IL-1β, IL-6, MCP-1 and IL-10, for example, by Bio-Plex immunoassays formatted on magnetic beads (Bio-Rad), following the manufacturer's instructions. Xponent software (Luminex, Austin, Tex.) was used for data acquisition and analysis.

Measurement of Plasma LPS Concentration:

Plasma LPS concentrations were measured, for example, with a ToxinSensor Chromogenic Limulus Amebocyte Lysate (LAL) Endotoxin Assay Kit (GenScript), following the manufacturer's instructions. For example, samples were diluted 10-fold with endotoxin-free water, adjusted to the recommended pH, and heated for 10 min at 70° C. to minimize inhibition or enhancement by contaminating proteins. LAL reagents were added to serum samples and incubated at 37° C. for 45 min, and the absorbance was read at 545 nm.

Statistical Analysis:

GraphPad Prism 5 (GraphPad Software, San Diego, Calif.) was used for all statistical analyses. Data sets were analyzed by F-test to verify normal distribution. One-way ANOVA followed by the Tukey test was used to determine statistical significance, set at * $P<0.05$,  $P<0.01$, and * $P<0.001$.

REFERENCES

1. Leaf, A. & Weber, P. C. A new era for science in nutrition. *Am. J. Clin. Nutr.* 45, 1048-1053 (1987)
2. Cordain, L. et al. Origins and evolution of the Western diet: health implications for the 21st century. *Am. J. Clin. Nutr.* 81, 341-354 (2005)
3. Institute of Medicine of the National Academies. Dietary fats: total fat and fatty acids. In: Dietary reference intakes for energy, carbohydrate, fiber, fat, fatty acids, cholesterol, protein, and amino acids (macronutrients). Washington, D.C.: The National Academy Press, pp. 335-432 (2002)
4. Borén, J., Taskinen, M. R., Olofsson, S. O., & Levin, M. Ectopic lipid storage and insulin resistance: a harmful relationship. *J. Intern. Med.* 274, 25-40 (2013)
5. Sekirov, I., Russell, S. L., Antunes, L. C., & Finlay, B. B. Gut microbiota in health and disease. *Physiol. Rev.* 90, 859-904 (2010)
6. Hotamisligil, G. S. Inflammation and metabolic disorders. *Nature* 14, 860-867 (2006)
7. Ruiz-Núñez, B., Pruimboom, L., Dijck-Brouwer, D. A., & Muskiet, F. A. Lifestyle and nutritional imbalances associated with Western diseases: causes and consequences of chronic systemic low-grade inflammation in an evolutionary context. *J. Nutr. Biochem.* 24, 1183-1201 (2013)
8. Kuller, L. H. Dietary fat and chronic diseases: epidemiologic overview. *J. Am. Diet. Assoc.* 97, S9-15 (1997)
9. Joint WHO/FAO Expert Consultation. Diet, Nutrition and the Prevention of Chronic Diseases (WHO technical report series 916). World Health Organization, Geneva. pp. 81-94 (2003)
10. Weisburger, J. H. Dietary fat and risk of chronic disease: mechanistic insights from experimental studies. *J. Am. Diet. Assoc.* 97, S16-23 (1997)
11. Simopoulos, A. P. The importance of the n-6/n-3 fatty acid ratio in cardiovascular disease and other chronic diseases. *Exp. Biol. Med.* 233, 674-688 (2008)
12. Kang, J. X. The n-6/n-3 fatty acid ratio in chronic diseases: animal models and molecular aspects. *World. Rev. Nutr. Diet.* 102, 22-29 (2011)
13. Volpe, J. J. & Vagelos, P. R. Mechanisms and regulation of biosynthesis of saturated fatty acids. *Physiol. Rev.* 56, 339-417 (1976)
14. Paton, C. M. & Ntambi, J. M. Biochemical and physiological function of stearoyl-CoA desaturase. *Am. J. Physiol. Endocrinol. Metab.* 297, E28-37 (2009)
15. Leonard, A. E., Pereira, S. L., Sprecher, H., & Huang, Y. S. Elongation of long-chain fatty acids. *Prog. Lipid Res.* 43, 36-54 (2004)
16. Gebauer, S. K., Psota, T. L., Harris, W. S., Kris-Etherton, P. M. n-3 fatty acid dietary recommendations and food sources to achieve essentiality and cardiovascular benefits. *Am. J. Clin. Nutr.* 83, 1526s-1535s (2006)
17. Watts, J. L. & Browse, J. Genetic dissection of polyunsaturated fatty acid synthesis in *Caenorhabditis elegans*. *Proc. Natl. Acad. Sci. USA* 99, 5854-5859 (2002)
18. Kang, J. X., Wang, J., Wu, L., & Kang, Z. B. Transgenic mice: fat-1 mice convert n-6 to n-3 fatty acids. *Nature* 427, 504 (2004)
19. Kang, J. X. Fat-1 transgenic mice: A new model for n-3 research. *Prostaglandins Leuko. Essent. Fatty Acids* 77, 263-267 (2007)
20. Cani, P. D., et al. Selective increases of bifidobacteria in gut microflora improve high-fat-diet-induced diabetes in mice through a mechanism associated with endotoxaemia. *Diabetologia* 50, 2374-2383 (2007)
21. Kim, K. A., Gu, W., Lee, I. A., Joh, E. H., & Kim, D. H. High fat diet-induced gut microbiota exacerbates inflammation and obesity in mice via the TLR4 signaling pathway. *PLoS One* 7, e47713 (2012)
22. Diamant, M., Blaak, E. E., & de Vos, W. M. Do nutrient-gut-microbiota interactions play a role in human obesity, insulin resistance and type 2 diabetes? *Obes. Rev.* 12, 272-281 (2011)
23. Nathan, C. & Ding, A. Nonresolving inflammation. Cell 140, 871-882 (2010)
24. Cani, P. D., et al. Changes in gut microbiota control metabolic endotoxemia-induced inflammation in high-fat diet-induced obesity and diabetes in mice. *Diabetes* 57, 1470-1481 (2008)
25. Moreira, A. P., Texeira, T. F., Ferreira, A. B., Peluzio, Mdo. C., & Alfenas, Rde. C. Influence of a high-fat diet on gut microbiota, intestinal permeability and metabolic endotoxaemia. *Br. J. Nutr.* 108, 801-809 (2012)
26. Kang, J. X. & Wang, J. A simplified method for analysis of polyunsaturated fatty acids. *BMC Biochem.* 6, 5 (2005)

What is claimed is:

1. A transgene construct comprising a nucleic acid molecule encoding a biologically active delta 12 fatty acid desaturase (fat-2) operably linked to a first promoter functional in an animal cell, wherein the biologically active fat-2 is encoded by the nucleic acid sequence of SEQ ID NO: 1 or a nucleic acid sequence that is at least about 90% identical to the nucleic acid sequence of SEQ ID NO: 1.

2. The transgene construct of claim 1, further comprising a second nucleic acid molecule encoding an enzyme that converts an n-6 fatty acid to an n-3 fatty acid.

3. The transgene construct of claim 2, wherein the enzyme that converts an n-6 fatty acid to an n-3 fatty is encoded by a nucleotide sequence of SEQ ID NO. 2 or a nucleotide sequence that is a biologically active variant of SEQ ID NO. 2 and is at least about 90% identical to SEQ ID NO. 2.

4. The transgene construct of claim 2, wherein the first and second promoters are the same or different.

5. The transgene construct of claim 1, wherein the first promoter is functional in a cow, mouse, rat, pig, sheep, goat, fish, buffalo, rabbit, poultry, or livestock.

* * * * *

SEQUENCE LISTING

<160> NUMBER OF SEQ ID NOS: 19

<210> SEQ ID NO 1
<211> LENGTH: 1276
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

| | | | | | |
|---|---|---|---|---|---|
| taaaacttgg | cccccgacga | agatgacaat | cgccacaaaa | gtgaacacaa | ataaaaaga | 60 |
| cctggatacg | atcaaggtgc | cggagctgcc | aagcgtggca | gctgtcaaag | ccgcaatccc | 120 |
| tgagcactgc | tttgtgaagg | atcccttgac | tagcatttca | tatctgatca | aggattacgt | 180 |
| gcttctcgcc | ggtctctact | ttgcagttcc | ctacatagag | cattatctcg | gatggatcgg | 240 |
| gctgcttggc | tggtattggg | ccatgggaat | tgttggctcc | gcattgttct | gtgtggggca | 300 |
| cgactgcgga | cacggatcat | tctccgatta | tgaatggctc | aatgatctgt | gtggccattt | 360 |
| agcccatgct | cctattctgg | ctccgttctg | gccctggcag | aaatctcacc | gccagcatca | 420 |
| ccagtacaca | tcccacgtgg | aaaaggataa | gggacacccc | tgggttactg | aggaagacta | 480 |
| caataatcgc | accgccattg | agaaatattt | cgccgtgatt | ccaattagcg | gatggctgcg | 540 |
| atggaatccc | atctacacca | tcgtcggtct | gcccgatggc | tctcacttct | ggccttggtc | 600 |
| ccggctcttc | gagactaccg | aggatcgtgt | caagtgtgca | gtttctggcg | ttgcatgcgc | 660 |
| tatctgcgct | tacattgcct | ttgtgctctg | cgactattct | gtctacacat | ttgtcaagta | 720 |
| ctactacatt | ccactgctct | tccagggcct | gatcctcgtc | attatcacgt | atcttcaaca | 780 |
| ccagaatgag | gatattgagg | tctacgaagc | cgatgagtgg | ggctttgtac | gcggccagac | 840 |
| ccagaccatc | gacaggcact | ggggcttcgg | actagacaac | atcatgcaca | acattaccaa | 900 |
| cggtcacgtc | gcccatcact | tcttcttcac | caaaatcccc | cactatcatc | tgttggaggc | 960 |
| aactcccgcc | atcaagaaag | ccctggaacc | tctgaaagac | actcagtacg | gatacaaacg | 1020 |
| ggaagtcaac | tacaactggt | tcttcaaata | tctgcactac | aacgtgaccc | tcgactactt | 1080 |
| gacccacaaa | gcaaagggtg | tgctgcagta | ccgcagtggc | gttgaggctg | caaaggctaa | 1140 |
| gaaggcccag | tgaactacaa | aatctcctga | cacgtgttca | tttttttgat | tgccatttta | 1200 |
| tgttataacc | aattttgaat | tgttttttga | aaattaattc | tcacatattt | caatgaaaat | 1260 |
| ttatgtgcta | cttttg | | | | | 1276 |

<210> SEQ ID NO 2
<211> LENGTH: 1391
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

| | | | | | |
|---|---|---|---|---|---|
| caagtttgag | gtatggtcgc | tcattccagc | gaagggctgt | ccgccacggc | tccggtcacc | 60 |
| ggcggcgatg | tgctggtgga | tgcccgtgca | tctctggagg | agaaggaggc | ccccgcgac | 120 |
| gtgaatgcaa | acactaaaca | ggccaccact | gaggagcccc | gcatccagtt | acccactgtg | 180 |
| gatgccttcc | gccgcgcaat | tcccgcacac | tgcttcgaga | gggacctcgt | gaaatcaatc | 240 |
| aggtatctgg | tgcaggactt | tgcggcactg | acaattctgt | actttgccct | tcccgccttt | 300 |
| gagtactttg | gcctgtttgg | ttacctggtg | tggaacattt | ttatgggcgt | ttttggcttc | 360 |

```
gcgctgttcg tcgttggaca cgactgtctt cacggctcat tctccgataa tcagaatctc    420
aatgatttca ttggacatat cgccttcagc ccactcttct ctccctactt ccctggcag    480
aaaagtcaca agctgcacca cgccttcacc aaccacatcg acaaagatca tggacacgtg    540
tggatacagg ataaggattg ggaagcaatg cccagctgga aaagatggtt caatcctatt    600
cctttctctg gctggctgaa atggttccct gtgtacactc tgttcggttt ctgcgatgga    660
tcccacttct ggcctactc ctcactgttt gtgcgcaact ctgaacgcgt tcagtgtgta    720
atctctggaa tctgctgctg tgtgtgcgca tatattgctc taacaattgc tggaagctat    780
tccaattggt tctggtacta ttgggttcca ctttctttct tcggcttgat gctcgtcatt    840
gttacctatc tgcagcacgt cgacgacgtc gctgaggtgt acgaggctga tgaatggagc    900
ttcgtccggg gacagaccca gaccatcgat cgttactatg gcctcggctt ggacacaacg    960
atgcaccata tcacagacgg cacgttgcc caccacttct caacaaaat cccacattac    1020
catctcatcg aagcaaccga aggtgtcaaa aaggtcttgg agccgttgtc cgacacccaa    1080
tacgggtaca atctcaggt gaactacgat ttctttgccc ggttcctgtg gttcaactac    1140
aagctcgact atctcgttca caagaccgcc ggaatcatgc aattccgaac aactctcgag    1200
gagaaggcaa aggccaagtg aaagaatatc ccgtgccgtt ctagagtaca acaacaactt    1260
ctgcgttttc accggttttg ctctaattgc aatttttctt tgttctatat atatttttt    1320
gcttttaat tttattctct ctaaaaaact tctacttttc agtgcgttga atgcataaag    1380
ccataactct t    1391
```

<210> SEQ ID NO 3
<211> LENGTH: 383
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 3

```
Lys Thr Trp Pro Pro Thr Lys Met Thr Ile Ala Thr Lys Val Asn Thr
1               5                   10                  15

Asn Lys Lys Asp Leu Asp Thr Ile Lys Val Pro Glu Leu Pro Ser Val
            20                  25                  30

Ala Ala Val Lys Ala Ala Ile Pro Glu His Cys Phe Val Lys Asp Pro
        35                  40                  45

Leu Thr Ser Ile Ser Tyr Leu Ile Lys Asp Tyr Val Leu Leu Ala Gly
    50                  55                  60

Leu Tyr Phe Ala Val Pro Tyr Ile Glu His Tyr Leu Gly Trp Ile Gly
65                  70                  75                  80

Leu Leu Gly Trp Tyr Trp Ala Met Gly Ile Val Gly Ser Ala Leu Phe
                85                  90                  95

Cys Val Gly His Asp Cys Gly His Gly Ser Phe Ser Asp Tyr Glu Trp
            100                 105                 110

Leu Asn Asp Leu Cys Gly His Leu Ala His Ala Pro Ile Leu Ala Pro
        115                 120                 125

Phe Trp Pro Trp Gln Lys Ser His Arg Gln His Gln Tyr Thr Ser
    130                 135                 140

His Val Glu Lys Asp Lys Gly His Pro Trp Val Thr Glu Glu Asp Tyr
145                 150                 155                 160

Asn Asn Arg Thr Ala Ile Glu Lys Tyr Phe Ala Val Ile Pro Ile Ser
```

```
                165                 170                 175
Gly Trp Leu Arg Trp Asn Pro Ile Tyr Thr Ile Val Gly Leu Pro Asp
            180                 185                 190

Gly Ser His Phe Trp Pro Trp Ser Arg Leu Phe Glu Thr Thr Glu Asp
            195                 200                 205

Arg Val Lys Cys Ala Val Ser Gly Val Ala Cys Ala Ile Cys Ala Tyr
            210                 215                 220

Ile Ala Phe Val Leu Cys Asp Tyr Ser Val Tyr Thr Phe Val Lys Tyr
225                 230                 235                 240

Tyr Tyr Ile Pro Leu Leu Phe Gln Gly Leu Ile Leu Val Ile Ile Thr
                245                 250                 255

Tyr Leu Gln His Gln Asn Glu Asp Ile Glu Val Tyr Glu Ala Asp Glu
                260                 265                 270

Trp Gly Phe Val Arg Gly Gln Thr Gln Thr Ile Asp Arg His Trp Gly
                275                 280                 285

Phe Gly Leu Asp Asn Ile Met His Asn Ile Thr Asn Gly His Val Ala
            290                 295                 300

His His Phe Phe Phe Thr Lys Ile Pro His Tyr His Leu Leu Glu Ala
305                 310                 315                 320

Thr Pro Ala Ile Lys Lys Ala Leu Glu Pro Leu Lys Asp Thr Gln Tyr
                325                 330                 335

Gly Tyr Lys Arg Glu Val Asn Tyr Asn Trp Phe Phe Lys Tyr Leu His
                340                 345                 350

Tyr Asn Val Thr Leu Asp Tyr Leu Thr His Lys Ala Lys Gly Val Leu
                355                 360                 365

Gln Tyr Arg Ser Gly Val Glu Ala Ala Lys Ala Lys Lys Ala Gln
                370                 375                 380

<210> SEQ ID NO 4
<211> LENGTH: 402
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Val Ala His Ser Ser Glu Gly Leu Ser Thr Ala Pro Val Thr
1               5                   10                  15

Gly Gly Asp Val Leu Val Asp Ala Arg Ala Ser Leu Glu Glu Lys Glu
            20                  25                  30

Ala Pro Arg Asp Val Asn Ala Asn Thr Lys Gln Ala Thr Thr Glu Glu
            35                  40                  45

Pro Arg Ile Gln Leu Pro Thr Val Asp Ala Phe Arg Arg Ala Ile Pro
50                  55                  60

Ala His Cys Phe Glu Arg Asp Leu Val Lys Ser Ile Arg Tyr Leu Val
65                  70                  75                  80

Gln Asp Phe Ala Ala Leu Thr Ile Leu Tyr Phe Ala Leu Pro Ala Phe
                85                  90                  95

Glu Tyr Phe Gly Leu Phe Gly Tyr Leu Val Trp Asn Ile Phe Met Gly
            100                 105                 110

Val Phe Gly Phe Ala Leu Phe Val Val Gly His Asp Cys Leu His Gly
            115                 120                 125

Ser Phe Ser Asp Asn Gln Asn Leu Asn Asp Phe Ile Gly His Ile Ala
            130                 135                 140
```

```
Phe Ser Pro Leu Phe Ser Pro Tyr Phe Pro Trp Gln Lys Ser His Lys
145                 150                 155                 160

Leu His His Ala Phe Thr Asn His Ile Asp Lys Asp His Gly His Val
                165                 170                 175

Trp Ile Gln Asp Lys Asp Trp Glu Ala Met Pro Ser Trp Lys Arg Trp
            180                 185                 190

Phe Asn Pro Ile Pro Phe Ser Gly Trp Leu Lys Trp Phe Pro Val Tyr
        195                 200                 205

Thr Leu Phe Gly Phe Cys Asp Gly Ser His Phe Trp Pro Tyr Ser Ser
    210                 215                 220

Leu Phe Val Arg Asn Ser Glu Arg Val Gln Cys Val Ile Ser Gly Ile
225                 230                 235                 240

Cys Cys Cys Val Cys Ala Tyr Ile Ala Leu Thr Ile Ala Gly Ser Tyr
                245                 250                 255

Ser Asn Trp Phe Trp Tyr Tyr Trp Val Pro Leu Ser Phe Phe Gly Leu
            260                 265                 270

Met Leu Val Ile Val Thr Tyr Leu Gln His Val Asp Asp Val Ala Glu
        275                 280                 285

Val Tyr Glu Ala Asp Glu Trp Ser Phe Val Arg Gly Gln Thr Gln Thr
    290                 295                 300

Ile Asp Arg Tyr Tyr Gly Leu Gly Leu Asp Thr Thr Met His His Ile
305                 310                 315                 320

Thr Asp Gly His Val Ala His His Phe Phe Asn Lys Ile Pro His Tyr
                325                 330                 335

His Leu Ile Glu Ala Thr Glu Gly Val Lys Lys Val Leu Glu Pro Leu
            340                 345                 350

Ser Asp Thr Gln Tyr Gly Tyr Lys Ser Gln Val Asn Tyr Asp Phe Phe
        355                 360                 365

Ala Arg Phe Leu Trp Phe Asn Tyr Lys Leu Asp Tyr Leu Val His Lys
    370                 375                 380

Thr Ala Gly Ile Met Gln Phe Arg Thr Thr Leu Glu Glu Lys Ala Lys
385                 390                 395                 400

Ala Lys

<210> SEQ ID NO 5
<211> LENGTH: 1131
<212> TYPE: DNA
<213> ORGANISM: Caenorhabditis elegans

<400> SEQUENCE: 5
atgacaatcg ctacaaaagt gaacacaaat aaaaaggacc ttgatacaat caaggtaccg      60
gagcttccat cagtggcagc tgtcaaagca gcaatccctg agcactgctt tgtcaaggat     120
ccattgactt caatttcata tcttatcaag gattacgtac ttctcgctgg tctctatttt     180
gcagttccat acattgagca ttatctcgga tggatcgggc ttcttggatg gtattgggca     240
atgggaattg ttggatccgc attgttctgt gtgggtcatg actgtggaca tggatcattc     300
tccgattatg aatggctcaa tgatcttttg tggacatttg gctcatgctcc aattcttgct     360 ccattctggc catggcaaaa gtctcataga caacatcatc aatacacatc ccacgtggaa     420
aaggataagg gacatccatg ggttactgag gaagactaca ataatagaac tgctattgag     480
aagtatttcg ctgtgattcc aatttccgga tggcttcgat ggaatccaat ctacaccatc     540
gtcggtcttc cagatggatc tcatttctgg ccatggtccc ggctcttcga gactactgag     600
gatcgtgtca gtgtgcagt tctggagtt gcatgcgcta tctgtgctta cattgccttt     660
```

```
gtcctctgcg actattctgt ctacacattt gtcaagtact actacattcc acttctcttc      720
caaggactta ttctcgtcat tatcacatat cttcaacatc agaatgagga tattgaggtc      780
tacgaagctg atgagtgggg atttgtacgc ggacaaaccc aaactatcga cagacactgg      840
ggattcggac tcgacaacat catgcacaac attaccaacg tcacgtcgc ccatcacttc       900 ttcttcacca aaatcccaca ttatcatctg ttggaggcaa ctccagcaat caagaaagct      960
cttgaaccac tgaaagacac tcaatacgga tacaaacgag aagtcaacta taactggttc     1020
ttcaagtatc ttcactacaa cgttaccctc gactatttga ctcataaagc aaagggtgtc     1080
ctgcaataca gaagtggagt tgaggctgca aaggctaaga aggctcaata a              1131
```

<210> SEQ ID NO 6
<211> LENGTH: 1131
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6

```
atgacaatcg ccacaaaagt gaacacaaat aaaaaagacc tggatacgat caaggtgccg       60
gagctgccaa gcgtggcagc tgtcaaagcc gcaatccctg agcactgctt tgtgaaggat      120
cccttgacta gcatttcata tctgatcaag gattacgtgc ttctcgccgg tctctacttt      180
gcagttccct acatagagca ttatctcgga tggatcgggc tgcttggctg gtattgggcc      240
atgggaattg ttggctccgc attgttctgt gtggggcacg actgcggaca cggatcattc      300
tccgattatg aatggctcaa tgatctgtgt ggccatttag cccatgctcc tattctggct      360
ccgttctggc cctggcagaa atctcaccgc cagcatcacc agtacacatc ccacgtggaa      420
aaggataagg acaccctg ggttactgag gaagactaca ataatcgcac cgccattgag      480
aaatatttcg ccgtgattcc aattagcgga tggctgcgat ggaatcccat ctacaccatc      540
gtcggtctgc ccgatggctc tcacttctgg ccttggtccc ggctcttcga gactaccgag      600
gatcgtgtca agtgtgcagt ttctggcgtt gcatgcgcta tctgcgctta cattgccttt      660
gtgctctgcg actattctgt ctacacattt gtcaagtact actacattcc actgctcttc      720
cagggcctga tcctcgtcat tatcacgtat cttcaacacc agaatgagga tattgaggtc      780
tacgaagccg atgagtgggg cttttgtacgc ggccagaccc agaccatcga caggcactgg      840
ggcttcggac tagacaacat catgcacaac attaccaacg tcacgtcgc ccatcacttc       900 ttcttcacca aaatcccccca ctatcatctg ttggaggcaa ctcccgccat caagaaagcc      960
ctggaacctc tgaaagacac tcagtacgga tacaaacggg aagtcaacta caactggttc     1020
ttcaaatatc tgcactacaa cgtgaccctc gactacttga cccacaaagc aaagggtgtg     1080
ctgcagtacc gcagtggcgt tgaggctgca aaggctaaga aggcccagtg a              1131
```

<210> SEQ ID NO 7
<211> LENGTH: 1627
<212> TYPE: DNA
<213> ORGANISM: Spinacia oleracea

<400> SEQUENCE: 7

```
cacacttcgg cctctccttc tccttcctca aaccaaaaaa aagtctctct gtttttattt       60
aattttttaa aattattaa ttcagagagc taaaaaataa atcacagatt tcgaggttga      120
agaagttcgc aattttttgat ctaccacttc agcggctgga acaatgggtg caggtgggag     180
```

```
atctattcct ccatcggcga gaaaggagaa atctgatgca ttgaacagag taccatacga    240
aaaaccacca ttcacactag ggcagataaa aaaagccatc ccacctcatt gcttcaaacg    300
ctctgtgcta cgctctttct cctatgtggt ttatgatttc accattgcgt tcctcctcta    360
ctatgttgct actaactaca tccacctcct tccaaagcct tcaactact tggcttggcc     420
tgtgtatgga tttgtccaag gctgtgttct taccggtgtt tgggttatag cccatgaatg    480
tggccaccat gccttcagtg attaccagtg gctcgatgac actgttggct tagtcctcca    540
ctcgttcctt cttgtgccat atttctcatg gaaatacagt cacaggcgcc atcactcaaa    600
cactggttca atggagaaag atgaagtttt tgtaccccaa agaaaggaaa atatgtcatg    660
gttttccaag tatcttagca acccacctgg acgaatcctg acccttgttg tgacgctaac    720
ccttggctgg cctttgtatc ttctgtttaa tgtatcgggt aggaaatatg agcgttttgc    780
ttgccattat gacccatcct ctccaatcta ctcggaccgt gagaggcttc aaatattcat    840
ttctgatgtt gggatttcga tagtggcttt tgggctttat caccttgcag ctgccaaagg    900
aatttcatgg gtgttgtgtg tatatggggg tccattgctt gttgtgaacg datttcttgt    960
cctgattacc ttccttcagc acacacaccc ttcattgccc cattacgata catctgaatg    1020
ggattggttg agaggtgcat ggctaccgc ggaccgagac tacgggattt tgaacaaggt    1080
gttccacaac attactgata ctcacgtggc tcaccatctc atctcgacca tgccccatta    1140
tcatgctatg gaggcaacca aggctataaa gccaatattg ggcaaatatt atcggttgga    1200
ttcaactcca gtattcaagg caatgtggag ggaggccaaa gaatgtatgt atgtggaggc    1260
tgatgaagac gaccagaaca aggtgtgct ctggtacaga aacaagcttt aagttgaaag     1320
ttttagtttg atggaagctt ggaaaatcct ggtttctcct ttagggatta gccttctctt    1380
atcctttaaa accccctccc tactagattt ataggttggt tgtgtgtttg tcatgttttg    1440
tatttttgaa ccgcggattt ctttaactac cattccagta atgttggatc attgtgatag    1500
agcgagaatc actaggcgag ttgggggagt tgtttgttat tgttgttta gcaataatct     1560
gtacatcctt gctgtgccca gatttcttgg catatctacg gatgggacac aattatttgt    1620
gaattttt                                                              1627

<210> SEQ ID NO 8
<211> LENGTH: 1209
<212> TYPE: DNA
<213> ORGANISM: Caenorhabditis elegans

<400> SEQUENCE: 8
atggtcgctc attcctcaga agggttatcc gccacggctc cggtcaccgg cggagatgtt     60
ctggttgatg ctcgtgcatc tcttgaagaa aaggaggctc cacgtgatgt gaatgcaaac    120
actaaacagg ccaccactga agagccacgc atccaattac caactgtgga tgctttccgt    180
cgtgcaattc cagcacactg tttcgaaaga gatctcgtta aatcaatcag atatttggtg    240
caagactttg cggcactcac aattctctac tttgctcttc cagcttttga gtactttgga    300
ttgtttggtt acttggtttg gaacattttt atgggagttt ttggattcgc gttgttcgtc    360
gttggacacg attgtcttca tggatcattc tctgataatc agaatctcaa tgatttcatt    420
ggacatatcg ccttctcacc actcttctct ccatacttcc catggcagaa aagtcacaag    480
cttcaccatg ctttcaccaa ccacattgac aaagatcatg gacacgtgtg gattcaggat    540
aaggattggg aagcaatgcc atcatggaaa agatggttca atccaattcc attctctgga    600
```

```
tggcttaaat ggttcccagt gtacacttta ttcggtttct gtgatggatc tcacttctgg    660
ccatactctt cacttttgt tcgtaactct gaacgtgttc aatgtgtaat ctctggaatc    720
tgttgctgtg tgtgtgcata tattgctcta acaattgctg gatcatattc caattggttc    780
tggtactatt gggttccact ttctttcttc ggattgatgc tcgtcattgt tacctatttg    840
caacatgtcg atgatgtcgc tgaggtgtac gaggctgatg aatggagctt cgtccgtgga    900
caaacccaaa ccatcgatcg ttactatgga ctcggattgg acacaacgat gcaccatatc    960
acagacggac acgttgccca tcacttcttc aacaaaatcc cacattacca tctcatcgaa   1020
gcaaccgaag tgtcaaaaa ggtcttggag ccgttgtccg acacccaata cgggtacaaa   1080
tctcaagtga actacgattt ctttgcccgt ttcctgtggt tcaactacaa gctcgactat   1140
ctcgttcaca agaccgccgg aatcatgcaa ttccgaacaa ctctcgagga gaaggcaaag   1200
gccaagtaa                                                          1209

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gcggccagac ccagaccatc                                                20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gggcgacgtg accgttggta                                                20

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tgttcatgcc ttcttctttt tcc                                            23

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gcgaccatac ctcaaacttg ga                                             22

<210> SEQ ID NO 13
<211> LENGTH: 19
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 13
gtgccagcag ccgcggtaa                                                      19

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cctcaagggc acaacctcca ag                                                  22

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tcgcgtccgg tgtgaaag                                                       18

<210> SEQ ID NO 16
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ccacatccag catccac                                                        17

<210> SEQ ID NO 17
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Thr Thr Lys Ser Pro Asp Thr Cys Ser Phe Phe
1               5                   10

<210> SEQ ID NO 18
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Leu Pro Phe Tyr Val Ile Thr Asn Phe Glu Phe Val Phe Glu Asn
1               5                   10                  15

<210> SEQ ID NO 19
<211> LENGTH: 13
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 19

Phe Ser His Ile Ser Met Lys Ile Tyr Val Leu Leu Leu
1               5                   10
```